US010179821B2

(12) United States Patent
Kelley et al.

(10) Patent No.: US 10,179,821 B2
(45) Date of Patent: Jan. 15, 2019

(54) ANTI-FACTOR D ANTIBODIES

(71) Applicant: Genentech, Inc., South San Francisco, CA (US)

(72) Inventors: Robert F Kelley, San Bruno, CA (US); Menno van Lookeren Campagne, San Francisco, CA (US); Justin M Scheer, Burlingame, CA (US); Philip E Hass, Moss Beach, CA (US); Devin Tesar, South San Francisco, CA (US)

(73) Assignee: GENENTECH, INC., South San Francisco, CA (US)

(*) Notice: Subject to any disclaimer, the term of this patent is extended or adjusted under 35 U.S.C. 154(b) by 0 days.

(21) Appl. No.: 14/700,853

(22) Filed: Apr. 30, 2015

(65) Prior Publication Data

US 2016/0017052 A1    Jan. 21, 2016

Related U.S. Application Data

(60) Provisional application No. 61/987,298, filed on May 1, 2014, provisional application No. 62/076,372, filed on Nov. 6, 2014.

(51) Int. Cl.
| *A61K 39/395* | (2006.01) |
| *C07K 16/40* | (2006.01) |
| *A61K 9/00* | (2006.01) |
| *A61K 39/00* | (2006.01) |

(52) U.S. Cl.
CPC ............ *C07K 16/40* (2013.01); *A61K 9/0048* (2013.01); *A61K 2039/505* (2013.01); *C07K 2317/55* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 3,773,919 | A | 11/1973 | Boswell et al. |
| 4,179,337 | A | 12/1979 | Davis et al. |
| 4,741,900 | A | 5/1988 | Alvarez et al. |
| 4,816,567 | A | 3/1989 | Cabilly et al. |
| 4,935,465 | A | 6/1990 | Garman |
| 4,946,778 | A | 8/1990 | Ladner et al. |
| 5,166,322 | A | 11/1992 | Shaw et al. |
| 5,206,344 | A | 4/1993 | Katre et al. |
| 5,225,539 | A | 7/1993 | Winter |
| 5,244,800 | A | 9/1993 | DeLucas et al. |
| 5,456,909 | A | 10/1995 | Marsh, Jr. et al. |
| 5,530,101 | A | 6/1996 | Queen et al. |
| 5,534,615 | A | 7/1996 | Baker et al. |
| 5,571,894 | A | 11/1996 | Wels et al. |
| 5,587,458 | A | 12/1996 | King et al. |
| 5,624,837 | A | 4/1997 | Fodor et al. |
| 5,627,264 | A | 5/1997 | Fodor et al. |
| 5,679,345 | A | 10/1997 | Sanfilippo et al. |
| 5,679,354 | A | 10/1997 | Morein et al. |
| 5,679,546 | A | 10/1997 | Ko et al. |
| 5,679,564 | A | 10/1997 | Pace et al. |
| 5,849,535 | A | 12/1998 | Cunningham et al. |
| 5,851,528 | A | 12/1998 | Ko et al. |
| 5,853,722 | A | 12/1998 | Rollins et al. |
| 5,856,297 | A | 1/1999 | Fearon et al. |
| 5,856,300 | A | 1/1999 | Rittershaus et al. |
| 5,858,969 | A | 1/1999 | Marsh, Jr. et al. |
| 5,861,156 | A | 1/1999 | George et al. |
| 5,869,046 | A | 2/1999 | Presta et al. |
| 5,919,623 | A | 7/1999 | Taylor |
| 6,267,958 | B1 | 7/2001 | Andya et al. |
| 6,333,034 | B1 | 12/2001 | Gupta-Bansal et al. |
| 6,376,653 | B1 | 4/2002 | Holmes et al. |
| 6,407,213 | B1 | 6/2002 | Carter et al. |
| 6,410,708 | B1 | 6/2002 | Ashkenazi et al. |
| 6,472,520 | B2 | 10/2002 | Fisher |
| 6,534,058 | B2 | 3/2003 | Fung et al. |
| 6,569,992 | B1 | 5/2003 | LaFleur et al. |
| 6,642,353 | B1 | 11/2003 | McConnell et al. |
| 6,828,401 | B2 | 12/2004 | Nho et al. |
| 6,838,554 | B2 | 1/2005 | Ashkenazi et al. |
| 6,867,189 | B2 | 3/2005 | Lucas et al. |
| 6,884,879 | B1 | 4/2005 | Baca et al. |
| 6,956,107 | B2 | 10/2005 | Fung et al. |
| 7,005,504 | B2 | 2/2006 | Hsei et al. |
| 7,112,327 | B2 | 9/2006 | Fung et al. |
| 7,122,636 | B1 | 10/2006 | Hsei et al. |
| 7,192,589 | B2 | 3/2007 | Ashkenazi et al. |
| 7,211,400 | B2 | 5/2007 | Ashkenazi et al. |
| 7,282,565 | B2 | 10/2007 | Goddard et al. |

(Continued)

FOREIGN PATENT DOCUMENTS

| EP | 0245993 A2 | 11/1987 |
| EP | 0239400 B1 | 8/1994 |

(Continued)

OTHER PUBLICATIONS

Igawa et al., mAbs 3:3: 243-252, May/Jun. 2011.*
Vlasak et al., mAbs 3:3, May/Jun. 2011.*
1000 Genomes Project Consortium, "A Map of Human Genome Variation from Population-Scale Sequencing" Nature 467(7319):1061-1073 (Oct. 28, 2010).
Accession NM_001928, 'Homo sapiens Complement Factor D (Adipsin) (CFD), mRNA'.
Aderem et al., "Mechanisms of Phagocytosis in Macrophages" Annu. Rev. Immunol. 17:593-623 (1999).
Age-Related Eye Disease Study (AREDS) Research Group, "Potential Public Health Impact of Age-Related Eye Disease Study Results" Arch. Ophthalmol. 121:1621-24 (2003).
Ahamed et al., "Phase Behavior of an Intact Monoclonal Antibody" Biophysical Journal 93:610-619 (Jul. 2007).

(Continued)

Primary Examiner — Phillip Gambel
(74) Attorney, Agent, or Firm — Jones Day

(57) ABSTRACT

The invention relates to anti-Factor D antibody variants, their production and their use in the preparation of compositions and medicaments for treatment of diseases and disorders associated with excessive or uncontrolled complement activation.

9 Claims, 17 Drawing Sheets

Specification includes a Sequence Listing.

(56) References Cited

U.S. PATENT DOCUMENTS

| | | | |
|---|---|---|---|
| 7,351,524 B2 | 4/2008 | Hageman et al. |
| 7,419,663 B2 | 9/2008 | Ashkenazi et al. |
| 7,432,356 B2 | 10/2008 | Fung et al. |
| 7,439,331 B2 | 10/2008 | Fung et al. |
| 7,807,164 B2 | 10/2010 | Furfine et al. |
| 7,816,497 B2 | 10/2010 | Ambati |
| 7,943,135 B2 | 5/2011 | Fung et al. |
| 8,007,791 B2 | 8/2011 | Hass et al. |
| 8,007,798 B2 | 8/2011 | Ashkenazi et al. |
| 8,067,002 B2 | 11/2011 | An et al. |
| 8,124,090 B2 | 2/2012 | Fung et al. |
| 8,142,776 B2 | 3/2012 | Liu et al. |
| 8,187,604 B2 | 5/2012 | An et al. |
| 8,193,329 B2 | 6/2012 | An et al. |
| 8,236,317 B2 | 8/2012 | Fung et al. |
| 8,268,310 B2 | 9/2012 | Hass et al. |
| 8,273,352 B2 | 9/2012 | Huang et al. |
| 8,277,830 B2 | 10/2012 | de Juan, Jr. et al. |
| 8,372,403 B2 | 2/2013 | An et al. |
| 8,383,802 B2 | 2/2013 | Fung et al. |
| 8,399,006 B2 | 3/2013 | de Juan, Jr. et al. |
| 8,481,046 B2 | 7/2013 | Furfine et al. |
| 8,614,306 B2 | 12/2013 | Huang et al. |
| 8,753,826 B2 | 6/2014 | An et al. |
| 8,765,131 B2 | 7/2014 | Fung et al. |
| 8,795,712 B2 | 8/2014 | de Juan, Jr. et al. |
| 8,808,727 B2 | 8/2014 | de Juan, Jr. et al. |
| 2002/0081293 A1 | 6/2002 | Fung et al. |
| 2002/0136719 A1 | 9/2002 | Shenoy et al. |
| 2003/0021790 A1 | 1/2003 | Hsei et al. |
| 2003/0129187 A1 | 7/2003 | Fung et al. |
| 2003/0207309 A1 | 11/2003 | Hageman et al. |
| 2004/0152105 A1 | 8/2004 | Vogt et al. |
| 2004/0177387 A1 | 9/2004 | Jayakrishna |
| 2005/0036991 A1 | 2/2005 | Fodor |
| 2005/0191298 A1 | 9/2005 | Bell et al. |
| 2005/0196394 A1 | 9/2005 | Fung |
| 2005/0197285 A1 | 9/2005 | Rosen et al. |
| 2005/0222027 A1 | 10/2005 | Chiang et al. |
| 2005/0232920 A1 | 10/2005 | Fung et al. |
| 2006/0067935 A1 | 3/2006 | Ambati |
| 2006/0233803 A1 | 10/2006 | Ashkenazi et al. |
| 2006/0240020 A1 | 10/2006 | Fung et al. |
| 2006/0281120 A1 | 12/2006 | Gorin et al. |
| 2007/0020647 A1 | 1/2007 | Hageman et al. |
| 2007/0077233 A1 | 4/2007 | Giordano |
| 2007/0092940 A1 | 4/2007 | Eigenbrot et al. |
| 2007/0098692 A1 | 5/2007 | Kovesdi et al. |
| 2007/0190054 A1 | 8/2007 | Ashkenazi et al. |
| 2008/0118506 A1 | 5/2008 | An et al. |
| 2008/0146501 A1 | 6/2008 | Hageman et al. |
| 2008/0193442 A1 | 8/2008 | Fung et al. |
| 2008/0280825 A1 | 11/2008 | Hageman et al. |
| 2009/0111708 A1 | 4/2009 | Seddon et al. |
| 2009/0124542 A1 | 5/2009 | Hageman et al. |
| 2009/0181017 A1 | 7/2009 | Hass et al. |
| 2009/0214538 A1 | 8/2009 | Fung et al. |
| 2009/0233277 A1 | 9/2009 | Murakami |
| 2009/0253689 A1 | 10/2009 | Baeschlin et al. |
| 2009/0269338 A1 | 10/2009 | Huang et al. |
| 2009/0304694 A1 | 12/2009 | Oliner et al. |
| 2010/0104568 A1* | 4/2010 | Beirnaert ............ C07K 16/24 424/133.1 |
| 2010/0129379 A1* | 5/2010 | Carpenter ........... A61K 9/0019 424/158.1 |
| 2010/0174272 A1 | 7/2010 | Weiner |
| 2011/0014716 A1 | 1/2011 | Swaroop et al. |
| 2011/0123528 A1 | 5/2011 | An et al. |
| 2011/0165622 A1 | 7/2011 | An et al. |
| 2011/0212433 A1 | 9/2011 | Barker et al. |
| 2011/0195069 A1 | 11/2011 | Fung et al. |
| 2011/0268728 A1 | 11/2011 | Borras et al. |
| 2011/0282034 A1 | 11/2011 | Hass et al. |
| 2011/0286956 A1 | 11/2011 | Zhao et al. |
| 2012/0141480 A1 | 6/2012 | Fung et al. |
| 2012/0190578 A1 | 7/2012 | Seddon et al. |
| 2012/0230985 A1 | 9/2012 | An et al. |
| 2012/0230990 A1* | 9/2012 | Beckmann ......... C07K 16/2866 424/133.1 |
| 2012/0322975 A1 | 12/2012 | Fung et al. |
| 2012/0328613 A1 | 12/2012 | Huang et al. |
| 2013/0171070 A1 | 7/2013 | An et al. |
| 2013/0171155 A1 | 7/2013 | Fung et al. |
| 2013/0302333 A1 | 11/2013 | Hass et al. |
| 2014/0065137 A1 | 3/2014 | Huang et al. |
| 2014/0135486 A1 | 5/2014 | Zhao et al. |
| 2015/0073155 A1 | 3/2015 | Yoshioka et al. |
| 2016/0017052 A1 | 1/2016 | Kelley et al. |

FOREIGN PATENT DOCUMENTS

| | | |
|---|---|---|
| EP | 1287364 B1 | 10/2008 |
| RU | 2232991 C1 | 7/2004 |
| WO | 1993/000109 A1 | 1/1993 |
| WO | 1993/016185 A2 | 8/1993 |
| WO | 1994/004188 A1 | 3/1994 |
| WO | 1994/012219 A2 | 6/1994 |
| WO | 1994/022466 A1 | 10/1994 |
| WO | 1995/029697 A1 | 11/1995 |
| WO | 1998/045331 A2 | 10/1998 |
| WO | 1999/001556 A2 | 1/1999 |
| WO | 1999/003887 A1 | 1/1999 |
| WO | 1999/027098 A2 | 3/1999 |
| WO | 1999/040100 A1 | 8/1999 |
| WO | 1999/042133 A1 | 8/1999 |
| WO | 1999/046281 A2 | 9/1999 |
| WO | 2000/012703 A2 | 3/2000 |
| WO | 2000/036102 A2 | 6/2000 |
| WO | 2000/037638 A2 | 6/2000 |
| WO | 2000/042072 A2 | 7/2000 |
| WO | 2000/053749 A2 | 9/2000 |
| WO | 2000/053758 A2 | 9/2000 |
| WO | 2001/004311 A1 | 1/2001 |
| WO | 2001/036432 A2 | 5/2001 |
| WO | 2001/040466 A2 | 6/2001 |
| WO | 2001/084149 A2 | 11/2001 |
| WO | 2002/000690 A2 | 1/2002 |
| WO | 2002/008284 A2 | 1/2002 |
| WO | 2002/030985 A2 | 4/2002 |
| WO | 2002/030986 A2 | 4/2002 |
| WO | 2003/029420 A2 | 4/2003 |
| WO | 2004/001009 A2 | 12/2003 |
| WO | 2004/014953 A2 | 2/2004 |
| WO | 2004/022594 A2 | 3/2004 |
| WO | 2004/032828 A2 | 4/2004 |
| WO | 2004/075837 A2 | 9/2004 |
| WO | 2005/012359 A2 | 2/2005 |
| WO | 2005/025509 A2 | 3/2005 |
| WO | 2005/044853 A2 | 5/2005 |
| WO | 2005/086770 A2 | 9/2005 |
| WO | 2005/102387 A2 | 11/2005 |
| WO | 2006/042329 A2 | 4/2006 |
| WO | 2006/062716 A2 | 6/2006 |
| WO | 2006/071856 A2 | 7/2006 |
| WO | 2006/088950 A2 | 8/2006 |
| WO | 2006/133295 A2 | 12/2006 |
| WO | 2007/044668 A2 | 4/2007 |
| WO | 2007/053447 A2 | 5/2007 |
| WO | 2007/056227 A2 | 5/2007 |
| WO | 2007/087384 A2 | 8/2007 |
| WO | 2008/055206 A2 | 5/2008 |
| WO | 2008/147883 A1 | 12/2008 |
| WO | 2009/029587 A2 | 3/2009 |
| WO | 2009/042686 A1 | 4/2009 |
| WO | 2009/134709 A2 | 11/2009 |
| WO | 2009/134711 A1 | 11/2009 |
| WO | 2009/146204 A1 | 12/2009 |
| WO | 2010/054110 A2 | 5/2010 |
| WO | 2010/075519 A2 | 7/2010 |
| WO | 2010/085542 A2 | 7/2010 |
| WO | 2010/132459 A2 | 11/2010 |
| WO | 2267028 A2 | 12/2010 |
| WO | 2011/017229 A2 | 2/2011 |
| WO | 2011/057014 A1 | 5/2011 |

(56) References Cited

FOREIGN PATENT DOCUMENTS

| WO | 2011/069104 A2 | 6/2011 |
|---|---|---|
| WO | 2012/061421 A1 | 5/2012 |
| WO | 2013/055998 A1 | 4/2013 |
| WO | 2015/023596 A1 | 2/2015 |
| WO | 2015/032776 A1 | 3/2015 |
| WO | 2015/168468 A1 | 11/2015 |

OTHER PUBLICATIONS

Altshuler et al., "Genetic Mapping in Human Disease" Science 322:881-888 (Nov. 7, 2008).
Ambati et al., "An Animal Model of Age-Related Macular Degeneration in Senescent Ccl-2- or Ccr-2-Deficient Mice" Nature Medicine 9(11):1390-1397 (Nov. 2003).
Amin et al., "Genetic Scoring Analysis: A Way Forward in Genome Wide Association Studies?" Eur. J. Epidemiol. 24:585-587 (2009).
Amit et al., "Three-Dimensional Structure of an Antigen-Antibody Complex at 2.8 A Resolution" Science 233:747-753 (Aug. 15, 1986).
Amsterdam et al., "Limitation of Reperfusion Injury by a Monoclonal Antibody to C5a During Myocardial Infarction in Pigs" Am. J. Physiol. 268(1):H448-H457 (Jan. 1995).
Anderson et al., "A Role for Local Inflammation in the Formation of Drusen in the Aging Eye" American Journal of Ophthalmology 134(3):411-431 (Sep. 2002).
Arrate et al., "Cloning of Human Junctional Adhesion Molecule 3 (JAM3) and Its Identification as the JAM2 Counter-Receptor" Journal of Biological Chemistry 276(49):45826-45832 (Dec. 7, 2001).
Attwood, Teresa K., "The Babel of Bioinformatics" Science 290(5491):471-473 (Oct. 2000).
Barnum et al., "Quantitation of Complement Factor D in Human Serum by a Solid-Phase Radioimmunoassay" Journal of Immunological Methods 67(2):303-309 (Mar. 16, 1984).
Benvenuti et al., "Crystallization of Soluble Proteins in Vapor Diffusion for X-Ray Crystallography" Nature Protocols 2(7):1633-1651 (2007).
Bertozzi et al., "An ELISA for Selectins Based on Binding to a Physiological Ligand" Journal of Immunological Methods 203(2):157-165 (Apr. 25, 1997).
Biomarkers Definitions Working Group, "Biomarkers and Surrogate Endpoints: Preferred Definitions and Conceptual Framework" Clinical Pharmacology & Therapeutics 69(3):89-95.
Bok, "Evidence for an Inflammatory Process in Age-Related Macular Degeneration Gains New Support" PNAS 102(20):7053-7054 (May 17, 2005).
Bora et al., "Complement Activation Via Alternative Pathway is Critical in the Development of Laser-Induced Choroidal Neovascularization: Role of Factor B and Factor H" Journal of Immunology 177(3):1872-1878 (2006).
Bora et al., "Role of Complement and Complement Membrane Attack Complex in Laser-Induced Choroidal Neovascularization" Journal of Immunology 174(1):491-497 (2005).
Bora et al., "The Role of Complement in Ocular Pathology" Semin. Immunopathol. 30(2):85-95 (2008).
Brown et al., "Mechanisms of Disease: The Complement System in Renal Injury—New Ways of Looking at an Old Foe" Nature Clinical Practice Nephrology 3(5):277-286 (May 2007).
Brown, "Complement Receptors, Adhesion, and Phagocytosis" Infectious Agents and Disease 1(2):63-70 (1992).
Cancer Genome Atlas Research Network, "Comprehensive Genomic Characterization Defines Human Glioblastoma Genes and Core Pathways" Nature 455(7216):1061-1068 (Oct. 23, 2008).
Carroll, "Exposure of an Executioner" Nature 444: 159-160 (Nov. 9, 2006).
Carter et al., "Humanization of an Anti-P185HER2 Antibody for Human Cancer Therapy" PNAS 89(10):4285-4289 (May 1992).
Casset et al., "A Peptide Mimetic of an Anti-CD4 Monoclonal Antibody by Rational Design" Biochemical and Biophysical Research Communications 307(1):198-205 (Jul. 18, 2003).
Champe et al., "Monoclonal Antibodies that Block the Activity of Leukocyte Function-Associated Antigen 1 Recognize Three Discrete Epitopes in the Inserted Domain of CD11a" Journal of Biological Chemistry 270(3):1388-1394 (Jan. 20, 1995).
Chen et al., "Association between Variant Y402H in Age-Related Macular Degeneration (AMD) Susceptibility Gene CFH and Treatment Response of AMD: A Meta-Analysis" PLoS One 7(8):1-7 (Aug. 2012).
Chen et al., "Enhancement and Destruction of Antibody Function by Somatic Mutation: Unequal Occurrence is Controlled by V Gene Combinatorial Associations" EMBO Journal 14(12):2784-2794 (Jun. 1995).
Chen et al., "Genetic Variants Near TIMP3 and High-Density Lipoprotein-Associated Loci Influence Susceptibility to Age-Related Macular Degeneration" PNAS 107(16):7401-7406 (Apr. 20, 2010).
Chen et al., "Modulating Antibody Pharmacokinetics Using Hydrophilic Polymers" Expert Opinion on Drug Delivery 8(9): 1221-1236 (2011).
Chen et al., "Selection and Analysis of an Optimized Anti-VEGF Antibody: Crystal Structure of an Affinity-Matured Fab in Complex with Antigen" Journal of Molecular Biology 293:865-881 (1999).
Chothia et al., "Canonical Structures for the Hypervariable Regions of Immunoglobulins" Journal of Molecular Biology 196:901-917 (1987).
Collins et al., "Mapping the Cancer Genome: Pinpointing the Genes Involved in Cancer Will Help Chart a New Course Across the Complex Landscape of Human Malignancies" Scientific American 296(3):50-57 (Mar. 2007).
Colman, "Effects of Amino Acid Sequence Changes on Antibody-Antigen Interactions" Res. Immunol. 145:33-36 (1994).
Cudney, "Protein Crystallization and Dumb Luck" The Rigaku Journal 16(1):1-7 (1999).
Database Accession No. NLM20510150, 'Genetic Factors Associated with Age-Related Macular Degeneration', Abstract, May 2010.
de Jong, "Age-Related Macular Degeneration" New England Journal of Medicine 355(14):1474-1485 (Oct. 5, 2006).
Demirkan et al., "Genetic Risk Profiles for Depression and Anxiety in Adult and Elderly Cohorts" Molecular Physhiatry 16:773-783 (2011).
Diamond et al., "Somatic Mutation of the T15 Heavy Chain Gives Rise to an Antibody with Autoantibody Specificity" PNAS 81(18):5841-5844 (Sep. 1984).
Do et al., "A Phase IA Dose-Escalation Study of the Anti-Factor D Monoclonal Antibody Fragment FCFD4514S in Patients with Geographic Atrophy" Retina 34(2):313-320 (2014).
Drenth. Principles of Protein X-Ray Crystallography; "Chapter 1: Crystallizing a Protein" 2nd edition, New York: Springer:1-20.
EBI. Accession No. UNIPROT: P00746 'Complement Factor D' (Jul. 21, 1986).
Edwards et al., "Complement Factor H Polymorphism and Age-Related Macular Degeneration" Science 308(5720):421-424 (Apr. 15, 2005).
Esparza-Gordillo et al., "Genetic and Environmental Factors Influencing the Human Factor H Plasma Levels" Immunogenetics 56(2):77-82 (2004).
Evans et al., "Rapid Expression of an Anti-Human C5 Chimeric Fab Utilizing a Vector that Replicates in COS and 293 Cells" Journal of Immunological Methods 184(1):123-138 (1995).
Extended European Search Report of European Application No. 06836941.2, dated Mar. 2, 2011.
Extended European Search Report of European Application No. 12172001.5, dated Oct. 24, 2012.
Eye Disease Prevalence Research Group, "Prevalence of Age-Related Macular Degeneration in the United States" Arch. Ophthalmol. 122(4):564-572 (Apr. 2004).
Faelber et al., "The 1.85 A Resolution Crystal Structures of Tissue Factor in Complex with Humanized Fab D3h44 and of Free Humanized Fab D3h44: Revisiting the Solvation of Antigen Combining Sites" Journal of Molecular Biology 313:83-97 (2001).

(56) References Cited

OTHER PUBLICATIONS

Fagerness et al., "Variation Near Complement Factor I is Associated with Risk of Advanced AMD" European Journal of Human Genetics 17(1):100-104 (2009).
Farries et al., "The Mechanism of Activation of the Alternative Pathway of Complement by Cell-Bound C4b" Molecular Immunology 27(11):1155-1161 (1990).
Ferris et al., "A Simplified Severity Scale for Age-Related Macular Degeneration: AREDS Report No. 18" Arch. Ophthalmol. 123:1570-1574 (Nov. 2005).
Foote et al., "Antibody Framework Residues Affecting the Conformation of the Hypervariable Loops" Journal of Molecular Biology 224:487-499 (1992).
Francis et al., "Polymorphisms in C2, CFB and C3 are Associated with Progression to Advanced Age Related Macular Degeneration Associated with Visual Loss" J. Med. Genet. 46(5):300-307 (2008).
Fritsche et al., "Seven New Loci Associated with Age-Related Macular Degeneration" Nature Genetics 45(4):435-441 (Apr. 2013).
Fung et al., "Inhibition of Complement, Neutrophil and Platelet Activation by an Anti-Factor D Antibody During Extracorporeal Circulation" (Abstract) Presented at the 18th Annual Houston Conference on Biomedical Engineering Research, Houston, Texas, (Feb. 10-11, 2000).
Fung et al., "Inhibition of Complement, Neutrophil, and Platelet Activation by an Anti-Factor D Monoclonal Antibody in Simulated Cardiopulmonary Bypass Circuits" Journal of Thoracic and Cardiovascular Surgery 122(1):113-122 (Jul. 2001).
Gao et al., "An Enzyme-Linked Immunosorbent Assay to Identify Inhibitors of Activation of Platelet Integrin Alpha IIb Beta 3" Journal of Immunological Methods 181(1):55-64 (Apr. 12, 1995).
Gaudreault et al., "Pharmacokinetics and Retinal Distribution of Ranibizumab, a Humanized Antibody Fragment Directed against VEGF-A, Following Intravitreal Administration in Rabbits" Retina 27(9): 1260-1266 (2007).
Gold et al., "Variation in Factor B (BF) and Complement Component 2 (C2) Genes is Associated with Age-Related Macular Degeneration" Nature Genetics 38(4):458-462 (Apr. 2006).
Gorin, "Genetic Insights into Age-Related Macular Degeneration: Controversies Addressing Risk, Causality, and Therapeutics" Mol. Aspects Med. 33(4):467-486 (Aug. 2012).
Green, "Studies in the Physical Chemistry of the Proteins" Journal of Biological Chemistry 93: 517-542 (1931).
Hageman et al., "A Common Haplotype in the Complement Regulatory Gene Factor H (HF1/CFH) Predisposes Individuals to Age-Related Macular Degeneration" PNAS 102(20):7227-7232 (May 17, 2005).
Hageman et al., "An Integrated Hypothesis that Considers Drusen as Biomarkers of Immune-Mediated Processes at the RPE-Bruch's Membrane Interface in Aging and Age-Related Macular Degeneration" Progress in Retinal and Eye Research 20(6):705-732 (2001).
Haines et al., "Complement Factor H Variant Increases the Risk of Age-Related Macular Degeneration" Science 308:419-421 (Apr. 15, 2005).
Hakimi et al., "Reduced Immunogenicity and Improved Pharmacokinetics of Humanized Anti-Tac in Cynomolgus Monkeys" Journal of Immunology 147(4):1352-1359 (Aug. 15, 1991).
Harboe et al., "The Quantitative Role of Alternative Pathway Amplification in Classical Pathway Induced Terminal Complement Activation" Clin. Exp. Immunol. 138(3):439-446 (2004).
Harlow et al., Antibodies, A Laboratory Manual "Chapter 14: Immunoassays" Cold Spring Harbor Laboratory:553-612 (1988).
Haubenwallner et al., "A Novel Missense Mutation in the Gene for Lipoprotein Lipase Resulting in a Highly Conservative Amino Acid Substitution (Asp180—>Glu) Causes Familial Chylomicronemia (Type I Hyperlipoproteinemia)" Genomics 18(2):392-396 (1993).
Heurich et al., "Common Polymorphisms in C3, Factor B, and Factor H Collaborate to Determine Systemic Complement Activity and Disease Risk" PNAS 108(21):8761-8766 (May 24, 2011).
Hirschhorn et al., "A Comprehensive Review of Genetic Association Studies" Genetics in Medicine 4(2):45-61 (Mar./Apr. 2002).
Hoffman et al., "Rare Complement Factor H Variant Associated with Age-Related Macular Degeneration in the Amish" Investigative Ophthalmology & Visual Science 55(7):4455-4460 (Jul. 2014).
Holers Clinical Immunology: Principles and Practice "Chapter 24: Complement" ed. R.R. Rich, Mosby Press:363-391 (1996).
Holers et al., "The Evolution of Mouse and Human Complement C3-Binding Proteins: Divergence of Form but Conservation of Function" Immunology Today 13(6):231-236 (1992).
Holers, "The Spectrum of Complement Alternative Pathway-Mediated Diseases" Immunological Reviews 223:300-316 (2008).
Holland et al., "Detection of Specific Polymerase Chain Reaction Product by Utilizing the 5'→3' Exonuclease Activity of Thermus Aquaticus DNA Polymerase" PNAS 88(16): 7276-7280 (Aug. 15, 1991).
Holm et al., "Functional Mapping and Single Chain Construction of the Anti-Cytokeratin 8 Monoclonal Antibody TS1" Molecular Immunology 44:1075-1084 (2007).
Holz et al., "Geographic Atrophy: Clinical Features and Potential Therapeutic Approaches" Ophthalmology 121(5):1079-1091 (May 2014).
Holz et al., "Recent Developments in the Treatment of Age-Related Macular Degeneration" Journal of Clinical Investigation 124(4):1430-1438 (Apr. 2014).
Homeister et al., "Soluble Complement Receptor Type 1 Prevents Human Complement-Mediated Damage of the Rabbit Isolated Heart" Journal of Immunology 150(3):1055-1064 (Feb. 1, 1993).
Houghten et al., "The Use of Synthetic Peptide Combinatorial Libraries for the Identification of Bioactive Peptides" BioTechniques 13(3):412-21 (Sep. 1992).
Howie et al., "A Flexible and Accurate Genotype Imputation Method for the Next Generation of Genome-Wide Association Studies" PLoS Genetics 5(6):1-15 (Jun. 2009).
Huber-Lang et al., "Role of C5a in Multiorgan Failure During Sepsis" Journal of Immunology 166(2):1193-1199 (2001).
Inagi et al., "Decreased Activity of Complement-Mediated Immune Complex Clearance in Hemodialysis Patients" Clinical Immunology and Immunopathology 68(3):333-339 (Sep. 1993).
International Preliminary Report on Patentability for PCT/US2006/043103, dated May 6, 2008
International Preliminary Report on Patentability for PCT/US2007/083172, dated Nov. 2, 2006.
International Preliminary Report on Patentability for PCT/US2008/064526, dated Nov. 24, 2009.
International Preliminary Report on Patentability for PCT/US2011/058829, dated May 7, 2013.
International Preliminary Report on Patentability for PCT/US2009/041785, dated Nov. 2, 2010.
International Search Report for PCT/US1999/003566, dated Jun. 2, 1999.
International Search Report for PCT/US2006/043103, dated Aug. 10, 2007.
International Search Report for PCT/US2007/083172, dated Jun. 26, 2008.
International Search Report for PCT/US2008/064526, dated Aug. 14, 2008.
International Search Report for PCT/US2009/041785, dated Sep. 15, 2009.
International Search Report for PCT/US2011/058829, dated Jan. 4, 2012.
International Search Report for PCT/US2014/050579, dated Nov. 28, 2014.
International SNP Working Group, "A Map of Human Genome Sequence Variation Containing 1.42 Million Single Nucleotide Polymorphisms" Nature 409:928-933 (Feb. 15, 2001).
Ioannidis et al., "Replication Validity of Genetic Association Studies" Nature Genetics 29(3):306-309 (Nov. 2001).
Jaffers et al., "Monoclonal Antibody Therapy: Anti-Idiotypic and Non-Anti-Idiotypic Antibodies to OKT3 Arising Despite Intense Immunosuppression" Transplantation 41(5):572-578 (May 1986).
Jager et al., "Age-Related Macular Degeneration" New England Journal of Medicine 359(16):1735-1736 (Oct. 16, 2008).

(56) References Cited

OTHER PUBLICATIONS

Janeway et al., Immunobiology: The Immune System in Health and Disease "13:5-13:7" 3rd edition, London, England :Current Biology Limited (1997).
Janssen et al., "Structural Insights into the Central Complement Component C3" Molecular Immunology 44:3-10 (2007).
Jevsevar et al., "PEGylation of Therapeutic Proteins" Biotechnology Journal 5:113-128 (2010).
Jing et al., "Structural Basis of Profactor D Activation: from a Highly Flexible Zymogen to a Novel Self-Inhibited Serine Protease, Complement Factor D" EMBO Journal 18(4):804-814 (1999).
Jing et al., "Structures of Native and Complexed Complement Factor D: Implications of the Atypical His57 Conformation and Self-Inhibitory Loop in the Regulation of Specific Serine Protease Activity" Journal of Molecular Biology 282:1061-1081 (1998).
Johnson et al., "Complement Activation and Inflammatory Processes in Drusen Formation and Age Related Macular Degeneration" Exp. Eye Res. 73(6):887-896 (2001).
Jones et al., "Replacing the Complementarity-Determining Regions in a Human Antibody with those from a Mouse" Nature 321:522-525 (May 29, 1986).
Joubert et al., "Classification and Characterization of Therapeutic Antibody Aggregates" Journal of Biological Chemistry 286(28): 25118-25133 (Jul. 15, 2011).
Joubert et al., "Highly Aggregated Antibody Therapeutics Can Enhance the In Vitro Innate and Late-Stage T-Cell Immune Responses" Journal of Biological Chemistry 287(30): 25266-25279 (Jul. 20, 2012).
Junghans et al., "Anti-Tac-H, a Humanized Antibody to the Interleukin 2 Receptor with New Features for Immunotherapy in Malignant and Immune Disorders" Cancer Research 50(5):1495-1502 (Mar. 1, 1990).
Kathiresan et al., "Polymorphisms Associated with Cholesterol and Risk of Cardiovascular Events" (Abstract), Journal of Vascular Surgery:1372 (Jun. 2008).
Katschke et al., "A Novel Inhibitor of the Alternative Pathway of Complement Reverses Inflammation and Bone Destruction in Experimental Arthritis" Journal of Experimental Medicine 201(6):1319-1325 (Jun. 11, 2007).
Katschke et al., "Inhibiting Alternative Pathway Complement Activation by Targeting the Factor D Exosite" Journal of Biological Chemistry 287(16):12886-12892 (Apr. 13, 2012).
Katschke et al., "Structural and Functional Analysis of a C3b-Specific Antibody that Selectively Inhibits the Alternative Pathway of Complement" Journal of Biological Chemistry 284 (16):10473-10479 (Apr. 17, 2009).
Khazaeli et al., "Phase I Trial of Multiple Large Doses of Murine Monoclonal Antibody CO17-1A. II. Pharmacokinetics and Immune Response" Journal of the National Cancer Institute 80(12):937-942 (Aug. 17, 1988).
Kim et al., "Characterization of Monoclonal Antibody Specific to the Z39Ig Protein, a Member of Immunoglobulin Superfamily" Immunology Letters 99(2):153-161 (2005).
Kim et al., "Crystal Structure of a Complement Factor D Mutant Expressing Enhanced Catalytic Activity" Journal of Biological Chemistry 270(41):24399-24405 (Oct. 13, 1995).
Klein et al., "Complement Factor H Polymorphism in Age-Related Macular Degeneration" Science 308(5720):385-389 (Apr. 15, 2005).
Kloeckener-Gruissem et al., "Genetic Association with Response to Intravitreal Ranibizumab in Patients with Neovascular AMD" Investigative Ophthalmology & Visual Science 52(7):4694-4702 (Jun. 2011).
Klohs et al., "Inhibitors of Tyrosine Kinase" Current Opinion in Oncology 9(6):562-568 (Nov. 1997).
Kontermann, "Strategies to Extend Plasma Half-Lives of Recombinant Antibodies" Biodrugs 23(2): 93-109 (2009).
Kostavasili et al., "Mechanism of Complement Inactivation by Glycoprotein C of Herpes Simplex Virus" Journal of Immunology 158(4):1763-1771 (Feb. 15, 1997).
Kozlov et al., "Isotyping of Human C4 Complement Using Differences in the Functional Activity of Isotypes C4A and C4B" Russian Journal of Bioorganic Chemistry 26(7):482-489 (2000).
Kroshus et al., "Complement Inhibition with an Anti-C5 Monoclonal Antibody Prevents Acute Cardiac Tissue Injury in an Ex Vivo Model of Pig-to-Human Xenotransplantation" Transplantation 60(11):1194-1202 (Dec. 15, 1995).
Krzystolik et al., "Prevention of Experimental Choroidal Neovascularization with Intravitreal Anti-Vascular Endothelial Growth Factor Antibody Fragment" Arch. Ophthalmol. 120(3):338-46 (Mar. 2002).
Kumagai et al., "Generation of Novel Functional Antibody Molecules by In Vitro Selection System" Tanpakushitsu Kakusan Koso (Protein Nucleic Acid and Enzyme Review) (Japanese with English translation of Abstract), 43(2):159-167 (1998).
Kundrot, "Which Strategy for a Protein Crystallization Project?" Cellular and Molecular Life Sciences 61:525-536 (2004).
Kussie et al., "A Single Engineered Amino Acid Substitution Changes Antibody Fine Specificity" Journal of Immunology 152(1):146-152 (Jan. 1994).
Lam et al., "Application of Combinatorial Library Methods in Cancer Research and Drug Discovery" Anti-Cancer Drug Design 12(3):145-167 (Apr. 1997).
Langnaese et al., "Cloning of Z39Ig, a Novel Gene with Immunoglobulin-Like Domains Located on Human Chromosome X1" Biochimica et Biophysica Acta 1492:522-525 (2000).
Lee et al., "Z39Ig is Expressed on Macrophages and May Mediate Inflammatory Reactions in Arthritis and Atherosclerosis" Journal of Leukocyte Biology 80(4):922-928 (Oct. 2006).
Lesavre et al., "Mechanism of Action of Factor D of the Alternative Complement Pathway" Journal of Experimental Medicine 148(6):1498-1509 (Dec. 1978).
Lettre et al., "Autoimmune Diseases: Insights from Genome-Wide Association Studies" Human Molecular Genetics 17(2):R116-R121 (2008).
Lim et al., "Age-Related Macular Degeneration" Lancet 379(9827):1728-1738 (May 5, 2012).
Loubser et al., "Inhibition of Complement, Neutrophil and Platelet Activation by an Anti-Factor D Antibody During Extracorporeal Circulation", Presented at the Animal Meeting of American Society of Anesthesiologists, San Francisco, California, Oct. 14-18, 2000 (Abstract A-657).
Lowe et al., "Aggregation, Stability, and Formulation of Human Antibody Therapeutics" Advances in Protein Chemistry and Structural Biology 84: 41-61 (2011).
Loyet et al., "Activation of the Alternative Complement Pathway in Vitreous is Controlled by Genetics in Age-Related Macular Degeneration" Investigative Ophthalmology & Visual Science 53(10):6628-6637 (Sep. 2012).
Loyet et al., "Anti-Factor D Fab Specifically Inhibits the Alternative Complement Pathway: In Vitro Characterization and In Vivo Effects Following Administration to Cynomolgus Monkeys" (Abstract) Investigative Ophthalmology & Visual Science 51(13) (Apr. 2010).
MacCallum et al., "Antibody-Antigen Interactions: Contact Analysis and Binding Site Topography" Journal of Molecular Biology 262(5):732-745 (Oct. 11, 1996).
Makrides, "Therapeutic Inhibition of the Complement System" Pharmacological Reviews 50(1):59-87 (1998).
Matson et al., "Evolving Concepts of Therapy for Sepsis and Septic Shock and the Use of Hyperpermeable Membranes" Current Opinion in Critical Care 6:431-436 (2000).
McPherson, "Current Approaches to Macromolecular Crystallization" Eur. J. Biochem. 189:1-23 (1990).
Meredith et al., Intraocular Drug Delivery, ed. G. J. Jaffe, Taylor & Francis:86-95, 111-128, 193-225, 249-263 (2006).
Miller et al., "Monoclonal Antibody Therapeutic Trials in Seven Patients with T-Cell Lymphoma" Blood 62(5):988-995 (Nov. 1983).
Mohlke et al., "Metabolic and Cardiovascular Traits: An Abundance of Recently Identified Common Genetic Variants" Human Molecular Genetics 17(2):R102-R108 (2008).
Moon et al., "A Synergistic Approach to Protein Crystallization: Combination of a Fixed-Arm Carrier with Surface Entropy Reduction" Protein Science 19:901-913 (2010).

(56) References Cited

OTHER PUBLICATIONS

Moore et al., "Role of Aggregated Human Growth Hormone (hGH) in Development of Antibodies to hGH" Journal of Endocrinology and Metabolism 51(4): 691-697 (1980).
Morgan, "Clinical Complementology: Recent Progress and Future Trends" European Journal of Clinical Investigation 24:219-228 (1994).
Mulligan et al., "Protective Effects of Soluble CR1 in Complement- and Neutrophil-Mediated Tissue Injury" Journal of Immunology 148(5):1479-1485 (Mar. 1, 1992).
Mullins et al., "Drusen Associated with Aging and Age-Related Macular Degeneration Contain Proteins Common to Extracellular Deposits Associated with Atherosclerosis, Elastosis, Amyloidosis, and Dense Deposit Disease" FASEB Journal 14(7):835-846 (May 2000).
Narayana et al., "Structure of Human Factor D: A Complement System Protein at 2.0 A Resolution" Journal of Molecular Biology 235(2):695-708 (1994).
Neale et al., "Genome-Wide Association Study of Advanced Age-Related Macular Degeneration Identifies a Role of the Hepatic Lipase Gene (LIPC)" PNAS 107(16):7395-7400 (Apr. 20, 2010).
New American Webster Handy College Dictionary, 4th Edition, pp. 556-567 and 694, 2006.
Niemann et al., "The Use of Monoclonal Antibodies as Probes of the Three-Dimensional Structure of Human Complement Factor D" Journal of Immunology 132(2):809-815 (Feb. 1984).
Ohno et al., "Antigen Binding Specificities of Antibodies are Primarily Determined by Seven Residues of $V_h$," PNAS 82(9):2945-2949 (May 1985).
Oliphant et al., "BeadArray™ Technology: Enabling an Accurate, Cost-Effective Approach to High-Throughput Genotyping" BioTechniques 32 (Suppl S56-S61):56-61 (Jun. 2002).
Omer et al., "CA1A2X-Competitive Inhibitors of Farnesyltransferase as Anti-Cancer Agents" TiPS 18(11):437-444 (Nov. 1997).
Padlan et al., "Structure of an Antibody-Antigen Complex: Crystal Structure of the HyHEL-10 Fab-Lysozyme Complex" PNAS 86:5938-5942 (Aug. 1989).
Pangburn, "Alternative Pathway of Complement" Methods in Enzymology 162: 639-653 (1988).
Pascual et al., "A Monoclonal Antibody which Blocks the Function of Factor D of Human Complement" Journal of Immunological Methods 127(2):263-269 (Mar. 9, 1990).
Pascual et al., "Inhibition of Complement Alternative Pathway in Mice with Fab Antibody to Recombinant Adipsin/Factor D" Eur. J. Immunol. 23(6):1389-1392 (Jun. 1993).
Pascual et al., "Metabolism of Complement Factor D in Renal Failure" Kidney International 34(4):529-536 (Oct. 1988).
Paul et al., Fundamental Immunology, 3rd edition, Raven Press: 292-295 (1993).
PCT Written Opinion of the International Searching Authority for PCT/US2006/043103.
PCT Written Opinion of the International Searching Authority for PCT/US2009/041785.
PCT Written Opinion of the International Searching Authority for PCT/US2014/050579.
PCT Written Opinion of the International Searching Authority for PCT/US2007/083172.
PCT Written Opinion of the International Searching Authority for PCT/US2011/058829.
PCT Written Opinion of the International Searching Authority for PCT/US2008/064526.
Petrukhin, "New Therapeutic Targets in Atrophic Age-Related Macular Degeneration" Expert Opin. Ther. Targets 11(5):625-639 (2007).
Plackett "Studies in the History of Probability and Statistics. XXIX: The Discovery of the Method of Least Squares" Biometricka 59(2):239-251 (1972).
Powell et al., "A Compendium and Hydropathy/Flexibility Analysis of Common Reactive Sites in Proteins: Reactivity at Asn, Asp, Gln, and Met Motifs in Neutral pH Solution" Pharm. Biotechnol. 9:1-140 (1996).
Prosser et al., "Structural Basis for Complement Factor H-Linked Age-Related Macular Degeneration" Journal of Experimental Medicine 204(10):2277-2283 (Oct. 1, 2007).
Purcell et al., "Common Polygenic Variation Contributes to Risk of Schizophrenia and Bipolar Disorder" Nature 460:748-752 (Aug. 6, 2009).
Pyz et al., "C-Type Lectin-Like Receptors on Myeloid Cells" Annals of Medicine 38(4):242-251 (2006).
Rabinovici et al., "Role of Complement in Endotoxin/Platelet-Activating Factor-Induced Lung Injury" Journal of Immunology 149(5):1744-1750 (Sep. 1, 1992).
Ray et al., "Thrombin Receptor: A Novel Target for Antiplatelet Drug Development" Thrombosis Research 87(1):37-50 (1997).
Reynolds et al., "Plasma Complement Components and Activation Fragments: Associations with Age-Related Macular Degeneration Genotypes and Phenotypes" Invest Ophthalmol. Vis Sci. 50(12):5818-5827 (Dec. 2009).
Ricklin et al., "Complement: A Key System for Immune Surveillance and Homeostasis" Nat. Immunol. 11(9):785-797 (Sep. 2010).
Ricklin et al., "Complement-Targeted Therapeutics" Nature Biotechnology 25(11):1265-1275 (Nov. 2007).
Riechmann et al., "Reshaping Human Antibodies for Therapy" Nature 332:323-327 (Mar. 24, 1988).
Rinder et al., "Blockade of C5a and C5b-9 Generation Inhibits Leukocyte and Platelet Activation during Extracorporeal Circulation" J. Clin. Invest. 96(3):1564-1572 (Sep. 1995).
Rodriguez de Cordoba et al., "The Human Complement Factor H: Functional Roles, Genetic Variations and Disease Associations" Molecular Immunology 41:355-367 (2004).
Rohrer et al., "A Targeted Inhibitor of the Alternative Complement Pathway Reduces Angiogenesis in a Mouse Model of Age-Related Macular Degeneration" Investigative Ophthalmology & Visual Science 50(7):3056-64 2009.
Rohrer et al., "Eliminating Complement Factor D Reduces Photoreceptor Susceptibility to Light-Induced Damage" Investigative Ophthalmology & Visual Science 48(11):5282-5289 (Nov. 2007).
Roitt et al., Immunology (Translated from Russian by the McElroy Translation Company), 5th edition, London: Mosby:110-113 (1998).
Rosenberg, "Effects of Protein Aggregates: An Immunologic Perspective" The AAPS Journal 8(3): E501-E507 (Aug. 4, 2006).
Ross et al., "Membrane Complement Receptors Specific for Bound Fragments of C3" Advances in Immunology 37:217-267 (1985).
Roversi et al., "Structural Basis for Complement Factor I Control and Its Disease-Associated Sequence Polymorphisms" PNAS 108(31):12839-12844 (Aug. 2, 2011).
Rudikoff et al., "Single Amino Acid Substitution Altering Antigen-Binding Specificity" PNAS 79:1979-1983 (Mar. 1982).
Sahu et al., "Identification of Multiple Sites of Interaction Between Heparin Complement System" Molecular Immunology 30(7):679-684 (May 1993).
Salas-Solano et al., "Robustness of iCIEF Methodology for the Analysis of Monoclonal Antibodies: An Interlaboratory Study" J. Sep. Sci. 35: 3124-3129 (2012).
Sallo et al., "The International Classification System and the Progression of Age-Related Macular Degeneration" Current Eye Research 34(3):238-240 (Mar. 2009).
Sambrook et al., Molecular Cloning "Chapter 5" Cold Spring Harbor Laboratory Press, 3rd edition (2001).
Sambrook et al., Molecular Cloning "Chapter 9" Cold Spring Harbor Laboratory Press, 3rd edition (2001).
Sato et al., "A New Method for Studying the Binding of Human IgE to CD23 and the Inhibition of This Binding" Journal of Immunological Methods 209(1):59-66 (Nov. 10, 1997).
Scheffe, The Analysis of Variance "1.2, Mathematical Models" New York: John Wiley & Sons:4-7 (1999).
Schifferli et al., Complements Facts Book "Factor D" Morley, vol. 17:69-72 (2000).
Scholl et al., "Systemic Complement Activation in Age-Related Macular Degeneration" PLoS One 3(7):1-7 (Jul. 2008).
Schweitzer et al., "Combining Nucleic Acid Amplification and Detection" Current Opinion in Biotechnology 12(1):21-27 (2001).

(56) References Cited

OTHER PUBLICATIONS

Sears et al., "Effects of Monoclonal Antibody Immunotherapy on Patients with Gastrointestinal Adenocarcinoma" Journal of Biological Response Modifiers 3(2):138-150 (1984).
Seddon et al., "Association of CFH Y402H and LOC387715 A69S with Progression of Age-Related Macular Degeneration" JAMA 297(16):1793-1800, 2585 (Apr. 25, 2007).
Seddon et al., "Prediction Model for Prevalence and Incidence of Advanced Age-Related Macular Degeneration Based on Genetic, Demographic, and Environmental Variables" Investigative Ophthalmology & Visual Science 50(5):2044-2053 (May 2009).
Seddon et al., "Rare Variants in CFI, C3 and C9 are Associated with High Risk of Advanced Age-Related Macular Degeneration" Nature Genetics 45(11):1366-1370 (Nov. 2013).
Seddon et al., "Risk Models for Progression to Advanced Age-Related Macular Degeneration Using Demographic, Environmental, Genetic, and Ocular Factors" Ophthalmology 118(11):2203-2211 (Nov. 2011).
Shawler et al., "Human Immune Response to Multiple Injections of Murine Monoclonal IgG$^1$" Journal of Immunology 135(2):1530-1535 (Aug. 1985).
Sim et al., "Serine Proteases of the Complement System" Biochemical Society Transactions 28(5):545-550 (2000).
Sims et al., "A Humanized CD18 Antibody Can Block Function Without Cell Destruction" Journal of Immunology 151(4):2296-2308 (Aug. 15, 1993).
Skolnick et al., "From Genes to Protein Structure and Function: Novel Applications of Computational Approaches in the Genomic Era" TibTech 18:34-39 (Jan. 2000).
Stadel et al., "Orphan G Protein-Coupled Receptors: A Neglected Opportunity for Pioneer Drug Discovery" TiPS 18(11):430-437 (Nov. 1997).
Stanton et al., "Complement Factor D in Age-Related Macular Degeneration" Investigative Ophthalmology & Visual Science 52(12):8828-8834 (Nov. 2011).
Strausberg et al., "Generation and Initial Analysis of More than 15,000 Full-Length Human and Mouse cDNA Sequences" PNAS 99(26):16899-16903 (Dec. 24, 2002).
Strawn et al., "Flk-1 as a Target for Tumor Growth Inhibition" Cancer Research 56(15):3540-3545 (Aug. 1, 1996).
Streiner Encyclopedia of Research Design "Last Observation Carried Forward" Salkind, Thousand Oaks:Sage Publications, Inc., vol. 2:687-689 (2010).
Stuart et al., "Phagocytosis: Elegant Complexity" Immunity 22(5):539-550 (2005).
Sunness et al., "Designing Clinical Trials for Age-Related Geographic Atrophy of the Macula" Retina 27(2):204-210 (2007).
Sunness et al., "Visual Function Abnormalities and Prognosis in Eyes with Age-Related Geographic Atrophy of the Macula and Good Visual Acuity" Ophthalmology 104(10):1677-1691 (Oct. 1997).
Tamura et al., "Structural Correlates of an Anticarcinoma Antibody: Identification of Specificity-Determining Residues (SDRs) and Development of a Minimally Immunogenic Antibody Variant by Retention of SDRs Only" Journal of Immunology 164:1432-1441 (2000).
Tanhehco et al., "The Anti-Factor D Antibody, MAb 166-32, Inhibits the Alternative Pathway of the Human Complement System" Transplantation Proceedings 31(5):2168-2171 (Aug. 1999).
Taylor et al., "Macrophage Receptors and Immune Recognition" Annu. Rev. Immunol. 23:901-944 (2005).
Taylor et al., "Pattern Recognition Receptors and Differentiation Antigens Define Murine Myeloid Cell Heterogeneity Ex Vivo" Eur. J. Immunol. 33(8):2090-2097 (2003).
Thurman et al., "The Central Role of the Alternative Complement Pathway in Human Disease" Journal of Immunology 176(3):1305-10 (2006).
Tsuchihashi et al., "Complement Factor H and High-Temperature Requirement A-1 Genotypes and Treatment Response of Age-Related Macular Degeneration" Ophthalmology 118(1):93-100 (Jan. 2011).

Tsukita et al., "Multifunctional Strands in Tight Junctions" Nature Reviews: Molecular Cell Biology 2(4):285-293 (Apr. 2001).
Undar et al., "Novel Anti-Factor D Monoclonal Antibody Inhibits Complement, Neutrophil, and Platelet Activation in a Simulated Pediatric Cardiopulmonary Bypass Circuit" (Abstract) 200 Abstracts & Information, presented at the 46th Annual Conference of the American Society for Artificial Internal Organs, New York City, USA, (Jun. 28, 2000-Jul. 1, 2000).
Undar et al., "Novel Anti-Factor D Monoclonal Antibody Inhibits Complement and Leukocyte Activation in a Baboon Model of Cardioplumonary Bypass" Ann. Thorac. Surg. 74(2):355-362 (2002).
Underhill et al., "Phagocytosis of Microbes: Complexity in Action" Annual Review of Immunology 20:825-852 (2002).
Vajdos et al., "Comprehensive Functional Maps of the Antigen-Binding Site of an Anti-ErbB2 Antibody Obtained with Shotgun Scanning Mutagenesis" Journal of Molecular Biology 320:415-428 (2002).
van de Ven et al., "A Functional Variant in the CFI Gene Confers a High Risk of Age-Related Macular Degeneration" Nature Genetics 45(7):813-819 (Jul. 2013).
van Lookeren Campagne et al., "Mechanisms of Age-Related Macular Degeneration and Therapeutic Opportunities" Journal of Pathology 232(2):151-164 (2014).
Verhoeyen et al., "Reshaping Human Antibodies: Grafting an Antilysozyme Activity" Science 239:1534-1536 (Mar. 25, 1988).
Volanakis et al., "Complement Factor D, a Novel Serine Protease" Protein Science 5(4):553-564 (1996).
Volanakis et al., "Renal Filtration and Catabolism of Complement Protein D" New England Journal of Medicine 312(7):395-399 (1985).
Volanakis et al., The Human Complement System in Health & Disease "Chapter 4, Complement Enzymes" New York: Marcel Dekker, Inc.:49-81 (1998).
Walker, "Z39Ig is Co-Expressed with Activated Macrophage Genes" Biochimica et Biophysica Acta 1574(3):387-390 (2002).
Walport, "Complement: First of Two Parts" New England Journal of Medicine 344(14):1058-1066 (Apr. 5, 2001).
Wang et al., "Amelioration of Lupus-Like Autoimmune Disease in NZB/WF1 Mice after Treatment with a Blocking Monoclonal Antibody Specific for Complement Component C5" PNAS 93(16):8563-8568 (Aug. 1996).
Wang et al., "Anti-C5 Monoclonal Antibody Therapy Prevents Collagen-Induced Arthritis and Ameliorates Established Disease" PNAS 92(19):8955-8959 (Sep. 1995).
Wang et al., "Antibody Structure, Instability, and Formulation" Journal of Pharmaceutical Sciences 96(1): 1-26 (Jan. 2007).
Weber, "Overview of Protein Crystallization Methods" Methods in Enzymology 276:13-22 (1997).
Wei et al., "From Disease Association to Risk Assessment: An Optimistic View from Genome-Wide Association Studies on Type 1 Diabetes" PLoS Genetics 5(10):1-11 (Oct. 2009).
Weisman et al., "Soluble Human Complement Receptor Type 1: In Vivo Inhibitor of Complement Suppressing Post-Ischemic Myocardial Inflammation and Necrosis" Science 249(4965):146-151 (Jul. 13, 1990).
White et al., "Human Adipsin is Identical to Complement Factor D and is Expressed at High Levels in Adipose Tissue" Journal of Biological Chemistry 267(13):9210-9213 (May 5, 1992).
Wiesmann et al., "Structure of C3b in Complex with CRIg Gives Insights into Regulation of Complement Activation" Nature 444:217-220 (Nov. 9, 2006).
Wilson et al., "A Competitive Inhibition ELISA for the Quantification of Human Interferon-gamma" Journal of Immunological Methods 162(2):247-255 (Jun. 18, 1993).
Wong et al., "Global Prevalence of Age-Related Macular Degeneration and Disease Burden Projection for 2020 and 2040: A Systematic Review and Meta-Analysis" Lancet Global Health 2(2):e106-116 (Feb. 2014).
Wu et al., "BioGPS: An Extensible and Customizable Portal for Querying and Organizing Gene Annotation Resources" Genome Biology 10(11):R130.1-R130.8 (2009).
Wu et al., "Fast and SNP-Tolerant Detection of Complex Variants and Splicing in Short Reads" Bioinformatics 26(7):873-81 (2010).

(56) References Cited

OTHER PUBLICATIONS

Wu et al., "Humanization of a Murine Monoclonal Antibody by Simultaneous Optimization of Framework and CDR Residues" Journal of Molecular Biology 294(1):151-162 (Nov. 19, 1999).
Yates et al., "Complement C3 Variant and the Risk of Age-Related Macular Degeneration" New England Journal of Medicine 357(6):553-561 (Aug. 9, 2007).
Yu et al., "Prospective Assessment of Genetic Effects on Progression to Different Stages of Age-Related Macular Degeneration Using Multistate Markov Models" Investigative Ophthalmology & Visual Science 53(3):1548-1556 (Mar. 2012).
Zareparsi et al., "Strong Association of the Y402H Variant in Complement Factor H at 1q32 with Susceptibility to Age-Related Macular Degeneration" Am. J. Hum. Genet. 77(1):149-153 (2005).
Zeng et al., "Lack of Association of CFD Polymorphisms with Advanced Age-Related Macular Degeneration" Molecular Vision 16:2273-2278 (2010).
Bielefeld-Sevigny, "AlphaLISA Immunoassay Platform—The "No-Wash" High-Throughput Alternative to ELISA" Assay Drug Dev Technol 7:90-92 (2009).
Cacia et al., "Isomerization of an Aspartic Acid Residue in the Complementarity-Determining Regions of a Recombinant Antibody to Human IgE: Identification and Effect on Binding Affinity" Biochemistry 35:1897-1903 (1996).
Cunningham et al., "High-resolution epitope mapping of hGH-receptor interactions by alanine-scanning mutagenesis" Science 24:1081-1085 (Jun. 2, 1989).
Damico et al., "New Approaches and Potential Treatments for Dry Age-Related Macular Degeneration" Arq Bras Oftalmol 75(1):71-76 (2012).
Database dbSNP, rs1329428, 6 pgs, 2004 (date retrieved: May 18, 2017).
Database dsSNP, RS429608, 4 pgs, 2003 (date retrieved: May 18, 2017).
Duddu et al., "The Relationship Between Protein Aggregration and Molecular Mobility Below the Glass Transition Temperature of Lyophilized Formulations Containing a Monoclonal Antibody" Pharmaceutical Research 14(5):596-600 (1997).
Duvvuri et al., "Drug Delivery to the Retina: Challenges and Opportunities" Expert Opin Biol Ther. 3(1):45-56 (2003).
Geiger et al., "Deamidation, Isomerization, and Racemization at Asparaginyl and Aspartyl Residues in Peptides" Journal of Biological Chemistry 262(2):785-794 (Jan. 15, 1987).
Ghate et al., "Ocular Drug Delivery" Expert Opinion on Drug Delivery 3(2):275-287 (2006).
Glickman et al., "A Comparison of ALPHAScreen, TR-FRET, and TRF as Assay Methods for FXR Nuclear Receptors" Journal of Biomolecular Screening 7(1):3-10 ( 2002).
Gullberg et al., "Cytokine Detection by Antibody-Based Proximity Ligation" PNAS 101(22):8420-8424 (Jun. 1, 2004).
Jones, "Analysis of Polypeptides and Proteins." Adv Drug Delivery Rev 10:29-90 (1993).
Junutula et al., "Rapid identification of reactive cysteine residues for site-specific labeling of antibody-Fabs" J Immunol Methods 332:41-52 (2008).
Kelley et al. Antibody Methods and Protocols "18" Proetzel et al.,Humana Press, vol. 901:277-293 (2012).
Loyet et al., "Complement Inhibition in Cynomolgus Monkeys by Anti-Factor D Antigen-Binding Fragment for the Treatment of an Advanced Form of Dry Age-Related Macular Degeneration" Journal of Pharmacology and Experimental Therapeutics 351:527-537 (Dec. 2014).
Michels et al., "Fluorescent Derivatization Method of Proteins for Characterization by Capillary Electrophoresis-Sodium Dodecyl Sulfate with Laser-Induced Fluorescence Detection" Analytical Chemistry 79(15):5963-5971 (Aug. 1, 2007).
Michels et al., "Quantitative Impurity Analysis of Monoclonal Antibody Size Heterogeneity by CE-LIF: Example of Development and Validation Through a Quality-By-Design Framework" Electrophoresis 33:815-826 ( 2012).

Morrison, "Time-Resolved Detection of Energy Transfer: Theory and Application to Immunoassays" Analytical Biochemistry 174:101-120 (1988).
Pedley et al., "The Potential for Enhanced Tumour Localisation by Poly(ethylene glycol) Modification of Anti-CEA Antibody" Br. J. Cancer 70:1126-1130 (1994).
Pikal et al., "Solid State Chemistry of Proteins: II. The Correlation of Storage Stability of Freeze-Dried Human Growth Hormone (hGH) with Structure and Dynamics in the Glassy Solid" Journal of Pharmaceutical Sciences 97(12):5106-5121 (Dec. 2008).
Selvin, "Fluorescence Resonance Energy Transfer" Methods in Enzymology 246:300-335 (1995).
Sivakumaran et al., "A 32 kb Critical Region Excluding Y402H in CFH Mediates Risk for Age-Related Macular Degeneration" PLoS ONE 6(10 SUPPL e25598):1-13 (Oct. 2011).
Stryer, "Fluorescence Energy Transfer as a Spectroscopic Ruler" Ann. Rev. Biochem. 47:819-846 (1978).
Ullman et al., "Luminescent Oxygen Channeling Assay (LOCITM): Sensitive, Broadly Applicable Homogeneous Immunoassay Method" Clinical Chemistry 42(9):1518-1526 (Sep. 1996).
Ullman et al., "Luminescent Oxygen Channeling Immunoassay: Measurement of Particle Binding Kinetics by Chemiluminescence" PNAS 91:5426-5430 (Jun. 1994).
Urtti, "Challenges and Obstacles of Ocular Pharmacokinetics and Drug Delivery" Advanced Drug Delivery Reviews 58:1131-1135 (2006).
Walsh, "Biopharmaceutical Benchmarks" Nature Biotechnology 18:831-833 (Aug. 2000).
Wang et al., "Effect of Ionic Strength and pH on the Physical and Chemical Stability of a Monoclonal Antibody Antigen-Binding Fragment" Journal of Pharmaceutical Sciences 102(8):2520-2537 (Aug. 2013).
Xie et al., "Secondary Structure and Protein Deamidation" Journal of Pharmaceutical Sciences 88(1):8-13 (Jan. 1999).
Yi et al., "Isomerization of Asp-Asp Motif in Model Peptides and a Monoclonal Antibody Fab Fragment" Journal of Pharmaceutical Sciences 102(3):947-959.
Zhang et al., "Identification of Isomerization and Racemization of Aspartate in the Asp-Asp Motifs of a Therapeutic Protein" Analytical Biochemistry 410:234-243 (2011).
Almagro et al., "Humanization of Antibodies" Frontiers in Bioscience 13:1619-1633 (Jan. 1, 2008).
Anderson et al., "The Pivotal Role of the Complement System in Aging and Age-Related Macular Degeneration: Hypothesis Re-Visited" Progress in Retinal and Eye Research 29 29:95-112 (2010).
Avery et al., "Systemic Pharmacokinetics Following Intravitreal Injections of Ranibizumab, Bevacizumab or Aflibercept in Patients with Neovascular AMD" Br J Ophthalmol 98:1636-1641 (2014).
Badescu et al., "A New Reagent for Stable Thiol-Specific Conjugation" Bioconjugate Chemistry 25:460-469 (2014).
Buckmann et al., "Functionalization of Poly(ethylene Glycol) and Monomethoxy-Poly(ethylene Glycol)" Makromol. Chem. 182:1379-1384 (1981).
Carroll, "The Complement System in Regulation of Adaptive Immunity" Nature Immunology 5(10):981-986 (Oct. 2004).
Clackson et al., "Making antibody fragments using phage display libraries" Nature 352(6336):624-628 (Aug. 15, 1991).
Cui et al., "Noncoding Variant in the Complement Factor H Gene and Risk of Exudative Age-Related Macular Degeneration in a Chinese Population" Investigative Ophthalmology & Visual Science 51(2):1116-1120 (Feb. 2010).
Database Genebank (Apr. 24, 2001), 'Human Pro 1868 Protein' Database Accession No. AAB80272 XP002448361, dated Jun. 15, 2007.
Davies et al., "Affinity Improvement of Single Antibody VH Domains: Residues in All Three Hypervariable Regions Affect Antigen Binding" Immunotechnology 2(3):169-179 (Sep. 1996).
Davis et al., "Soluble, Nonantigenic Polyethylene Gylcol-Bound Enzymes" Biomedical Polymers: Polymeric Materials and Pharmaceuticals for Biomedical Use, Goldberg, E and Nakajima, A eds., New York: Academic Press pp. 441-452 (1980).
Dd SNP ss66926822 (http://www.ncbi.nlm.nih.gov/projects/SNP/snp_ss.cgi?subsnp_id=66926822, Nov. 14, 2006).

(56) References Cited

OTHER PUBLICATIONS

Durairaj et al., "Prediction of Vitreal Half-Life Based on Drug Physicochemical Properties: Quantitative Structure-Pharmacokinetic Relationships (QSPKR)" Pharmaceutical Research, Kluwer Academic Publishers—Plenum Publishers 26(5):1236-1260 (Oct. 8, 2008).
Ellman et al., "Biosynthetic method for introducing unnatural amino acids site-specifically into proteins" Meth Enzym 202:301-336 (1991).
Evans et al., "Harnessing the Information Contained within Genome-wide Association Studies to Improve Individual Prediction of Complex Disease Risk" Human Molecular Genetics 18(18):3525-3531 (2009).
Fitch et al., "Optimal Sequence Alignments" Proc. Natl. Acad. Sci. USA 80:1382-1386 (Mar. 1983).
Fung et al., "Pre-Neutralization of C5a-Mediated Effects by the Monoclonal Antibody 137-26 Reacting with the C5a Moiety of Native C5 without Preventing C5 Cleavage" Clin Exp Immunol 133:160-169 (2003).
Gagneux et al., "Genetic Differences between Humans and Great Apes" Molecular Phylogenetics and Evolution 18(1):2-13 (2001).
Gaudreault et al., "Preclinical pharmacokinetics of Ranibizumab (rhuFabV2) after a single intravitreal administration" Invest Ophthalmol Vis Sci. 46(2):726-33 (Feb. 2005).
Halushka et al., "Patterns of Single-Nucleotide Polymorphisms in Candidate Genes for Blood-Pressure Homeostasis" Nature Genetics 22:239-247 (Jul. 1999).
Harboe et al., "The Alternative Complement Pathway Revisited" J. Cell. Mol. Med. 12(4):1074-1084 (2008).
Hattersley et al., "What Makes a Good Genetic Association Study?" Lancet 366:1315-1323 (Oct. 8, 2005).
Holt et al., "Domain antibodies: proteins for therapy" Trends Biotechnol. 21(11):484-490 (Nov. 2003).
Humphreys et al., "Alternative Antibody Fab' Fragment PEGylation Strategies: Combination of Strong Reducing Agents, Disruption of the Interchain Disulphide Bond and Disulphide Engineering" Protein Engineering, Design & Selection 20(5):227-234 (2007).
International Preliminary Report on Patentability for PCT/US2015/028641 dated Nov. 1, 2016 (8 pages).
International Search Report for PCT/US2015/028641 (8 pages).
International Search Report for PCT/US2016/059179 (8 pages).
Jevsevar et al., "PEGylation of antibody fragments for half-life extension" Methods in Molecular Biology 901:233-246 (Jan. 1, 2012).
Kabat et al. Sequences of Proteins of Immunological Interest "Table of Contents" 5th edition, Bethesda, MD: Public Health Service, vol. 1 (1991).
Katre, "The Conjugation of Proteins with Polyethylene Glycol and other Polymers. Altering properties of proteins to enhance their therapeutic potential." Advanced Drug Delivery Reviews 10(1):91-114 (1993).
Khalili et al., "Fab-PEG-Fab as a Potential Antibody Mimetic" Bioconjugate Chemistry 24(11):1870-1882 (Sep. 27, 2013).
Kindt et al. Kuby Immunology "Antigens and Antibodies Chapter 4" 6th edition, N.Y.:W.H. Freeman and Co: p. 91 (2007).
Kunkel, "Rapid and Efficient Site-Specific Mutagenesis Without Phenotypic Selection" Proc. Natl. Acad. Sci.:488-492 (Jan. 1985).
Le et al., "A Mechanistic Pharmacokinetic/Pharmacodynamic Model of Factor D Inhibition in Cynomolgus Monkeys by Lampalizumab for the Treatment of Geographic Atrophy" Journal of Pharmacology and Experimental Therapeutics 355:288-296 (Nov. 2015).
Lewis et al., "Maleimidocysteineamido-DOTA derivatives: New reagents for radiometal chelate conjugation to antibody sulfhydryl groups undergo pH-dependent cleavage reactions" Bioconj Chem 9:72-86 (1998).
Lucentini, "Gene Association Studies Typically Wrong" The Scientist 24(2876):20 (2004).
Maynard et al., "Antibody Engineering" Annu. Rev. Biomed. Eng. 02:339-76 (2000).
NCBI dbSNP Database (rs4698775, ss70817155. Apr. 20, 2007. National Center for Biotechnology Information, National Library of Medicine (Bethesda, MD, USA)).
Needleman et al., "A General Method Applicable to the Search for Similarities in the Amino Acid Sequence of Two Proteins" J. Mol. Biol. 48:443-453 (1970).
Noren et al., "A general method for site-specific incorporation of unnatural amino acids into proteins" Science 244(4901):182-188 (Apr. 14, 1989).
Nozaki et al., "Drusen Complement Components C3a and C5a Promote Choroidal Neovascularization" PNAS 103(7):2328-2333 (Feb. 14, 2006).
Patel et al., "Ocular Drug Delivery Systems: An Overview" World J Pharmacol. 2(2):47-64 (2013).
Patterson et al., "Improving the Serum Stability of Site-Specific Antibody Conjugates with Sulfone Linkers" Bioconjugate Chemistry 25:1402-1407 (2014).
Pearlman et al. Peptide and Protein Drug Delivery "Chapter 6, Analysis of Protein Drugs" Vincent H.L. Lee, Marcel Dekker, Inc.,:247-301 (1991).
Pini et al., "Design and Use of a Phage Display Library" The Journal of Biological Chemistry 273:21769-21776 (1998).
Portolano et al., "Lack of promiscuity in autoantigen-specific H and L chain combinations as revealed by human H and L chain 'roulette'" J Immunol 150(3):880-7 (Feb. 1, 1993).
Presta et al., "Humanization of an antibody directed against IgE" J. Immunol. 151(5):2623-2632 (Sep. 1, 1993).
Rattner et al., "Macular Degeneration: Recent Advances and Therapeutic Opportunities" Nature 7:860-872 (Nov. 2006).
Remington's Pharmaceutical Sciences (Table of Contents), Oslo, 16th edition, Easton, PA:Mack Publishing Company:TOC (1980).
Ryan et al., "Advances in PEGylation of Important Biotech Molecules: Delivery Aspects" Expert Opinion on Drug Delivery 5(4):371-383 (2008).
Tedeschi-Blok et al., "Population-Based Study of Early Age-Related Macular Degeneration; Role of the Complement Factor H Y402H Polymorphism in Bilateral but not Unilateral Disease" Ophthalmology 114(1):99-103 (Jan. 2007).
Teo et al., "A Genotype Calling Algorithm for the Illumina BeadArray Platform" Bioinformatics 23(20):2741-2746 (2007).
Vugmeyster et al., "Pharmacokinetic, biodistribution, and biophysical profiles of TNF nanobodies conjugated to linear or branched poly(ethylene glycol)" Bioconjugate Chemistry 23(7):1454-1462 (Jul. 18, 2012).
Wang et al., "Age-Related Macular Degeneration Susceptibility Genes in an Older Australian Population: Comparison of Distributions and Clinical Significance of Two Major Genes with Other Known Genes (Abstract)" Investigative Ophthalmology & Visual Science 53:1-3 (Mar. 2012).
Wang et al., "Antibody Structure, Instability, and Formulation" J. of Pharmaceutical Sciences 96(1):1-26 (2007).
Weber et al., "The Role of the Complement System in Age-Related Macular Degeneration" Deutsches Arzteblatt International 111(8):133-138 (2014).
Written Opinion for PCT/US2015/028641 (7 pages).
Xu et al., "Diversity in the CDR3 region of V(H) is sufficient for most antibody specificities" Immunity 13(1):37-45 (Jul. 2000).
BLAST Report Q80WA3, http://expasy.org/cgi-bininiceprot.pl/printable?ac-Q80WA3, dated.Mar. 1, 2004, retrieved Aug. 26, 2008 (2 pages).
Database dbSNP—NCBI No. rs17792825, retrieved Jan. 10, 2017 (1 page).
Database dbSNP—NCBI No. ss6697713, retrieved Aug. 29, 2016 (2 pages).
Database dbSNP—NCBI No. ss67486158, retrieved Aug. 29, 2016 (2 pages).
Database dbSNP—NCBI No. ss67520449, retrieved Nov. 21, 2015 (2 pages).
Hutanu et al., "Recent Applications of Polyethylene Glycols (PEGs) and PEG Derivatives" Modern Chemistry & Applications 2(2):1-6 (2014).

(56) References Cited

OTHER PUBLICATIONS

Johnson et al. Methods in Molecular Biology: Antibody Engineering: Methods and Protocols "2: The Kabat Database and a Bioinformatics Example" Lo, Totowa, NJ: Humana Press, vol. 248:1-25 (2004).

Tesar et al., "Protein Engineering to Increase the Potential of a Therapeutic Antibody Fab for Long-Acting Delivery to the Eye" mABs 9(8):1297-1305 (Aug. 30, 2017).

Haberger et al., "Assessment of chemical modifications of sites in the CDRs of recombinant antibodies: Susceptibility vs. functionality of critical quality attributes," Mabs, 6(2):327-339 (2014).

\* cited by examiner

WT Light Chain

```
DIQVTQSPSS LSASVGDRVT ITCITSTDID DDMNWYQQKP GKVPKLLISG GNTLRPGVPS    60
RFSGSGSGTD FTLTISSLQP EDVATYYCLQ SDSLPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC       (SEQ ID NO:1)           214
```

WT Heavy Chain

```
EVQLVQSGPE LKKPGASVKV SCKASGYTFT NYGMNWVRQA PGQGLEWMGW INTYTGETTY    60
ADDFKGRFVF SLDTSVSTAY LQISSLKAED TAVYYCEREG GVNNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THT  (SEQ ID NO:2)      223
```

FIG. 1A

VL Domain

| | |
|---|---|
| WT | DIQVTQSPSSLSASVGDRVTITCIISTDIDDDMNWYQQKPGKVPKLLISGGNTLRPGVPSRFSGSGSGTDFTLTISSLQP |
| TM | DIQVTQSPSSLSASVGDRVTITCIISTDIESDMNWYQQKPGKVPKLLISGGNTLRPGVPSRFSGSGSGTDFTLTISSLQP |
| TM.D92E | DIQVTQSPSSLSASVGDRVTITCIISTDIESDMNWYQQKPGKVPKLLISGGNTLRPGVPSRFSGSGSGTDFTLTISSLQP |
| SIESD | DIQVTQSPSSLSASVGDRVTITCIISTSIESDMNWYQQKPGKVPKLLISGGNTLRPGVPSRFSGSGSGTDFTLTISSLQP |
| SIESD.N103S | DIQVTQSPSSLSASVGDRVTITCIISTSIESDMNWYQQKPGKVPKLLISGGNTLRPGVPSRFSGSGSGTDFTLTISSLQP |

| | | |
|---|---|---|
| WT | EDVATYYCLQSDSLPYTFGQGTKVEIK | (SEQ ID NO:3) |
| TM | EDVATYYCLQSDSLPYTFGQGTKVEIK | (SEQ ID NO:16) |
| TM.D92E | EDVATYYCLQSESLPYTFGQGTKVEIK | (SEQ ID NO:18) |
| SIESD | EDVATYYCLQSDSLPYTFGQGTKVEIK | (SEQ ID NO:19) |
| SIESD.N103S | EDVATYYCLQSDSLPYTFGQGTKVEIK | (SEQ ID NO:19) |

VH Domain

| | |
|---|---|
| WT | EVQLVQSGPELKKPGASVKVSCKASGYTFTNYGMNWVRQAPGQGLEWMGWINTYTGETTYADDFKGRFVFSLDTSVSTAY |
| TM | EVQLVQSGPELKKPGASVKVSCKASGYTFTNYGMNWVRQAPGQGLEWMGWINTYTGETTYAEDFKGRFVFSLDTSVSTAY |
| TM.D92E | EVQLVQSGPELKKPGASVKVSCKASGYTFTNYGMNWVRQAPGQGLEWMGWINTYTGETTYAEDFKGRFVFSLDTSVSTAY |
| SIESD | EVQLVQSGPELKKPGASVKVSCKASGYTFTNYGMNWVRQAPGQGLEWMGWINTYTGETTYAEDFKGRFVFSLDTSVSTAY |
| SIESD.N103S | EVQLVQSGPELKKPGASVKVSCKASGYTFTNYGMNWVRQAPGQGLEWMGWINTYTGETTYAEDFKGRFVFSLDTSVSTAY |

| | | |
|---|---|---|
| WT | LQISSLKAEDTAVYYCEREGGVNNWGQGTLVTVSS | (SEQ ID NO:4) |
| TM | LQISSLKAEDTAVYYCEREGGVNNWGQGTLVTVSS | (SEQ ID NO:17) |
| TM.D92E | LQISSLKAEDTAVYYCEREGGVNNWGQGTLVTVSS | (SEQ ID NO:17) |
| SIESD | LQISSLKAEDTAVYYCEREGGVNNWGQGTLVTVSS | (SEQ ID NO:17) |
| SIESD.N103S | LQISSLKAEDTAVYYCEREGGVSNWGQGTLVTVSS | (SEQ ID NO:20) |

*FIG. 1B*

SIESD (AFD.v8) Light Chain

```
DIQVTQSPSS LSASVGDRVT ITCIITSTSIE SDMNWYQQKP GKVPKLLISG GNTLRPGVPS    60
RFSGSGSGTD FTLTISSLQP EDVATYYCLQ SDSLPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC       (SEQ ID NO:26)          214
```

SIESD (AFD.v8) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVNNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THT        (SEQ ID NO:27)  223
```

Cys-Modified SIESD (AFD.v8) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVNNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTC       (SEQ ID NO:30)  223
```

Cys-Pro-Pro-Cys-Modified SIESD (AFD.v8) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVNNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPC    (SEQ ID NO:31)  223
```

FIG. 1C

SIESD.N103S (AFD.v14) Light Chain

```
DIQVTQSPSS LSASVGDRVT ITCITSTSIE SDMNWYQQKP GKVPKLLISG GNTLRPGVPS    60
RFSGSGSGTD FTLTISSLQP EDVATYYCLQ SDSLPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC      (SEQ ID NO:28)          214
```

SIESD.N103S (AFD.v14) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVSNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THT      (SEQ ID NO:29) 223
```

Cys-Modified SIESD.N103S (AFD.v14) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVSNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTC      (SEQ ID NO:32) 223
```

Cys-Modified SIESD.N103S (AFD.v14) Heavy Chain

```
EVQLVQSGPE LKKPGASVKV SCKASGYTFT NYGMNWVRQA PGQGLEWMGW INTYTGETTY    60
AEDFKGRFVF SLDTSVSTAY LQISSLKAED TAVYYCEREG GVSNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THTCPPC  (SEQ ID NO:33) 223
```

*FIG. 1D*

Protein Solutions in PBS Buffer

SIESD (AFD.v8)   SIESD.N103S (AFD.v14)   aFD WT

FIG. 8

Concentration Dependence of Viscosity for AFD Variants in pH 5.5 Buffer

- △ aFD WT
- ● SIESD (AFD.v8)
- ■ SIESD.N103S (AFD.v14)

*FIG. 11*

ANTI-FACTOR D ANTIBODIES

CROSS REFERENCE TO RELATED APPLICATIONS

This application claims priority to U.S. Provisional application No. 61/987,298, filed May 1, 2014, and U.S. Provisional Application No. 62/076,372, filed Nov. 6, 2014, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 27, 2015, is named P05826-US_SL.txt and is 30,764 bytes in size.

BACKGROUND OF THE INVENTION

The development of therapeutic antibodies represents a revolutionary era in the long history of human medicine. More than 30 antibodies have been approved for human therapy, and over 250 antibodies are in clinical development worldwide for a wide range of major diseases, including cancer, autoimmunity, inflammation, cardiovascular disease, infectious diseases and ocular disease. Over the past decade, the market for monoclonal antibody products has grown exponentially, propelled by the success of such blockbuster drugs as trastuzumab, bevacizumab, rituximab, infliximab and adalimumab. While these first-generation antibody therapeutics have benefited numerous patients, advances in antibody technology and a deeper understanding of the mechanism of action have paved the way for improved versions of antibodies with even better efficacy and less side effects.

Successful development and viable use of antibody therapeutics pose many unique challenges comparing to traditional medicines that are small organic and inorganic molecules. The biophysical properties of antibodies, like all proteins, are important determinants of their behavior and have significant impacts for development of therapeutics relating to expression, purification, formulation, storage, delivery, pharmacokinetics, immunogenicity and dosing regimens. Among the many characteristics, protein stability is a main feature defining the quality of a candidate antibody and its desirability as a successful therapeutic.

Protein therapy often requires delivering high dose of the protein to patients in order to achieve the desired efficacy. Meanwhile, certain routes of administration are associated with limitations such as delivery time, volume and physical force that require the high dose protein to be in a high-concentration formulation (e.g., at least 100 mg/ml). However, highly concentrated protein formulations pose particular challenges with respect to stability, solubility, viscosity and other protein properties.

Proteins can be unstable and become degraded via multiple physical and chemical degradation pathways. Physical instability occurs mainly via two pathways—denaturation and aggregation, whereas chemical instability can occur via many pathways, such as deamidation, isomerization, cross-linking, oxidation, and fragmentation. Antibody instability is undesirable for drug development, as it can lead to decreased amount of active drug and lower in vivo efficacy, increased variability among batches of the therapeutics, and perhaps most importantly, immunogenicity in patients against aggregates and degradants. Wang et al (2007) *J. Pharm. Sci.* 96:1-26; Moore et al (1980) *J Clin Endocrinology & Metabolism* 51: 691-697; Rosenberg et al (2006) AAPSJ 8:E501-7; Joubert et al (2011) *J Biol Chem* 286: 25118-25133; Joubert et al (2012) *J Biol Chem*(2012) 286:25266-79).

Antibodies are large multidomain proteins, and factors contributing to their stability and propensity to aggregate are complex, including many extrinsic conditions such as temperature, pH, concentration, ionic strength and physical stress. Equally critical is the protein's own primary sequence. Although by nature the Fc region is largely identical between antibodies of a particular isotype, the Fab region differs greatly. Thus, there are significant variations in stability and aggregation propensity between antibodies, largely due to Fab sequence differences and the particular antigen specificity of the antibody. Lowe et al. (2011) *Adv. Protein Chem. Struct Biol.* 84:41-61.

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses two distinct activation pathways, designated the classical and the alternative pathways (V. M. Holers In *Clinical Immunology: Principles and Practice*, ed. R. R. Rich, Mosby Press; 1996, 363-391). The classical pathway is a calcium/magnesium-dependent cascade which is normally activated by the formation of antigen-antibody complexes. The alternative pathway is a magnesium-dependent cascade which is activated by deposition and activation of C3 on certain susceptible surfaces (e.g. cell wall polysaccharides of yeast and bacteria, and certain biopolymer materials). Activation of the complement pathway generates biologically active fragments of complement proteins, e.g. C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 µg/ml), and it has been shown to be the limiting enzyme for activation of the alternative complement pathway (P. H. Lesavre and H. J. Müller-Eberhard. (1978) *J. Exp. Med.* 148: 1498-1510; J. E. Volanakis et al. (1985) *New Eng. J. Med.* 312: 395-401).

The down-regulation of complement activation has been demonstrated to be effective in treating several disease indications in animal models and in ex vivo studies, e.g. systemic lupus erythematosus and glomerulonephritis, rheumatoid arthritis, cardiopulmonary bypass and hemodialysis, hyperacute rejection in organ transplantation, myocardial infarction, reperfusion injury, and adult respiratory distress syndrome. In addition, other inflammatory conditions and autoimmune/immune complex diseases are also closely associated with complement activation, including thermal injury, severe asthma, anaphylactic shock, bowel inflammation, urticaria, angioedema, vasculitis, multiple sclerosis, myasthenia gravis, membranoproliferative glomerulonephritis, and Sjögren's syndrome.

Age-related macular degeneration (AMD) is a progressive chronic disease of the central retina with significant consequences for visual acuity. Lim et al. (2012) *Lancet* 379:1728. Late forms of the disease are the leading cause of vision loss in industrialized countries. For the Caucasian population ≥40 years of age the prevalence of early AMD is estimated at 6.8% and advanced AMD at 1.5%. de Jong (2006) *N. Engl. J. Med.* 355: 1474. The prevalence of late AMD increases dramatically with age rising to 11.8% after 80 years of age. Two types of AMD exist, non-exudative (dry) and exudative (wet) AMD. The more common dry form AMD involves atrophic and hypertrophic changes in the retinal pigment epithelium (RPE) underlying the central retina (macula) as well as deposits (drusen) on the RPE. Advanced dry AMD can result in significant retinal damage, including geographic atrophy (GA), with irreversible vision loss. Moreover, patients with dry AMD can progress to the wet form, in which abnormal blood vessels called choroidal neovascular membranes (CNVMs) develop under the retina, leak fluid and blood, and ultimately cause a blinding disciform scar in and under the retina.

Drugs targeting new blood vessel formation (neovascularization) have been the mainstay for treating wet AMD. Ranibizumab, which is an anti-VEGFA antibody fragment, has proven to be highly effective in improving vision for patients afflicted with wet AMD. Recent studies have implicated an association between AMD and key proteins in the complement cascade and a number of therapies targeting specific complement components are being developed to treat dry AMD. A humanized anti-Factor D Fab fragment (aFD, lampalizumab; FCFD4514S) that potently inhibits Factor D and the alternative complement pathway, through binding to an exosite on factor D is currently in clinical development for the treatment of GA associated with dry AMD. Katschke et al. (2012) *J. Biol. Chem.* 287:12886. A recent phase II clinical trial has shown that monthly intravitreal injection of lampalizumab effectively slowed the progression of GA lesions in patients with advanced dry AMD.

Eyes have many unique biophysical and anatomic features that make the ocular drug delivery more challenging. For example, blood-ocular barriers are defense mechanisms for protect the eye from infection, but at the same time make it hard for drug to penetrate, especially for diseases in the posterior segments of the eye. Consequently, high-dose administration is often desired to achieve and maintain drug's onsite bioavailability (e.g., ocular residence time) in order to improve efficacy. Meanwhile, the limited space in the back of the eye restrains the drug volume to be delivered, which in turn demands drugs to be delivered in a high concentration formulation.

Patients with ocular diseases can also be benefited from long acting/slow released delivery of therapeutics. Less frequent dosing would provide improved convenience to the patient, have potential benefits of decreased infection rate and increased clinical efficacy. Controlled release of high dose drugs could also minimize drug side effects. Two promising systems for long-acting delivery are PLGA-based solid implants and an implantable port delivery system (PDS). Both systems have the potential to provide near zero-order release kinetics for an extended period of time. For PLGA implants the protein drug is encapsulated in a hydrophobic polymer matrix and drug release is accomplished via slow hydrolysis of the polymer. The rate of release can be controlled by changing the drug loading, polymer hydrophobicity, or polymer molecular weight. The PDS is a refillable device where release into the vitreous is controlled by a porous metal membrane comprising a titanium frit. Since the reservoir has a low volume, a high protein concentration is required for effective delivery with the PDS.

In addition to or in lieu of high concentration and long acting delivery, increased bioavailability (e.g., ocular residence time) of the drug can be achieved, or facilitated, by post-translational modifications, wherein the protein drug is covalently conjugated with natural or synthetic polymers such as polysialylation, HESylation (conjugation with hydroxyethyl starch) and PEGylation. Chen et al (2011) Expert. Opin. Drug Deliv. 8:1221-36; Kontermann (2009) BioDrugs 23:93-109. PEGylation, the covalent attachment of polymer polyethylene glycol (PEG) to a protein, is a well-established technology especially useful for extending the half-life of antibody fragment therapeutics. Jevsevar et al. (2010) *Biotech. J.* 5:113-128.

The conditions that a drug is exposed to vary depending on the delivery system used. For incorporation into solid PLGA implants, lyophilized or spray-dried drug is used. Implants are produced using a hot-melt extrusion process such that the drug is briefly exposed to temperatures approaching 90° C. Although the drug remains in solid state for the duration of release, degradation of PLGA may expose the drug to a low pH environment. In contrast, drug delivered with the PDS is maintained at high concentration in liquid state and exposed to vitreous which is characterized as a reducing environment at physiological ionic strength and pH.

Thus, there exists great needs for anti-factor D antibodies with improved stabilities, preferably suitable for high concentration formulation and/or long acting delivery.

SUMMARY OF THE INVENTION

The present invention is based in part on the discovery that targeted amino acid substitutions of identified hot spots in an antibody can effectively improve the antibody's stability and overall potency as a therapeutic.

In one aspect, the present invention relates to anti-factor D antibody variants with improved stability. The invention includes anti-factor D antibody variants comprising substitution of at least one target aspartic acid (D or Asp) residue within a hypervariable region (HVR) of a reference anti-Factor D antibody, wherein the target Asp residue is identified as prone to isomerization and the substitution is Asp to Glutamic acid (E or Glu), and wherein the anti-Factor D antibody variant exhibits improved stability without significant loss of Factor D binding affinity when compared to the reference anti-Factor D antibody. In some aspects, the target Asp residue subject to substitution is within an Asp-Xaa motif, wherein Xaa is Asp, Gly, His, Ser or Thr. In one aspect, the target Asp residue is the first Asp of an Asp-Asp (DD) motif In one aspect, the anti-factor D antibody variants comprise one or more substitutions at additional Asp sites within a HVR of a reference anti-Factor D antibody, wherein the substitution is Asp to Serine (S or Ser) in order to reduce the overall charges of the antibody, thereby improving the solubility of the antibody. In one aspect, the anti-factor D antibody variants comprise one or more substitutions at asparagine (N or Asn) sites identified as prone to deamidation, wherein the substitution is Asn to Ser in order to reduce or eliminate the antibody's deamidation.

In one aspect, the reference anti-factor D antibody used to generate the antibody variants of the invention comprises the light chain variable domain sequence of SEQ ID NO:3, the heavy chain variable domain sequence of SEQ ID NO:4, or both. Subsequently, the resulting antibody variants may comprise a light chain HVR1 (HVR-L1) sequence of SEQ ID NO:11 and a heavy chain HVR2 (HVR-H2) sequence of SEQ ID NO:12, or may comprise a light chain HVR3 (HVR-L3) sequence of SEQ ID NO:13, or may comprise a light chain HVR1 (HVR-L1) sequence of SEQ ID NO:14 and a heavy chain HVR2 (HVR-H2) sequence of SEQ ID NO:12, or may comprise a heavy chain HVR3 (HVR-H3) sequence of SEQ ID NO:15.

In one aspect, the anti-factor D antibody variant of the invention is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:11 and a heavy chain HVR2 (HVR-H2) sequence of SEQ ID NO:12. Such variant is referred to as the "TM" variant (AFD.v6) in Examples herein below (see, e.g., Table 1).

In one aspect, the anti-factor D antibody variant of the invention is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:11, a heavy chain HVR2 (HVR-H2) sequence of SEQ ID NO:12 and a light chain HVR3 (HVR-L3) sequence of SEQ ID NO:13. Such variant is referred to as the "TM.D92E" variant (AFD.v7) in Examples herein below (see, e.g., Table 1).

In one aspect, the anti-factor D antibody variant of the invention is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:14 and a heavy chain HVR2 (HVR-H2) sequence of SEQ ID NO:12. Such variant is referred to as the "SIESD" variant (AFD.v8) in Examples herein below (see, e.g., Table 1). In one embodiment, the "SIESD" variant (AFD.v8) comprises the light chain sequence of SEQ ID NO: 26 and the heavy chain sequence of SEQ ID NO: 27. In one embodiment, a Cys-modified version of the "SIESD" variant comprises the heavy chain sequence of SEQ ID NO: 30. In one embodiment, a Cys-Pro-Pro-Cys-modified version of the "SIESD" variant comprises the heavy chain sequence of SEQ ID NO: 31.

In one aspect, the anti-factor D antibody variant of the invention is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:14, a heavy chain HVR2 (HVR-H2) sequence of SEQ ID NO:12 and a heavy chain HVR3 (HVR-H3) sequence of SEQ ID NO:15. Such variant is referred to as the "SIESD.N103S" variant (AFD.v14) in Examples herein below (see, e.g., Table 1). In one embodiment, the "SIESD.N103S" variant (AFD.v14) comprises the light chain sequence of SEQ ID NO: 28 and the heavy chain sequence of SEQ ID NO: 29. In one embodiment, a Cys-modified version of the "SIESD.N103S" variant comprises the heavy chain sequence of SEQ ID NO: 32. In one embodiment, a Cys-Pro-Pro-Cys-modified version of the "SIESD" variant comprises the heavy chain sequence of SEQ ID NO: 33.

In one aspect, the present invention relates to anti-Factor D antibody variants comprising one or more substitutions within the HVRs of a reference anti-Factor D antibody. In one aspect, the reference anti-Factor D antibody comprised the following HVR sequences:

```
HVR-L1:
                                    (SEQ ID NO: 5)
ITSTDIDDDMN;

HVR-L2:
                                    (SEQ ID NO: 6)
GGNTLRP;

HVR-L3:
                                    (SEQ ID NO: 7)
LQSDSLPYT;

HVR-H1:
                                    (SEQ ID NO: 8)
GYTFTNYGMN;

HVR-H2:
                                    (SEQ ID NO: 9)
WINTYTGETTYADDFKG;
and

HVR-H3:
                                    (SEQ ID NO: 10)
EGGVNN.
```

And the corresponding variants comprise one or more of the following substitutions:
(a) D5S in SEQ ID NO: 5;
(b) D7E in SEQ ID NO: 5;
(c) D8S in SEQ ID NO: 5 (a, b, and c disclosed in SEQ ID NO: 22);
(d) D13E in SEQ ID NO: 9 (SEQ ID NO: 23);
(e) D4E in SEQ ID NO: 7 (SEQ ID NO: 24); or
(f) N5S in SEQ ID NO: 10 (SEQ ID NO: 25).

In one aspect, the variant of the present invention combines the substitutions (b)-(d) above. In another aspect, the variant combines the substitutions (b)-(e) above. In another aspect, the variant combines the substitutions (a)-(d) above. In another aspect, the variant combines the substitutions (a)-(d) and (f) above.

In one aspect, the present invention relates to an anti-Factor D antibody comprising a light chain variable domain amino acid sequence of SEQ ID NO:16, 18 or 19. In another aspect, the present invention relates to an anti-Factor D antibody comprising a heavy chain variable domain amino acid sequence of SEQ ID NO:17 or 20. In another aspect, the anti-Factor D antibody comprises a light chain variable domain amino acid sequence of SEQ ID NO:16, 18 or 19 and a heavy chain variable domain amino acid sequence of SEQ ID NO:17 or 20. For example, the anti-Factor D antibody can be the "TM" variant (AFD.v6) that comprises the light chain variable domain amino acid sequence of SEQ ID NO:16 and the heavy chain variable domain amino acid sequence of SEQ ID NO:17; the "TM.D92E" variant (AFD.v7) that comprises the light chain variable domain amino acid sequence of SEQ ID NO:18 and the heavy chain variable domain amino acid sequence of SEQ ID NO:17; the "SIESD" variant (AFD.v8) that comprises the light chain variable domain amino acid sequence of SEQ ID NO:19 and the heavy chain variable domain amino acid sequence of SEQ ID NO:17; or the "SIESD.N103S" variant (AFD.v14) that comprises the light chain variable domain amino acid sequence of SEQ ID NO:19 and the heavy chain variable domain amino acid sequence of SEQ ID NO:20.

In one aspect, the present invention relates to an anti-Factor D antibody having a variable light chain comprising a HVR-L1 having the sequence of SEQ ID NO:11 or 14, a HVR-L2 having the sequence of SEQ ID NO:6, and a HVR-L3 having the sequence of SEQ ID NO:7 or 13; and a variable heavy chain comprising a HVR-H1 having the sequence of SEQ ID NO:8, a HVR-H2 having the sequence of SEQ ID NO:9 or 12, and a HVR-H3 having the sequence of SEQ ID NO:10 or 15. For example, the anti-Factor D antibody can be the "SIESD" variant (AFD.v8) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:10); or the "SIESD.N103S" variant (AFD.v14) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:15).

In one aspect, the present invention relates to anti-Factor D antibody variants with no detectable Asp isomerization made by a method for removing or reducing isomerization, comprising: (a) identifying one or more Asp residues prone to Asp isomerization within HVRs of a reference anti-Factor D antibody; (b) substituting Glu for the Asp residue identified in step (a); (c) screening the resulting candidate variants for Asp isomerization; and (d) selecting those variants that have no detectable Asp isomerization. In one aspect, the method above is combined with a method for removing or reducing deamidation, comprising (a) identifying one or more Asn residues prone to deamidation within HVRs of the reference anti-Factor D antibody; (b) substituting Ser for the Asn residue identified in step (a); (c) screening the resulting candidate variants for deamidation; and (d) selecting those variants having reduced or eliminated deamidation. In another aspect, the method for removing or reducing isomerization is combined with a method for reducing overall charge of the antibody by: (a) selecting one or more negatively charged amino acid residues D or E within HVRs of the reference anti-Factor D antibody; (b) substituting Ser for the residue selected in step (a); (c) screening the resulting candidate variants for solubility; and (d) selecting those variants having improved solubility when compared to the reference anti-Factor D antibody.

In one aspect, the anti-factor D antibody variants of the present invention have improved stability while maintaining the factor D binding affinity when compared to the reference anti-factor D antibody. In one aspect, antibodies of the present invention bind to Factor D with a binding affinity of at least about $10^{-9}$ to $10^{-12}$ M. In one aspect, the antibodies of the present invention include human, humanized or chimeric antibodies.

In one aspect, the antibodies of the present invention are antibody fragments (e.g. antigen-binding fragments). The antibody fragments of the present invention may, for example, be Fab, Fab', F(ab')$_2$, scFv, (scFv)$_2$, dAb, complementarity determining region (CDR) fragments, linear antibodies, single-chain antibody molecules, minibodies, diabodies, or multispecific antibodies formed from antibody fragments.

In other aspects of the invention, the present invention includes compositions comprising an antibody of the invention. In another aspect, the invention concerns a composition of matter comprising an antibody of the invention, as described herein, in combination with a carrier. Optionally, the carrier is a pharmaceutically acceptable carrier.

In one aspect, the present invention includes pharmaceutical formulations comprising the antibody or antibody variants described above, at therapeutically effective concentrations. In some aspects, the pharmaceutical formulation comprises the antibody or antibody variant at a concentration of at least 100 mg/ml, between 100-150 mg/ml, between 100-200 mg/ml, between 100-300 mg/ml, between 100-400 mg/ml, between 100-500 mg/ml; at least 200 mg/ml, at least 300 mg/ml, at least 400 mg/ml or at least 500 mg/ml. In some aspects, the concentration of the antibody or antibody variant in the formulation is about 200, 250, 300, 350, 400, 450 or 500 mg/ml. In one aspect, the concentration of the antibody or antibody variant in the formulation is less than 450 mg/ml.

Another aspect of the present invention is the use of the antibody of the invention for treatment of disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. In another embodiment, complement activation is also associated with transplant rejection. In another embodiment, complement activation is also associated with ocular diseases (all ocular conditions and diseases the pathology of which involve complement, including the classical and the alternative pathway of complement), such as, for example, without limitation, macular degenerative disease, such as all stages of age-related macular degeneration (AMD), including dry and wet (non-exudative and exudative) forms, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions include age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In another example, complement-associated eye conditions include age-related macular degeneration (AMD), including early AMD (e.g. includes multiple small to one or more non-extensive medium sized drusen), intermediate AMD (e.g. includes extensive medium drusen to one or more large drusen) and advanced AMD (e.g. includes geographic atrophy or advanced wet AMD (CNV). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, the complement-associated eye condition is intermediate dry AMD. In one example, the complement-associated eye condition is geographic atrophy. In one example, the complement-associated eye condition is wet AMD (choroidal neovascularization (CNV)).

In another aspect, the invention provides a kit, comprising an antibody of the invention. In one embodiment, the invention provides a kit, comprising an antibody of the invention and instructions for use. In one embodiment, the invention concerns a kit comprising an antibody of the invention and instructions for administering said antibody, to treat a complement-associated disorder. In one embodiment, the invention provides a kit comprising a first container comprising a composition comprising one or more one or more antibodies of the invention; and a second container comprising a buffer. In one embodiment, the buffer is pharmaceutically acceptable. In one embodiment, a composition comprising an antibody of the invention further comprises a carrier, which in some embodiments is pharmaceutically acceptable. In one embodiment, a kit further comprises instructions for administering the composition (e.g the antibody, or antibody fragment thereof (e.g. antigen-binding fragment) to a subject. In one embodiment, a kit further comprises instructions for use of the kit.

In one aspect, the invention concerns an article of manufacture containing materials useful for the treatment, prevention and/or diagnosis of complement-associated disorders. In one embodiment, the invention concerns an article of manufacture, comprising: (a) a container; (b) a label on the container; and (c) a composition of matter comprising an antibody of the present invention, contained with the container, wherein the label on said container indicates that the composition can be used for treatment, prevention and/or diagnosis of complement-associated disorders.

In one aspect, the invention provides use of an anti-Factor D antibody of the invention in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In one aspect, the invention provides use of an article of manufacture of the invention in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In one aspect, the invention provides use of a kit of the invention in the preparation of a medicament for the therapeutic and/or prophylactic treatment of a disease, such as a complement-associated eye condition. In one embodiment, the complement-associated eye condition is selected from age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In one aspect, the invention provides a Factor D antagonist and a HTRA1 antagonist. In one embodiment, the Factor D antagonist is an anti-Factor D antibody. In a further embodiment, the anti-Factor D antibody is an anti-Factor D antibody variant described herein. In one embodiment the HTRA1 antagonist is an anti-HTRA1 antibody.

In one aspect, the treatment of disorders associated with excessive or uncontrolled complement activation in a human subject with a disorder associated with excessive or uncontrolled complement activation comprises administering to the subject an effective amount of an therapeutic compound, such as a Factor D antagonist, and further comprises administering to the subject an effective amount of a second therapeutic compound, such as a HTRA1 antagonist. In one embodiment, the Factor D antagonist is an anti-Factor D antibody. In one embodiment, the anti-Factor D antibody is an anti-Factor D antibody variant described herein. In one embodiment, the HTRA1 antagonist is an anti-HTRA1 antibody. In one embodiment, the Factor D antagonist is an anti-Factor D antibody and the HTRA1 antagonist is an anti-HTRA1 antibody.

In one aspect, the administration of the Factor D antagonist and any second therapeutic compound can be done simultaneously, e.g., as a single composition or as two or more distinct compositions using the same or different administration routes. Alternatively, or additionally the administration can be done sequentially, in any order.

BRIEF DESCRIPTION OF THE FIGURES

FIG. 1 shows amino acid sequences of a reference anti-factor D antibody WT (aFD WT) and its select variants (1A: light chain and heavy chain sequences (SEQ ID NO: 1 and 2, respectively) of WT; 1B: alignment of light chain variable domains of WT, TM, TM.92E, SIESD and SIESD.N103S (SEQ ID NOs: 3, 16, 18, 19 and 19, respectively) and heavy chain variable domains of WT, TM, TM.92E, SIESD and SIESD.N103S (SEQ ID NOs: 4, 17, 17, 17 and 20, respectively); 1C: light and heavy chain sequences (SEQ ID NOs: 26 and 27, respectively) of SIESD (AFD.v8); 1D: light and heavy chain sequences (SEQ ID NOs: 30 and 31, respectively) of SIESD.N103S (AFD.v14)). HVRs within the variable domains are underlined. Residue substitutions in the variants are shown in bold. Cys and Cys-Pro-Pro-Cys (SEQ ID NO: 21) modifications are shown in italics in FIGS. 1C and 1D.

Figure 3A:
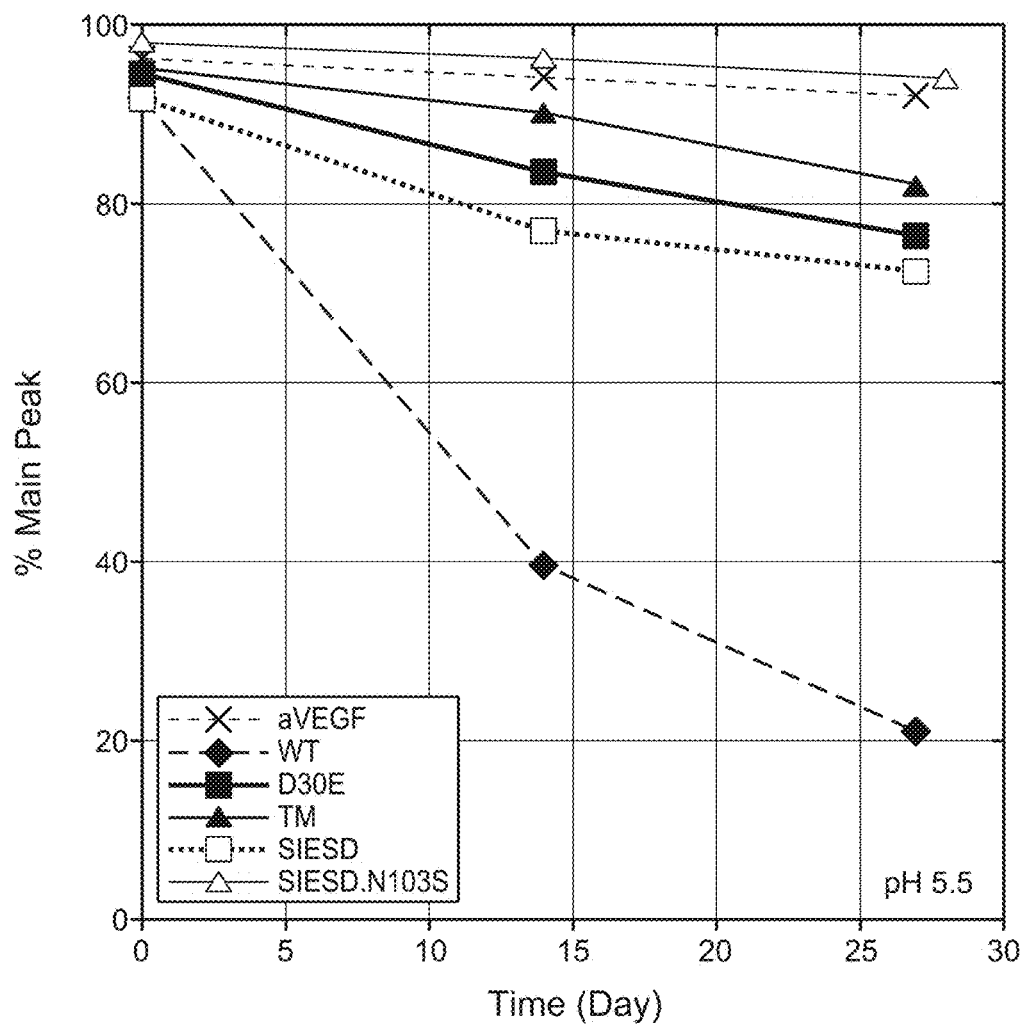
Figure 3B:
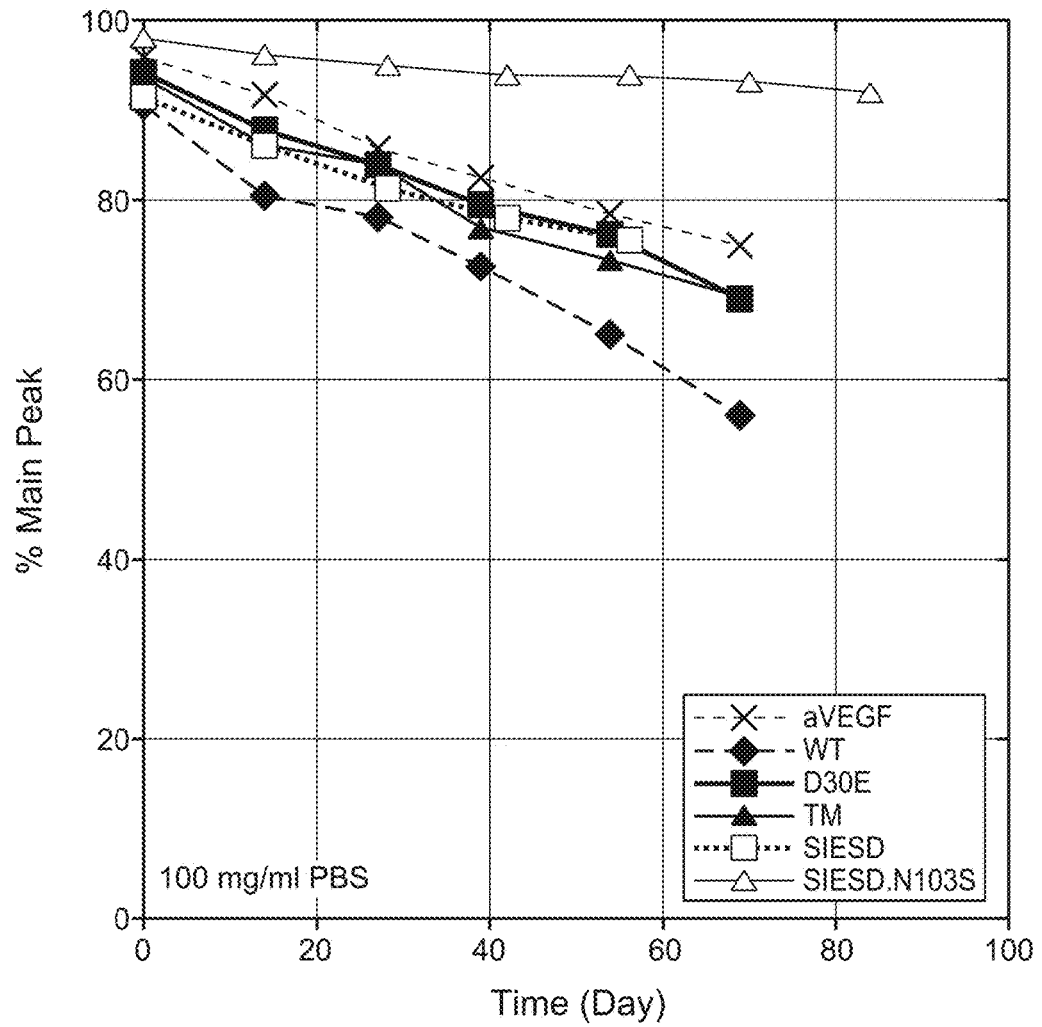

FIGS. 3A-3B illustrate degradations of various antibody Fab fragments over time under defined conditions whereby main peak is determined by ion-exchange chromatography (IEC) (3A: Fab protein concentration of 10 mg/mL in pH5.5 buffer; 3B: Fab protein concentration of 100 mg/ml in PBS).

Figure 4A:
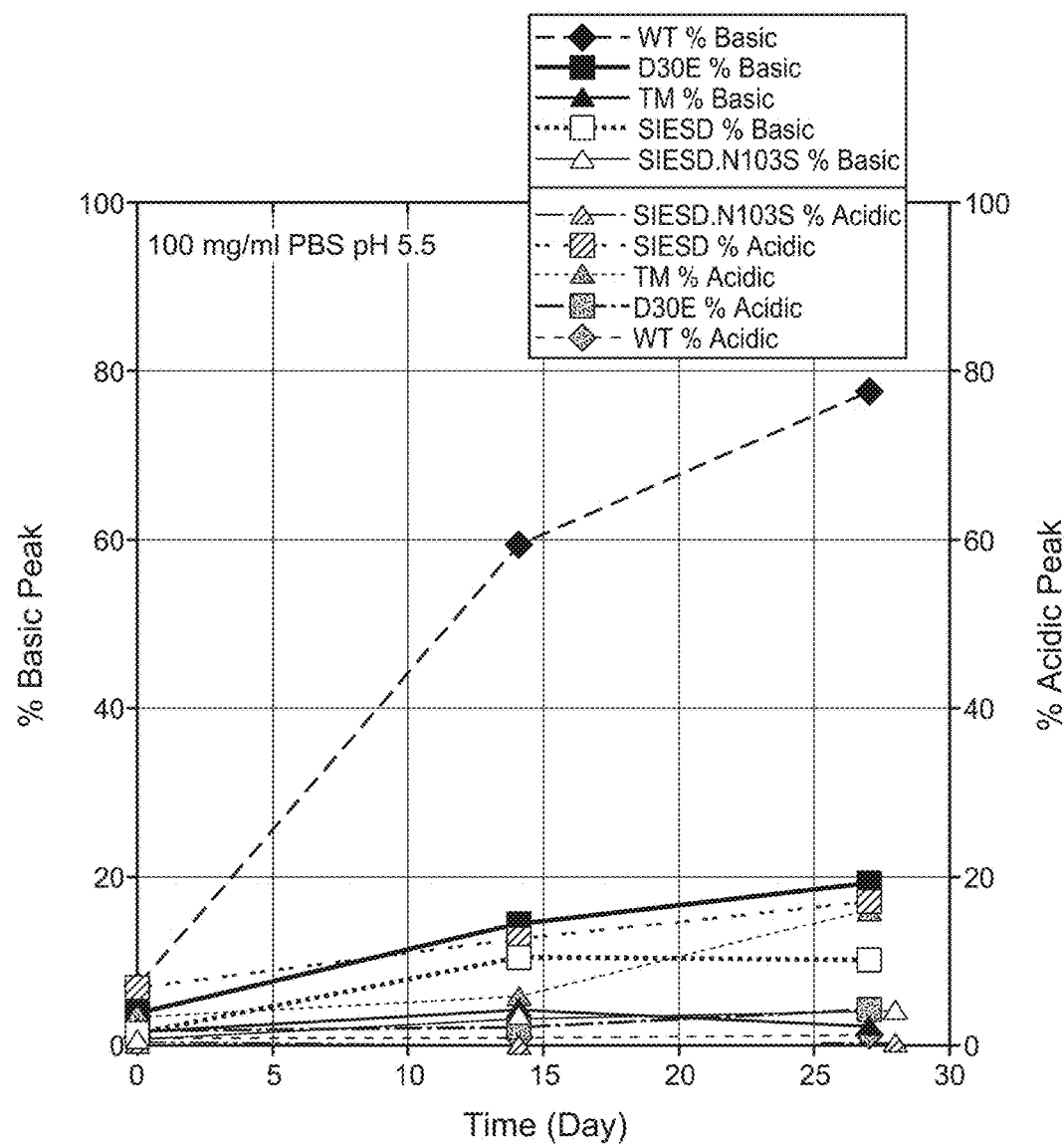
Figure 4B:
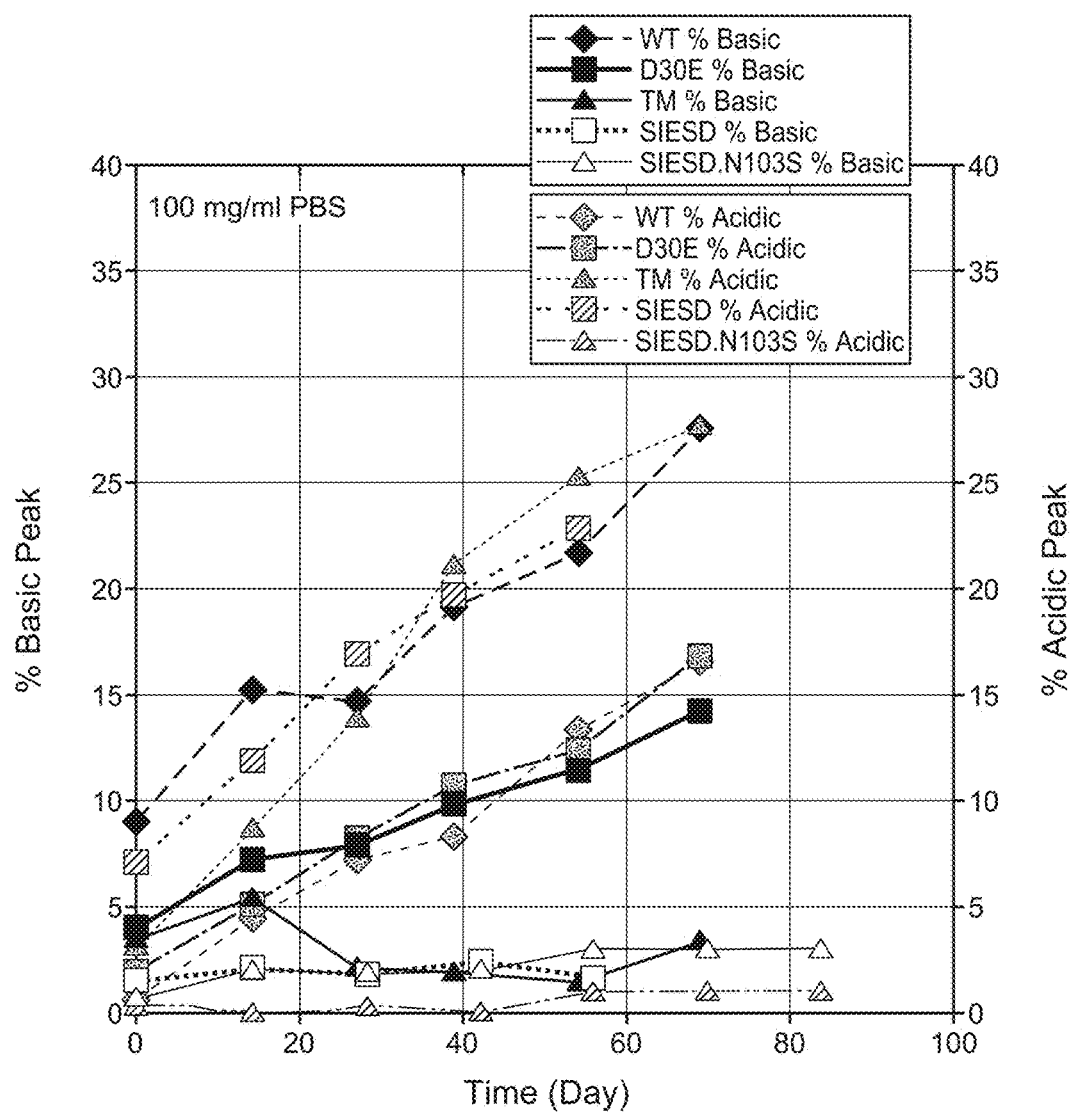

FIGS. 4A-4B illustrate isomerization and deamidation of various antibody Fab fragments over time under defined conditions (4A: Fab protein concentration of 10 mg/mL in pH5.5 buffer; 4B: Fab protein concentration of 100 mg/ml in PBS).

Figure 5:
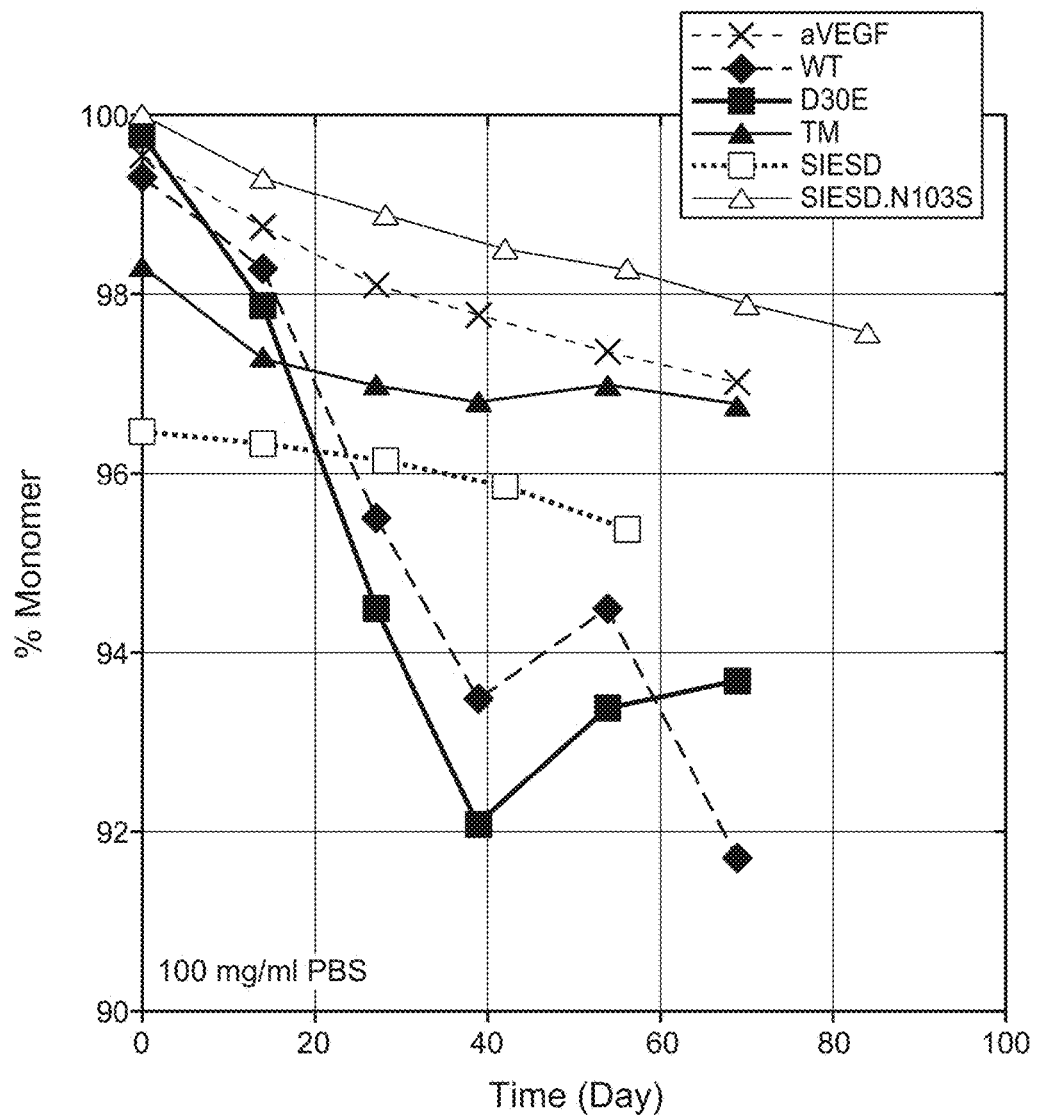

FIG. 5 illustrates aggregation of various antibody Fab fragments over prolonged time under defined condition (Fab protein concentration of 100 mg/ml in PBS) as determined by measurements of monomer peak by size-exclusion chromatography (SEC).

Figure 6:
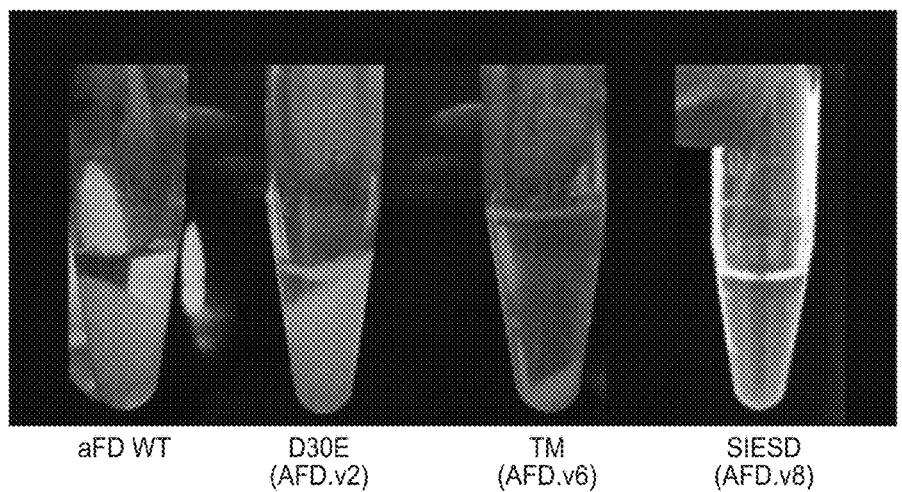

FIG. 6 illustrates solubility of aFD WT, AFD.v2, AFD.v6 and AFD.v8 at pH 6 and low ionic strength (~100 mg/ml in 20 mM His-HCl, pH 6).

Figure 7:
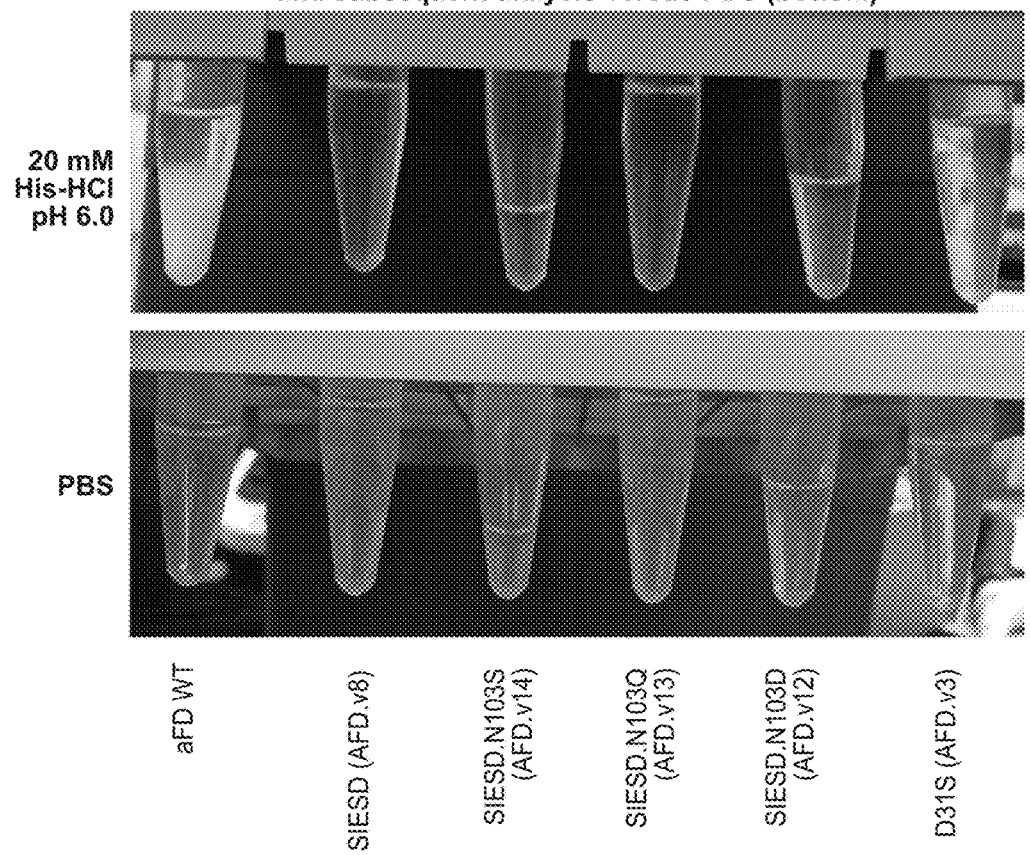

FIG. 7 illustrates solubility of antibody Fab fragments at pH 6 and low ionic strength (~100 mg/ml in 20 mM His-HCl, pH 6). The insolubility of aFD WT is reversed by the exchange into PBS, a salt (NaCl) containing buffer, via dialysis.

FIG. 8 illustrates solubility of antibody Fab fragments in PBS (pH 7.3) at 227 mg/ml for aFD WT, 269 mg/ml for AFD.v8 and 344 mg/ml for AFD.v14.

Figure 9:
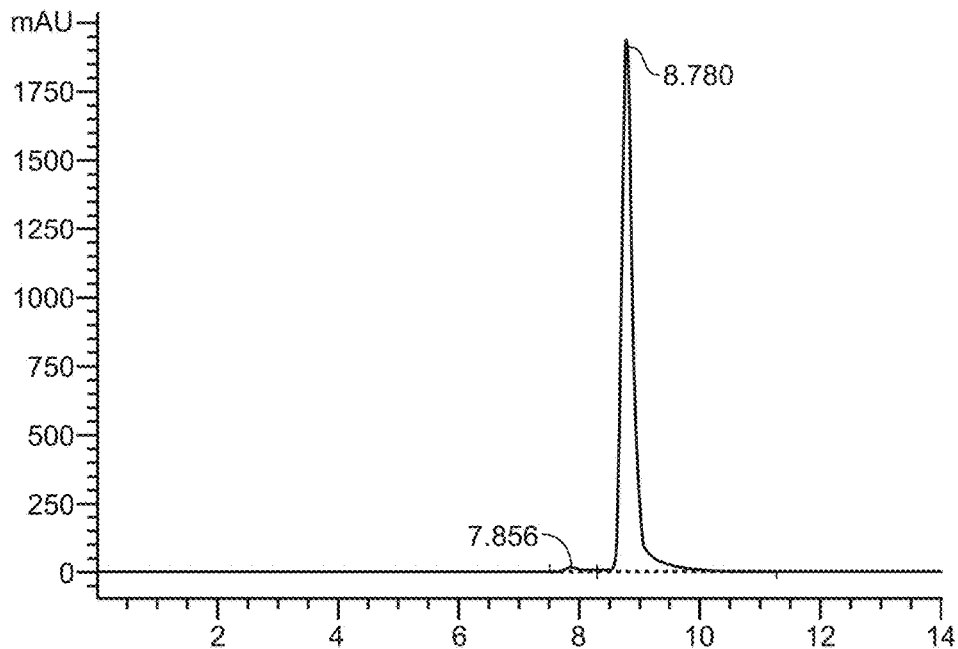

FIG. 9 illustrates % aggregate as measured by size-exclusion chromatography (SEC) of SIESD.N103S (AFD.v14) in PBS prior to 3 week incubation at 2-8° C.

Figure 10:
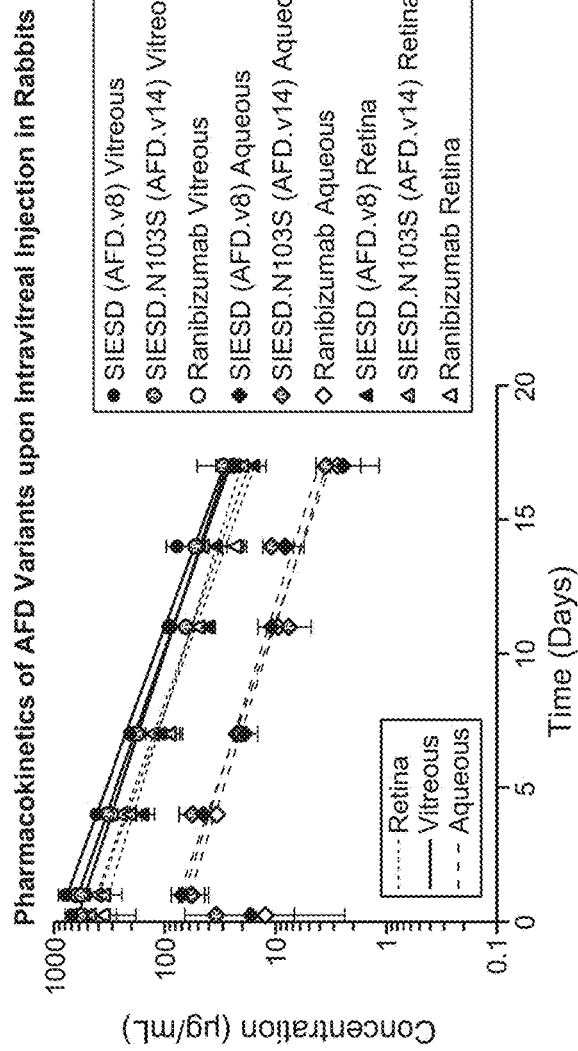

FIG. 10 illustrates pharmacokinetics of antibody Fab fragments upon intravitreal injection in rabbits.

FIG. 11 illustrates protein concentration dependence of viscosity for antibody Fab fragments in pH 5.5 buffer.

DETAILED DESCRIPTION OF THE INVENTION

Definitions

Terms used throughout this application are to be construed with ordinary and typical meaning to those of ordinary skill in the art. However, Applicants desire that the following terms be given the particular definition as defined below.

The term "antibody" is used in the broadest sense, and specifically covers full length monoclonal antibodies, polyclonal antibodies, multispecific antibodies (e.g., bispecific antibodies) and antibody fragments so long as they exhibit the desired biological activity such as antigen-binding activity. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. The term "Antibody" as used herein expressly encompasses antibody fragments retaining antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As used herein, an "anti-factor D antibody" means an antibody which specifically binds to Factor D in such a manner so as to inhibit or substantially reduce complement activation.

The term "Factor D" is used herein to refer to native sequence and variant Factor D polypeptides.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity-determining regions" (CDRs), the latter being of highest sequence variability and/or involved in antigen recognition. HVR-H3 is believed to play a unique role in conferring fine specificity to antibodies. See, e.g., Xu et al. (2000) Immunity 13:37-45; Johnson and Wu (2003) in Methods in Molecular Biology 248:1-25 (Lo, ed., Human Press, Totowa, N.J.). "Framework Region" or "FR" residues are those variable domain residues other than the hypervariable region residues as herein defined. An HVR region as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 24-34 (L1), 50-52 (L2), 91-96 (L3), 26-32 (H1), 53-55 (H2), and 96-101 (H3) (Chothia and Lesk, J. Mol. Biol. 196:901-917 (1987);

B) 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991).

C) 30-36 (L1), 46-55 (L2), 89-96 (L3), 30-35 (H1), 47-58 (H2), 93-100a-j (H3) (MacCallum et al. J. Mol. Biol. 262: 732-745 (1996).

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).)

An "antibody variant" or "modified antibody" of a reference antibody (also referred to as "starting antibody" or "parent antibody") is an antibody that comprises an amino acid sequence different from that of the reference/starting antibody, wherein one or more of the amino acid residues of the reference antibody have been modified. Generally, an antibody variant will possess at least 80% sequence identity, preferably at least 90% sequence identity, more preferably at least 95% sequence identity, and most preferably at least 98% sequence identity with the reference antibody. Percentage sequence identity is determined for example, by the Fitch et al., Proc. Natl. Acad. Sci. USA, 80: 1382-1386 (1983), version of the algorithm described by Needleman et al., J. Mol. Biol., 48: 443-453 (1970), after aligning the sequences of the reference antibody and the candidate antibody variant to provide for maximum homology. Identity or similarity is defined herein as the percentage of amino acid residues in the candidate variant sequence that are identical (i.e. same residue) or similar (i.e. amino acid residue from the same group based on common side-chain properties, see below) with the parent antibody residues, after aligning the sequences and introducing gaps, if necessary, to achieve the maximum percent sequence identity. Amino acid sequence variants of an antibody may be prepared by introducing appropriate nucleotide changes into DNA encoding the antibody, or by peptide synthesis. Such variants include, for example, deletions from, and/or insertions into and/or substitutions of, residues within the amino acid sequence of the antibody of interest. Any combination of deletion, insertion, and substitution is made to arrive at the final construct, provided that the final construct possesses the desired characteristics. The amino acid changes also may alter post-translational processes of the antibody, such as changing the number or position of glycosylation sites. Methods for generating antibody sequence variants of antibodies are similar to those for generating amino acid sequence variants of polypeptides described in U.S. Pat. No. 5,534,615, expressly incorporated herein by reference, for example.

A protein including an antibody is said to be "stable" if it essentially retains the intact conformational structure and biological activity. Various analytical techniques for measuring protein stability are available in the art and are reviewed in, e.g., Peptide and Protein Drug Delivery, 247-301, Vincent Lee Ed., Marcel Dekker, Inc., New York, N.Y., Pubs. (1991) and Jones (1993) Adv. Drug Delivery Rev. 10: 29-90. An antibody variant with "improved stability" refers to an antibody variant that is more stable comparing to the starting reference antibody. Preferably, antibody variants with improved stability are variants of the native (wild-type) antibodies in which specific amino acid residues are altered for the purpose of improving physical stability, and/or chemical stability, and/or biological activity, and/or reducing immunogenicity of the native antibodies. Walsh (2000) Nat. Biotech. 18:831-3.

The term "isomerization" refers generally to a chemical process by which a chemical compound is transformed into any of its isomeric forms, i.e., forms with the same chemical composition but with different structure or configuration and, hence, generally with different physical and chemical properties. Specifically used herein is aspartate isomerization, a process wherein one or more aspartic acid (D or Asp) residue(s) of a polypeptide have been transformed to isoaspartic acid residue(s). Geiger and Clarke (1987) J. Biol. Chem. 262:785-94.

The term "deamidation" refers generally to a chemical reaction wherein an amide functional group is removed from an organic compound. Specifically used herein is asparagine deamidation, a process wherein one or more asparagine (N or Asn) residue(s) of a polypeptide have been converted to aspartic acid (D or Asp), i.e. the neutral amide side chain has been converted to a residue with an overall acidic property. Xie and Schowen (1999) *J. Pharm. Sci.* 88:8-13.

Amino acid residues "prone" to certain identified physical or chemical processes (e.g., isomerization or deamidation) refer to those residues within a specific protein molecule that have been identified to have the propensity to undergo the identified processes such as isomerization or deamidation. Their propensities are often determined by their relative positions within the primary and/or conformational structure of the protein. For example, it has been shown that the first Asp in an Asp-XXX motif (wherein XXX can be Asp, Gly, His, Ser or Thr) is prone to Asp isomerization due to the involvement of its adjacent residue, where some other Asp within the same protein may not possess such propensity. Assays for identifying residues to certain process within a specific protein molecule are known in the art. See, e.g., Cacia et al (1996) *Biochem.* 35:1897-1903.

"Active" or "activity" or "biological activity" in the context of an anti-factor D antibody of the present invention is the ability to antagonize (partially or fully inhibit) a biological activity of Factor D. One example of a biological activity of a Factor D antagonist is the ability to achieve a measurable improvement in the state, e.g. pathology, of a Factor D-associated disease or condition, such as, for example, a complement-associated eye condition. The activity can be determined in in vitro or in vivo tests, including binding assays, alternative pathway hemolysis assays (e.g. assays measuring inhibition of the alternative pathway complement activity or activation), using a relevant animal model, or human clinical trials.

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions includes age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In one example, complement-associated eye conditions include age-related macular degeneration (AMD), including early AMD (e.g. includes multiple small to one or more non-extensive medium sized drusen), intermediate AMD (e.g. includes extensive medium drusen to one or more large drusen) and advanced AMD (e.g. includes geographic atrophy or advanced wet AMD (CNV). (Ferris et al., AREDS Report No. 18; Sallo et al., *Eye Res.*, 34(3): 238-40 (2009); Jager et al., *New Engl. J. Med.*, 359(1): 1735 (2008)). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, complement-associated eye condition is intermediate dry AMD. In one example, complement-associated eye condition is geographic atrophy. In one example, complement-associated eye condition is wet AMD (choroidal neovascularization (CNV)).

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated eye condition, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, higher primates, domestic and farm animals, and zoo, sports or pet animals such horses, pigs, cattle, dogs, cats and ferrets, etc. In one embodiment of the invention, the mammal is a human.

Administration "in combination with" one or more further therapeutic agents includes simultaneous (concurrent) and consecutive administration in any order.

"Therapeutically effective amount" is the amount of a "Factor D antagonist" which is required to achieve a measurable improvement in the state, e.g. pathology, of the target disease or condition, such as, for example, a complement-associated eye condition.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (ala); arginine (Arg); asparagine (Asn); aspartic acid (Asp); cysteine (Cys); glutamine (Gln); glutamic acid (Glu); glycine (Gly), histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residue(s) in a polypeptide chain. Examples of non-naturally occurring amino acid residues include norleucine, ornithine, norvaline, homoserine and other amino acid residue analogues such as those described in Ellman et al., *Meth. Enzym,* 202: 301-336 (1991). To generate such non-naturally occurring amino acid residues, the procedures of Noren et al., *Science,* 244: 182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The terms "long-acting delivery", "sustained-release" and "controlled release" are used generally to describe a delivery mechanism using formulation, dosage form, device or other types of technologies to achieve the prolonged or extended release or bioavailability of a therapeutic drug. It may refer to technologies that provide prolonged or extended release or bioavailability of the drug to the general systemic circulation or a subject or to local sites of action in a subject including (but not limited to) cells, tissues, organs, joints, regions, and the like. Furthermore, these terms may refer to a technology that is used to prolong or extend the release of the drug from a formulation or dosage form or they may refer to a technology used to extend or prolong the bioavailability or the pharmacokinetics or the duration of action of the drug to a subject or they may refer to a technology that is used to extend or prolong the pharmacodynamic effect elicited by a formulation. A "long-acting formulation," a "sustained release formulation," or a "controlled release formulation" is a pharmaceutical formulation, dosage form, or other technology that is used to provide long-acting delivery. In one aspect, the controlled release is used to improve drug's local bioavailability, specifically ocular residence time in the context of ocular delivery. "Increased ocular residence time" refers to the post-delivery period during which the delivered ocular drug remains effective both in terms of quality (stay active) and in terms of quantity (effective amount). In addition to or in lieu of high dose and controlled release, the drug can be modified post-translationally, such as via PEGylation, to achieve increased in vivo half-life.

Anti-Factor D Antibodies and Variants Thereof

The invention herein includes the production and use of anti-Factor D antibodies and variants thereof. In one aspect, the parent reference anti-Factor D antibody forming the base for creating the variants of the invention is a humanized anti-Factor D antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can in some instances be important to reduce antigenicity and/or HAMA response (human anti-mouse antibody) when the antibody is intended for human therapeutic use. Reduction or elimination of a HAMA response is generally a significant aspect of clinical development of suitable therapeutic agents. See, e.g., Khaxzaeli et al. (1988) *J. Natl. Cancer Inst* 80:937; Jaffers et al. (1986) *Transplantation* 41:572; Shawler et al. (1985) *J. Immunol.* 135:1530; Sears et al. (1984) *J. Biol. Response Mod.* 3:138; Miller et al. (1983) *Blood* 62:988; Hakimi et al. (1991) *J. Immunol.* 147:1352; Reichmann et al. (1988) *Nature* 332:323; Junghans et al. (1990) *Cancer Res.* 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al. (1993) *J. Immunol.* 151:2296; Chothia et al. (1987) *J. Mol. Biol.* 196:901). Another method uses a particular framework region derived from the consensus sequence of all human antibodies of a particular subgroup of light or heavy chains. The same framework may be used for several different humanized antibodies (Carter et al. (1992) *Proc. Natl. Acad. Sci. USA* 89:4285; Presta et al. (1993) *J. Immunol.* 151:2623).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), the acceptor human frameworks may be from, or derived from, a human consensus framework sequence as such frameworks have been demonstrated to have minimal, or no, immunogenicity in human patients. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. In one embodiment, the VH acceptor human framework is identical in sequence to the VH human immunoglobulin framework sequence or human consensus framework sequence. In one embodiment, the VL acceptor human framework is identical in sequence to the VL human immunoglobulin framework sequence or human consensus framework sequence. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in the public databases.

In one embodiment, human consensus frameworks herein are from, or derived from, VH subgroup VII and/or VL kappa subgroup I consensus framework sequences.

In one embodiment, the human framework template used for generation of an anti-Factor D antibody may comprise framework sequences from a template comprising a combination of VI-4.1b+ (VH7 family) and JH4d for VH chain and/or a combination of DPK4 (VκI family) and JK2 for VL chain.

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-36 or 24-34 (L1), 46-56 or 50-56 (L2) and 89-97 (L3), 26-35B (H1), 50-65, 47-65 or 49-65 (H2) and 93-102, 94-102, or 95-102 (H3).

In one aspect, the anti-Factor D antibody or antibody variants of the invention comprises a light chain domain and a heavy chain variable domain. In one aspect, the reference anti-Factor D antibody of the invention comprises a light chain variable domain of SEQ ID NO:3. In one aspect, the reference anti-Factor D antibody of the invention comprises a heavy chain variable domain of SEQ ID NO:4.

Further, an anti-Factor D antibody may comprise any suitable constant domain sequence, provided that the antibody retains the ability to bind Factor D. For example, in some embodiments, anti-Factor D antibodies of the invention comprise at least a portion of a heavy chain constant domain. In one embodiment, anti-Factor D antibodies of the invention comprise a heavy chain constant domain of either one or a combination of an α, δ, o, γ, or μ heavy chain. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. In one embodiment, anti-Factor D antibodies of the invention comprise a heavy chain constant domain comprising substitutions at amino acid positions that results in a desired effect on effector function (e.g. binding affinity). In one embodiment, anti-Factor D antibodies of the invention comprise a heavy chain constant domain comprising substitutions at amino acid positions that do not result in an effect on effector function (e.g. binding affinity). In one embodiment, anti-Factor D antibodies of the invention comprise a heavy chain constant domain of the IgG type (e.g. IgG1, IgG2, IgG3 or IgG4) and further comprise a substitution at position 114 (Kabat numbering; equivalent to 118 in EU numbering), 168 (Kabat numbering; equivalent to 172 in EU numbering), 172 (Kabat numbering; equivalent to 176 in EU numbering) and/or 228 (EU numbering). In one embodiment, anti-Factor D antibodies of the invention comprise a heavy chain constant domain of the IgG (e.g. IgG1, IgG2, IgG3 or IgG4) type and further comprise a substitution at position 114 wherein position 114 is a cysteine (C) or alanine (A), position 168 is cysteine (C) or alanine (A), position 172 is a cysteine (C) or alanine (A) and/or position 228 is a proline (P), arginine (R) or serine (S).

Further, for example, in some embodiments, anti-Factor D antibodies of the invention comprise at least a portion of a light chain constant domain. In one embodiment, anti-Factor D antibodies of the invention comprise a light chain constant domain of either one or a combination of a kappa or a lambda light chain, as the light chain from any vertebrate species can be assigned to one of two clearly distinct types, called kappa and lambda, based on the amino acid sequences of their constant domains. In one embodiment, anti-Factor D antibodies of the invention comprise a light chain constant domain comprising substitutions at amino acid positions that results in a desired effect on effector function (e.g. binding affinity). In one embodiment, anti-Factor D antibodies of the invention comprise a light chain constant domain comprising substitutions at amino acid positions that do not result in an effect on effector function (e.g., binding affinity). In one embodiment, anti-Factor D antibodies of the invention comprise a light chain constant domain of the kappa type and further comprise a substitution at position 110, 144, 146 and/or 168 (Kabat numbering). In one embodiment, anti-Factor D antibodies of the invention comprise a light chain constant domain of the kappa type and further comprise a substitution at position 110 wherein 110 is a cysteine (C) or valine (V), at position 144 wherein 144 is a cysteine (C) or alanine (A), at position 146 wherein 146 is a isoleucine (I) or valine (V) and/or at position 168 wherein 168 is a cysteine (C) or serine (S).

A parent or reference anti-Factor D antibody, including a humanized anti-Factor D antibody, can be modified to generate modified anti-Factor D antibodies, or anti-Factor D antibody variants. In one embodiment, the modified anti-Factor D antibodies, and variants thereof, may have improved physical, chemical, biological or homogeneity properties over the parent antibody.

In one embodiment, an antibody of this invention comprises one or more amino acid alterations (e.g. substitutions) into one or more of the hypervariable regions of the parent antibody. Alternatively, or in addition, one or more alterations (e.g. substitutions) of framework region residues may be introduced in the parent antibody. Examples of framework region residues to modify include those which non-covalently bind antigen directly (Amit et al., (1986) *Science*, 233: 747-753); interact with/effect the conformation of a CDR (Chothia et al. (1987)*J. Mol. Biol.*, 196: 901-917), and/or participate in the $V_L$-$V_H$ interface (EP 239 400B1). In certain embodiments, modification of one or more of such framework region residues results in an enhancement of the binding affinity of the antibody for the antigen. For example, from about one to about 5 framework residues may be altered in this embodiment of the invention. Examples of framework or HVR region residues to modify include sites, wherein modifications at such sites result in the generation of deamidated variants (for example, asparagine (N or Asn) residue(s) modified to aspartate (D or Asp), oxidation variants (for example, methionine (M or Met) residue(s) and/or tryptophan (W or Trp) residue(s) modified to sulfone or sulfoxide) or pyroglutamate variants (for example, glutamine (Q or Gln) residue(s) modified to pyroglutamate). Examples of framework region residues or HVR region residues to modify include possible deamidation sites (i.e. asparagine (N or Asn)), oxidation sites (i.e. methionine (M or Met) or tryptophan (W or Trp)) or pyroglutamate conversion sites (i.e. glutamine (Q or Gln)), wherein modification at such sites prevent deamidation and/or oxidation and/or pyroglutamate conversion, respectively.

To prevent the formation of deamidated variants, asparagine (N or Asn) may be mutated to alanine (A or Ala), glutamine (Q or Gln) or serine (S or Ser). To prevent the formation of oxidated variants, methionine (Met) or tryptophan (W or Trp) may be mutated to leucine (L) or isoleucine (I). To prevent the formation of pyroglutamate variants, glutamine (Q or Gln) may be mutated to glutamate (E or Glu). (Amphlett, G. et al., *Pharm. Biotechnol.*, 9:1-140 (1996)). Alternatively, or in addition, one or more alterations (e.g. substitutions) of framework region residues may be in the Fc region in the parent antibody.

One useful procedure for generating such modified antibodies is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity (i.e. binding affinity or hemolysis assay) as described herein.

Even more substantial modifications in the antibodies or fragments thereof (e.g. antigen-binding fragments) biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are modified, and those modifications with improved binding affinity are selected by phage display.

Nucleic acid molecules encoding amino acid sequence mutants or modified amino acid sequences are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the parent antibody. One method for making mutants or variants or modified amino acid sequences is site directed mutagenesis (see, e.g., Kunkel (1985) *Proc. Natl. Acad. Sci. USA* 82:488).

In certain embodiments, the modified antibody will only have a single hypervariable region residue substituted. In other embodiments, two or more of the hypervariable region residues of the parent antibody will have been substituted, e.g. from about two to about ten hypervariable region substitutions. Ordinarily, the modified antibody will have an amino acid sequence having at least 75% amino acid sequence identity or similarity (defined above in Definition section) with the amino acid sequence of either the heavy or light chain variable domain of the parent antibody, more preferably at least 80%, more preferably at least 85%, more preferably at least 90%, and most preferably at least 95%.

Following production of the modified antibody, the biological activity of that molecule relative to the parent antibody is determined. As noted above, this may involve determining the binding affinity and/or other biological activities of the antibody variant, or fragment thereof (e.g. antigen-binding fragment). In one embodiment of the invention, a panel of modified antibodies is prepared and screened for binding affinity for the antigen such as Factor D or a fragment thereof. One or more of the antibody mutants or modified antibodies selected from this initial screen are optionally subjected to one or more further biological activity assays to confirm that the antibody variant(s), or fragments thereof (e.g. antigen-binding fragments) are indeed useful, e.g. for preclinical studies.

The modified anti-Factor D antibodies described herein may be subjected to further modifications, oftentimes depending on the intended use of the modified antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the modified antibody also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment).

Another type of amino acid mutant has an altered glycosylation pattern. This may be achieved by deleting one or more carbohydrate moieties found in the antibody, and/or adding one or more glycosylation sites that are not present in the antibody. Glycosylation of antibodies, or antibody fragments (e.g. antigen-binding fragments) is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody and antibody variants of the invention can also be further covalently modified by conjugating the antibody to one of a variety of non-proteinacious polymer molecules. The antibody-polymer conjugates can be made using any suitable technique for derivatizing antibody with polymers. It will be appreciated that the invention is not limited to conjugates utilizing any particular type of linkage between an antibody or antibody fragment and a polymer.

In one aspect, the conjugates of the invention include species wherein a polymer is covalently attached to a specific site or specific sites on the parental antibody, i.e. polymer attachment is targeted to a particular region or a particular amino acid residue or residues in the parental antibody or antibody fragment. Site specific conjugation of polymers is most commonly achieved by attachment to cysteine residues in the parental antibody or antibody fragment. In such embodiments, the coupling chemistry can, for example, utilize the free sulfhydryl group of a cysteine residue not in a disulfide bridge in the parental antibody. The polymer can be activated with any functional group that is capable of reacting specifically with the free sulfhydryl or thiol group(s) on the parental antibody, such as maleimide, sulfhydryl, thiol, triflate, tesylate, aziridine, exirane, and 5-pyridyl functional groups. The polymer can be coupled to the parental antibody using any protocol suitable for the chemistry of the coupling system selected, such as the protocols and systems described in U.S. Pat. Nos. 4,179,337; 7,122,636, and Jevsevar et al. (2010) Biotech. J. 5:113-128.

In one embodiment, one or more cysteine residue(s) naturally present in the parental antibody is (are) used as attachment site(s) for polymer conjugation. In another embodiment, one or more cysteine residue(s) is (are) engineered into a selected site or sites in the parental antibody for the purpose of providing a specific attachment site or sites for polymer.

In one aspect, the invention encompasses antibody fragment-polymer conjugates, wherein the antibody fragment is a Fab, and the polymer is attached to one or more cysteine residue in the light or heavy chain of the Fab fragment that would ordinarily form the inter-chain disulfide bond linking the light and heavy chains.

In another aspect, the invention encompasses antibody fragment-polymer conjugates, wherein the antibody fragment is a Fab', and the polymer attachment is targeted to the hinge region of the Fab' fragment. In one embodiment, one or more cysteine residue(s) naturally present in the hinge region of the antibody fragment is (are) used to attach the polymer. In another embodiment, one or more cysteine residues is (are) engineered into the hinge region of the Fab' fragment for the purpose of providing a specific attachment site or sites for polymer. In one embodiment, the anti-Factor D antibody variant Fab fragment of the invention is modified by adding one cysteine at the C'-terminal end for the purpose of providing one attachment site for polymer conjugation. In another embodiment, the anti-Factor D antibody variant Fab fragment of the invention is modified by adding four additional residues, Cys-Pro-Pro-Cys (SEQ ID NO: 21), at the C'-terminal end for the purpose of providing two attachment sites for polymer conjugation.

One commonly used antibody conjugation is PEGylation, wherein one or more polyethylene glycol (PEG) polymers are covalently attached to the antibody's constant region. See U.S. Pat. Nos. 4,179,337; 7,122,636. PEG polymers of different sizes (e.g., from about 500 D to about 300,000 D) and shapes (e.g., linear or branched) have been known and widely used in the field. The polymers useful for the present invention may be obtained commercially (e.g., from Nippon Oil and Fats; Nektar Therapeutics; Creative PEGWorks) or prepared from commercially available starting materials using conventional chemical procedures. PEGylation changes the physical and chemical properties of the antibody drug, and may results in improved pharmacokinetic behaviors such as improved stability, decreased immunogenicity, extended circulating life as well as increased residence time.

Affinity and Biological Activity

Antibodies having characteristics identified herein as being desireable in an anti-Factor D antibody, may be screened for desirable properties such as factor D-binding affinity and factor D-inhibiting activity in vitro or in vivo.

a. Affinity

In one aspect, the invention provides anti-Factor D antibody variants that compete with the parent anti-Factor D antibody from which they are generated. Anti-Factor D antibody variants that bind to the same epitope as the parent anti-Factor D antibody are also provided.

To determine whether an anti-Factor D antibody variant bind to the same epitope on human Factor D bound by a reference anti-Factor D antibody, a cross-blocking assay may be performed (Antibodies, A Laboratory Manual, Cold Spring Harbor Laboratory, Ed Harlow and David Lane (1988)). Alternatively, epitope mapping may be performed to determine whether an anti-Factor D antibody binds an epitope of interest (Champe et al. (1995) *J. Biol. Chem.* 270: 1388-1394. Antibody affinities, for example for human Factor D, may be determined using standard methods, including the surface plasmon resonance (SPR) assay described in more details in the Examples.

In one aspect, the factor D binding affinity of the anti-Factor D antibody variant of the invention is comparable to that of the parent anti-Factor D antibody from which it is generated. In some aspects, the factor D binding affinity of anti-Factor D antibody variant of the invention is within 10-fold, 7-fold, 5-fold, 2-fold or 1-fold of that of the parent anti-Factor D antibody.

In one embodiment, the invention provides an anti-Factor D antibody, wherein the affinity of the antibody in its monovalent form to Factor D (e.g., affinity of the antibody as a Fab fragment to Factor D) is 20 nM ($20 \times 10^{-9}$ M) or better. In another embodiment, the invention provides an anti-Factor D antibody, wherein the affinity of the antibody in its monovalent form to Factor D (e.g., affinity of the antibody as a Fab fragment to Factor D) is 10 nM ($10 \times 10^{-9}$ M) or better. In another embodiment, the invention provides an anti-Factor D antibody, wherein the affinity of the antibody in its monovalent form to Factor D (e.g., affinity of the antibody as a Fab fragment to Factor D) is 1.0 nM ($1.0 \times 10^{-9}$ M) or better. In another embodiment, the invention provides an anti-Factor D antibody, wherein the affinity of the antibody in its monovalent form to Factor D (e.g., affinity of the antibody as a Fab fragment to Factor D) is 0.5 nM ($0.5 \times 10^{-9}$ M) or better. In another embodiment, the invention provides an anti-Factor D antibody, wherein the affinity of the antibody in its monovalent form to Factor D (e.g., affinity of the antibody as a Fab fragment to Factor D) is 1.0 pM ($1.0 \times 10^{-12}$ M) or better. In another embodiment, the invention provides an anti-Factor D antibody, wherein the affinity of the antibody in its monovalent form to Factor D (e.g., affinity of the antibody as a Fab fragment to Factor D) is 0.5 pM ($0.5 \times 10^{-12}$ M) or better.

In another embodiment, the invention provides an anti-Factor D antibody, wherein the affinity of the antibody in its bivalent form to Factor D (e.g., affinity of the antibody as an IgG to Factor D) is 10.0 nM ($10.0 \times 10^{-9}$ M) or better. In another embodiment, the invention provides an anti-Factor D antibody, wherein the affinity of the antibody in its bivalent form to Factor D (e.g., affinity of the antibody as an IgG to Factor D) is 5.0 nM ($5.0 \times 10^{-9}$ M) or better. In another embodiment, the invention provides an anti-Factor D antibody, wherein the affinity of the antibody in its bivalent form to Factor D (e.g., affinity of the antibody as an IgG to Factor D) is 1.0 nM ($1.0 \times 10^{-9}$ M) or better. In another embodiment, the invention provides an anti-Factor D antibody, wherein the affinity of the antibody in its bivalent form to Factor D (e.g., affinity of the antibody as an IgG to Factor D) is 0.5 nM ($0.5 \times 10^{-9}$ M) or better. In another embodiment, the invention provides an anti-Factor D antibody, wherein the affinity of the antibody in its bivalent form to Factor D (e.g., affinity of the antibody as an IgG to Factor D) is 5.0 pM ($5.0 \times 10^{-12}$ M) or better. In another embodiment, the invention provides an anti-Factor D antibody, wherein the affinity of the antibody in its bivalent form to Factor D (e.g., affinity of the antibody as an IgG to Factor D) is 2.0 pM ($2.0 \times 10^{-12}$ M) or better. In another embodiment, the invention provides an anti-Factor D antibody, wherein the affinity of the antibody in its bivalent form to Factor D (e.g., affinity of the antibody as an IgG to Factor D) is 1.0 pM ($1.0 \times 10^{-12}$ M) or better. In another embodiment, the invention provides an anti-Factor D antibody, wherein the affinity of the antibody in its bivalent form to Factor D (e.g., affinity of the antibody as an IgG to Factor D) is 0.5 pM ($0.5 \times 10^{-12}$ M) or better.

In another embodiment, the invention provides an anti-Factor D antibody, wherein the affinity of the antibody in its monovalent form to Factor D (e.g., affinity of the antibody as a Fab fragment to Factor D) is between 0.5 mM ($0.5 \times 10^{-6}$ M) and 0.5 pM ($0.5 \times 10^{-12}$ M). In another embodiment, the invention provides an anti-Factor D antibody, wherein the affinity of the antibody in its monovalent form to Factor D (e.g., affinity of the antibody as a Fab fragment to Factor D) is between 15 nM ($15 \times 10^{-9}$ M) and 0.1 nM ($0.1 \times 10^{-9}$ M). In another embodiment, the invention provides an anti-Factor D antibody, wherein the affinity of the antibody in its monovalent form to Factor D (e.g., affinity of the antibody as a Fab fragment to Factor D) is between 5.5 nM ($5.5 \times 10^{-9}$ M) and 1 nM ($1 \times 10^{-9}$ M). In another embodiment, the invention provides an anti-Factor D antibody, wherein the affinity of the antibody in its monovalent form to Factor D (e.g., affinity of the antibody as a Fab fragment to Factor D) is between 0.5 pM ($0.5 \times 10^{-12}$ M) and 50 pM ($5 \times 10^{-11}$ M).

In another embodiment, the invention provides an anti-Factor D antibody, wherein the affinity of the antibody in its bivalent form to Factor D (e.g., affinity of the antibody as an IgG to Factor D) is between 0.5 mM ($0.5 \times 10^{-6}$ M) and 0.5 pM ($0.5 \times 10^{-12}$ M). In another embodiment, the invention provides an anti-Factor D antibody, or antibody variants thereof, wherein the affinity of the antibody in its bivalent form to Factor D (e.g., affinity of the antibody as an IgG to Factor D) is between 10 nM ($10 \times 10^{-9}$ M) and 0.05 nM ($0.05 \times 10^{-9}$ M). In another embodiment, the invention provides an anti-Factor D antibody, wherein the affinity of the antibody in its bivalent form to Factor D (e.g., affinity of the antibody as an IgG to Factor D) is between 5.5 nM ($5.5 \times 10^{-9}$ M) and 1 nM ($1 \times 10^{-9}$ M). In another embodiment, the invention provides an anti-Factor D antibody, wherein the affinity of the antibody in its bivalent form to Factor D (e.g., affinity of the antibody as an IgG to Factor D) is between 0.5 pM ($0.5 \times 10^{-12}$ M) and 50 pM ($5 \times 10^{-11}$ M).

In another embodiment, the invention provides an anti-Factor D antibody, wherein the affinity of the antibody in its monovalent form to Factor D (e.g., affinity of the antibody as a Fab fragment to Factor D) is about 1.4 pM ($1.4 \times 10^{-12}$ M). In another embodiment, the invention provides an anti-Factor D antibody, wherein the affinity of the antibody in its bivalent form to Factor D (e.g., affinity of the antibody as a IgG to Factor D) is about 1.1 pM ($1.1 \times 10^{-12}$ M). In another embodiment, the invention provides an anti-Factor D antibody, wherein the affinity of the antibody in its monovalent form to Factor D (e.g., affinity of the antibody as a Fab fragment to Factor D) is about 0.19 nM ($0.19 \times 10^{-9}$ M). In another embodiment, the invention provides an anti-Factor D antibody, wherein the affinity of the antibody in its bivalent form to Factor D (e.g., affinity of the antibody as a IgG to Factor D) is about 0.08 nM ($0.08 \times 10^{-9}$ M). In another embodiment, the invention provides an anti-Factor D antibody, wherein the affinity of the antibody in its monovalent form to Factor D (e.g., affinity of the antibody as a Fab fragment to Factor D) is about 12.3 nM ($12.3 \times 10^{-9}$ M). In another embodiment, the invention provides an anti-Factor D antibody, wherein the affinity of the antibody in its bivalent form to Factor D (e.g., affinity of the antibody as a IgG to Factor D) is about 9.0 nM ($9.0 \times 10^{-9}$ M).

In another embodiment, the invention provides an anti-Factor D antibody, wherein the affinity of the antibody in its monovalent form to Factor D (e.g., affinity of the antibody as a Fab fragment to Factor D) is about 1.4 pM ($1.4 \times 10^{-12}$ M)+/−0.5. In another embodiment, the invention provides an anti-Factor D antibody, wherein the affinity of the antibody in its bivalent form to Factor D (e.g., affinity of the antibody as an IgG to Factor D) is about 1.1 pM ($1.1 \times 10^{-12}$ M)+/−0.6. In another embodiment, the invention provides an anti-Factor D antibody, wherein the affinity of the antibody in its monovalent form to Factor D (e.g., affinity of the antibody as a Fab fragment to Factor D) is about 0.19 nM ($0.19 \times 10^{-9}$ M)+/−0.01. In another embodiment, the invention provides an anti-Factor D antibody, wherein the affinity of the antibody in its bivalent form to Factor D (e.g., affinity of the antibody as a IgG to Factor D) is about 0.08 nM ($0.08 \times 10^{-9}$ M)+/−0.01. In another embodiment, the invention provides an anti-Factor D antibody, wherein the affinity of the antibody in its monovalent form to Factor D (e.g., affinity of the antibody as a Fab fragment to Factor D) is about 12.3 nM ($12.3 \times 10^{-9}$ M)+/−2. In another embodiment, the invention provides an anti-Factor D antibody, wherein the affinity of the antibody in its bivalent form to Factor D (e.g., affinity of the antibody as a IgG to Factor D) is about 9.0 nM ($9.0 \times 10^{-9}$ M) +/−1.

In another embodiment, an anti-Factor D antibody, may have an affinity in its monovalent form to Factor D (e.g., affinity of the antibody as a Fab fragment to Factor D) of about 1.4 pM ($1.4 \times 10^{-12}$ M)+/−2. In another embodiment, an anti-Factor D antibody, may have an affinity in its bivalent form to Factor D (e.g., affinity of the antibody as a IgG to Factor D) of about 1.1 pM ($1.1 \times 10^{-12}$ M)+/−2. In another embodiment, an anti-Factor D antibody, may have an affinity in its monovalent form to Factor D (e.g., affinity of the antibody as a Fab fragment to Factor D) is about 0.19 nM ($0.19 \times 10^{-9}$ M)+/−2. In another embodiment, an anti-Factor D antibody, or antibody variant thereof, may have an affinity in its bivalent form to Factor D (e.g., affinity of the antibody as a IgG to Factor D) is about 0.08 nM ($0.08 \times 10^{-9}$ M)+/−2. In another embodiment, an anti-Factor D antibody may have an affinity in its monovalent form to Factor D (e.g., affinity of the antibody as a Fab fragment to Factor D) is about 12.3 nM ($12.3 \times 10^{-9}$ M)+/−2. In another embodiment, an anti-Factor D antibody may have an affinity in its bivalent form to Factor D (e.g., affinity of the antibody as a IgG to Factor D) is about 9.0 nM ($9.0 \times 10^{-9}$ M)+/−2.

As is well-established in the art, binding affinity of a ligand to its receptor can be determined using any of a variety of assays, and expressed in terms of a variety of quantitative values. Accordingly, in one embodiment, the binding affinity is expressed as $K_D$ values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the $K_D$ values of the humanized antibody in Fab form and said reference/comparator Fab antibody. For example, in one embodiment, if an antibody of the invention (A) has an affinity that is "3-fold lower" than the affinity of a reference antibody (M), then if the $K_D$ value for A is 3×, the $K_D$ value of M would be 1×, and the ratio of $K_D$ of A to $K_D$ of M would be 3:1. Conversely, in one embodiment, if an antibody of the invention (C) has an affinity that is "3-fold greater" than the affinity of a reference antibody (R), then if the $K_D$ value for C is 1×, the $K_D$ value of R would be 3×, and the ratio of $K_D$ of C to $K_D$ of R would be 1:3. Any of a number of assays known in the art, including those described herein, can be used to obtain binding affinity measurements, including, for example, Biacore, radioimmunoassay (RIA) and ELISA.

Further, $K_D$ values for an antibody of the invention may vary depending on conditions of the particular assay used. For example, in one embodiment, binding affinity measurements may be obtained in an assay wherein the Fab or antibody is immobilized and binding of the ligand, i.e. Factor D, is measured or alternatively, the ligand, i.e. Factor D, for the Fab or antibody is immobilized and binding of the Fab or antibody is measured. In one embodiment, the binding affinity measurements may be obtained in an assay wherein the regeneration conditions may comprise (1) 10 mM glycine or 4M $MgCl_2$ at pH 1.5, and (2) pH between pH of 1.0 and pH of 7.5, including pH of 1.5, pH of 5.0, pH of 6.0 and pH of 7.2. In one embodiment, the binding affinity measurements may be obtained in an assay wherein the binding conditions may comprise (1) PBS or HEPES-buffered saline and (2) TWEEN-20™ non-ionic detergent, i.e. 0.1% TWEEN-20™ non-ionic detergent. In one embodiment, the binding affinity measurements may be obtained in an assay wherein the source of the ligand, i.e Factor D, may be from commercially available sources. In one embodiment, binding affinity measurements may be obtained in an assay wherein (1) the Fab or antibody is immobilized and binding of the ligand, i.e. Factor D is measured, (2) the regeneration conditions comprise 4M $MgCl_2$ at pH 7.2 and (3) the binding conditions comprise HEPES-buffered saline, pH 7.2 containing 0.1% TWEEN-20™ non-ionic detergent. In one embodiment, binding affinity measurements may be obtained in an assay wherein (1) the ligand, i.e. Factor D, is immobilized and binding of the Fab or antibody is measured, (2) the regeneration conditions comprise 10 mM glycine at pH 1.5 and (3) the binding conditions comprise PBS buffer.

b. Biological Activity

To determine whether an anti-Factor D antibody, or variant or fragment thereof (e.g. antigen-binding fragment) is capable of binding to Factor D and exerting a biological effect, for example, inhibition of alternative pathway hemolysis, hemolytic inhibition assays using rabbit RBCs may be used, including those described in Example 2. Such hemolytic inhibition may be determined using standard assays (Kostavasili et al. (1997) *J of Immunology* 158:1763-72; Wiesmann et al. (2006) *Nature* 444:159-60). Activation of complement in such assays may be initiated with serum or plasma. Appropriate concentrations of Factor D in serum or plasma (Pascual et al. (1998) *Kidney International* 34:529-536; Complement Facts Book, Bernard J. Morley and Mark J. Walport, editors, Academic Press (2000); Barnum et al. (1984) *J. Immunol. Methods,* 67: 303-309) can be routinely determined according to methods known in the art, including those that have been described in references such as Pascual et al. (1998) *Kidney International* 34:529-536 and Barnum et al. (1984) *J. Immunol. Methods* 67:303-309. The present invention relates generally to antibodies capable of inhibiting biological activities associated with Factor D. For example, at a concentration of 18 µg/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107)

In one embodiment, the invention includes anti-Factor D antibodies, wherein a Fab fragment of such antibodies inhibits alternative pathway hemolysis with $IC_{50}$ values less than 30 nM. In one embodiment, the invention includes anti-Factor D antibodies, wherein a Fab fragment of such antibodies inhibits alternative pathway hemolysis with $IC_{50}$ values less than 15 nM. In one embodiment, the invention provides anti-Factor D antibodies, wherein a Fab fragment of such antibodies inhibits alternative pathway hemolysis with $IC_{50}$ values less than 10 nM. In one embodiment, the invention provides anti-Factor D antibodies, wherein a Fab fragment of such antibodies inhibits alternative pathway hemolysis with $IC_{50}$ values less than 5 nM.

In one embodiment, the invention provides anti-Factor D antibodies, wherein a Fab fragment of such antibodies inhibits alternative pathway hemolysis with $IC_{50}$ values between 30 nM and 2 nM. In one embodiment, the invention provides anti-Factor D antibodies, wherein a Fab fragment of such antibodies inhibits alternative pathway hemolysis with $IC_{50}$ values between 25 nM and 7 nM. In one embodiment, the invention provides anti-Factor D antibodies, wherein a Fab fragment of such antibodies inhibits alternative pathway hemolysis with $IC_{50}$ values between 20 nM and 12 nM. In one embodiment, the invention provides anti-Factor D antibodies, wherein a Fab fragment of such antibodies inhibits alternative pathway hemolysis with $IC_{50}$ values between 30 nM and 15 nM. In one embodiment, the invention provides anti-Factor D antibodies, wherein a Fab fragment of such antibodies inhibits alternative pathway hemolysis with $IC_{50}$ values between 12 nM and 8 nM. In one embodiment, the invention provides anti-Factor D antibodies, wherein a Fab fragment of such antibodies inhibits alternative pathway hemolysis with $IC_{50}$ values between 7 nM and 2 nM. In one embodiment, the invention provides anti-Factor D antibodies, wherein a Fab fragment of such antibodies inhibits alternative pathway hemolysis with $IC_{50}$ values between 6 nM and 3 nM. In one embodiment, the invention provides anti-Factor D antibodies, wherein a Fab fragment of such antibodies inhibits alternative pathway hemolysis with $IC_{50}$ values between 8 nM and 5 nM. In one embodiment, the invention provides anti-Factor D antibodies, wherein a Fab fragment of such antibodies inhibits alternative pathway hemolysis with $IC_{50}$ values between 5 nM and 2 nM. In one embodiment, the invention provides anti-Factor D antibodies, wherein a Fab fragment of such antibodies inhibits alternative pathway hemolysis with $IC_{50}$ values between 10 nM and 5 nM. In one embodiment, the invention provides anti-Factor D antibodies, wherein a Fab fragment of such antibodies inhibits alternative pathway hemolysis with $IC5_{50}$ values between 8 nM and 2 nM. In one embodiment, the invention provides anti-Factor D antibodies, wherein a Fab fragment of such antibodies inhibits alternative pathway hemolysis with $IC_{50}$ values between 7 nM and 3 nM. In one embodiment, the invention provides anti-Factor D antibodies, wherein a Fab fragment of such antibodies inhibits alternative pathway hemolysis with $IC_{50}$ values between 6 nM and 4 nM. In another embodiment, the invention provides anti-Factor D antibodies, wherein a Fab fragment of such antibodies inhibits alternative pathway hemolysis with an $IC_{50}$ value of about 4.7 nM±0.6 nM. In another embodiment, the invention provides anti-Factor D antibodies, wherein a Fab fragment of such antibodies inhibits alternative pathway hemolysis with an $IC_{50}$ value of about 6.4 nM±0.6 nM. In another embodiment, the invention provides anti-Factor D antibodies, wherein a Fab fragment of such antibodies inhibits alternative pathway hemolysis with an $IC_{50}$ value of about 3.5 nM±0.5 nM. In another embodiment, the invention provides anti-Factor D antibodies, wherein a Fab fragment of such antibodies inhibits alternative pathway hemolysis with an $IC_{50}$ value of about 4.4 nM±1.5 nM. In another embodiment, the invention provides anti-Factor D antibodies, wherein a Fab fragment of such antibodies inhibits alternative pathway hemolysis with an $IC_{50}$ value of about 10.2 nM±0.8 nM. In another embodiment, the invention provides anti-Factor D antibodies, wherein a Fab fragment of such antibodies inhibits alternative pathway hemolysis with an $IC_{50}$ value of about 23.9 nM±5.0 nM.

In one embodiment, the invention provides anti-Factor D antibodies, wherein a Fab fragment of such antibodies inhibits alternative pathway hemolysis with $IC_{90}$ values less than 80 nM. In one embodiment, the invention provides anti-Factor D antibodies, wherein a Fab fragment of such antibodies inhibits alternative pathway hemolysis with $IC_{90}$ values less than 50 nM. In one embodiment, the invention provides anti-Factor D antibodies, wherein a Fab fragment of such antibodies inhibits alternative pathway hemolysis with $IC_{90}$ values less than 40 nM. In one embodiment, the invention provides anti-Factor D antibodies, wherein a Fab fragment of such antibodies inhibits alternative pathway hemolysis with $IC_{90}$ values less than 20 nM. In one embodiment, the invention provides anti-Factor D antibodies, wherein a Fab fragment of such antibodies inhibits alternative pathway hemolysis with $IC_{50}$ values less than 15 nM.

In one embodiment, the invention provides anti-Factor D antibodies, wherein a Fab fragment of such antibodies inhibits alternative pathway hemolysis with $IC_{90}$ values between 80 nM and 10 nM. In one embodiment, the invention provides anti-Factor D antibodies, wherein a Fab fragment of such antibodies inhibits alternative pathway hemolysis with $IC_{90}$ values between 75 nM and 15 nM. In one embodiment, the invention provides anti-Factor D antibodies, wherein a Fab fragment of such antibodies inhibits alternative pathway hemolysis with $IC_{90}$ values between 70 nM and 20 nM. In one embodiment, the invention provides anti-Factor D antibodies, wherein a Fab fragment of such antibodies inhibits alternative pathway hemolysis with $IC_{90}$ values between 65 nM and 25 nM. In one embodiment, the invention provides anti-Factor D antibodies, wherein a Fab fragment of such antibodies inhibits alternative pathway hemolysis with $IC_{90}$ values between 60 nM and 30 nM. In one embodiment, the invention provides anti-Factor D antibodies, wherein a Fab fragment of such antibodies inhibits alternative pathway hemolysis with $IC_{90}$ values between 55 nM and 35 nM. In one embodiment, the invention provides anti-Factor D antibodies, wherein a Fab fragment of such antibodies inhibits alternative pathway hemolysis with $IC_{90}$ values between 50 nM and 40 nM. In one embodiment, the invention provides anti-Factor D antibodies, wherein a Fab fragment of such antibodies inhibits alternative pathway hemolysis with $IC_{90}$ values between 80 nM and 70 nM. In one embodiment, the invention provides anti-Factor D antibodies, wherein a Fab fragment of such antibodies inhibits alternative pathway hemolysis with $IC_{90}$ values between 55 nM and 25 nM. In one embodiment, the invention provides anti-Factor D antibodies, wherein a Fab fragment of such antibodies inhibits alternative pathway hemolysis with $IC_{90}$ values between 16 nM and 12 nM. In another embodiment, the invention provides anti-Factor D antibodies, wherein a Fab fragment of such antibodies inhibits alternative pathway hemolysis with an $IC_{90}$ value of about 14.0 nM±1.0 nM. In another embodiment, the invention provides anti-Factor D antibodies, wherein a Fab fragment of such antibodies inhibits alternative pathway hemolysis with an $IC_{90}$ value of about 38.0 nM±11.0 nM. In another embodiment, the invention provides anti-Factor D antibodies, wherein a Fab fragment of such antibodies inhibits alternative pathway hemolysis with an $IC_{90}$ value of about 72.6 nM±4.8 nM.

In one embodiment, the invention concerns an anti-Factor D antibody wherein a Fab fragment of such antibodies inhibits alternative pathway hemolysis in an antibody to Factor D molar ratio of about 0.05:1 (0.05) to about 10:1 (10), or about 0.09:1 (0.09) to about 8:1 (8), or about 0.1:1 (0.1) to about 6:1 (6), or about 0.15:1 (0.15) to about 5:1 (5), or about 0.19:1 (0.19) to about 4:1 (4), or about 0.2:1 (0.2) to about 3:1 (3), or about 0.3:1 (0.3) to about 2:1 (2), or about 0.4:1 (0.4) to about 1:1 (1), or about 0.5:1 (0.5) to about 1:2 (0.5), or about 0.6:1 (0.6) to about 1:3 (0.33), or about 0.7:1 (0.7) to about 1:4 (0.25), or about 0.8:1 (0.8) to about 1:5 (0.2) or about 0.9:1 (0.9) to about 1:6 (0.17).

In one embodiment, the present invention includes fragments of humanized anti-Factor D antibodies (e.g. antigen-binding fragments). The antibody fragments of the present invention may, for example, be Fab, Fab', F(ab')$_2$, scFv, (scFv)$_2$, dAb, complementarity determining region (CDR) fragments, linear antibodies, single-chain antibody molecules, minibodies, diabodies, or multispecific antibodies formed from antibody fragments. In a further embodiment, the invention provides a humanized anti-Factor D antibody fragment (e.g. antigen-binding fragment) that is capable of penetrating substantially all of the retina. In an even further embodiment, the invention provides a humanized anti-Factor D antibody fragment (e.g. antigen-binding fragment) that is capable of penetrating throughout the entire thickness of the retina.

In one embodiment, the present invention includes anti-Factor D antibodies, wherein a Fab fragment of such antibodies have a half life of at least 3, 5, 7, 10 or 12 days after administration into a mammalian eye (e.g. human) via a single intravitreal injection. In another embodiment, the present invention includes humanized anti-Factor D antibodies, wherein a Fab fragment of such antibodies inhibits alternative pathway (AP) complement activation for at least 40, 45, 50, 55, 60, 65, 70, 75, 80, 85, 90, 95, 100, 105, 110 or 115 days after administration into a mammalian eye (e.g. human) via a single intravitreal injection. In another embodiment, the present invention includes humanized anti-Factor D antibodies, wherein the concentration of a Fab fragment of such antibodies that inhibits alternative pathway (AP) complement activation is maintained in retinal tissue for at least 40, 45, 50, 55, 60, 65, 70, 75, 80 or 85 days after administration into a mammalian eye (e.g. human) via a single intravitreal injection. In another embodiment, the present invention includes humanized anti-Factor D antibodies, wherein the concentration of a Fab fragment of such antibodies that inhibits alternative pathway (AP) complement activation is maintained in the vitreous humor for at least 80, 85, 90, 95, 100, 105, 110 or 115 days after administration into a mammalian eye (e.g. human) via a single intravitreal injection.

A Factor D antagonist can be administered alone or in combination with at least a second therapeutic compound. Administration of the Factor D antagonist and any second therapeutic compound can be done simultaneously, e.g., as a single composition or as two or more distinct compositions using the same or different administration routes. Alternatively, or additionally the administration can be done sequentially, in any order. In certain embodiments, intervals ranging from minutes to days, to weeks to months, can be present between the administrations of the two or more compositions. For example, the Factor D antagonist may be administered first, followed by the second therapeutic compound. However, simultaneous administration or administration of the second therapeutic compound prior to the Factor D antagonist is also contemplated. In one example, the Factor D antagonist is an anti-Factor D antibody. In a further example, the anti-Factor D antibody is an anti-Factor D antibody variant described herein. In one example, the second therapeutic compound is a HTRA1 antagonist. In a further example, the HTRA1 antagonist is an anti-HTRA1 antibody.

In one embodiment, the treatment of the present invention for complement-mediated disorders in a human subject with a complement-mediated disorder comprises administering to the subject an effective amount of a therapeutic compound, such as a Factor D antagonist, and further comprising administering to the subject an effective amount of a second therapeutic compound, that is a HTRA1 antagonist. In one example, the Factor D antagonist is an anti-Factor D antibody. In a further example, the anti-Factor D antibody is an anti-Factor D antibody variant described herein. In one example, the HTRA antagonist is an anti-HTRA1 antibody. In one example, the complement-mediated disorder is an complement-associated eye condition. In one example, the ocular disorder is age-related macular degeneration (AMD), including non-exudative (e.g intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

Combined administration herein includes co-administration, using separate formulations or a single pharmaceutical formulation, and consecutive administration in either order, wherein generally there is a time period while both (or all) active agents simultaneously exert their biological activities.

Pharmaceutical Formulations

Therapeutic formulations of the antibody or antibody variant thereof may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desireable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody, or antibody variant or fragment (e.g. antigen-binding fragment) thereof, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The compounds of the invention for prevention or treatment of an ocular disease or condition are typically administered by ocular, intraocular, and/or intravitreal injection, and/or juxtascleral injection, and/or subtenon injection, and/or superchoroidal injection and/or topical administration in the form of eye drops and/or ointment Such compounds of the invention may be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a min pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slit-lamp pressure, assessing intraocular inflammation, etc.

The amount of antibody or antibody variant thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In some embodiments, the antibody in the formulation is in an amount of about any of greater than 50 mg/mL, 75 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, 400 mg/mL, 425 mg/mL, 450 mg/mL, 475 mg/mL and 500 mg/mL. The antibody in the formulation may be in an amount of about any of between about 50 mg/mL and 500 mg/mL, 50 mg/mL and 300 mg/mL, 100 mg/mL and 500 mg/mL, 100 mg/mL and 300 mg/mL, 200 mg/mL and 500 mg/mL, 200 mg/mL and 400 mg/mL, or 250 mg/mL and 375 mg/mL.

In one embodiment, an aqueous solution of therapeutic polypeptide, antibody, or antibody variant thereof, or fragment thereof (e.g. antigen-binding fragment), is administered by subcutaneous injection. In another embodiment, an aqueous solution of therapeutic polypeptide, antibody, or antibody variant thereof, or fragment thereof (e.g. antigen-binding fragment) is administered by intravitreal injection. Each dose may range from about 0.5 µg to about 50 µg per kilogram of body weight, or more preferably, from about 3 µg to about 30 µg per kilogram body weight.

The dosing schedule for subcutaneous administration may vary form once a month to daily depending on a number of clinical factors, including the type of disease, severity of disease, and the subject's sensitivity to the therapeutic agent.

Articles of Manufacture and Kits

Another embodiment of the invention is an article of manufacture containing materials useful for the treatment, prevention and/or diagnosis of conditions targeted by the antibodies of the invention, or variants thereof or fragments thereof (e.g. antigen-binding fragments). For example, the invention concerns an article of manufacture containing materials useful for the treatment, prevention and/or diagnosis of complement-associated disorders. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosis of the complement-associated condition and may have a sterile access port (for example the container may be an intravenous solution bag or a vial having a stopper pierceable by a hypodermic injection needle). At least one active agent in the composition is an anti-Factor D antibody of the invention. The label or package insert indicates that the composition is useful for treatment, prevention and/or diagnosis of a particular condition.

Package insert refers to instructions customarily included in commercial packages of therapeutic products that contain information about the indications, usage, dosage, administration, contraindications and/or warnings concerning the use of such therapeutic products. In one embodiment, the label or package insert indicates that the composition is used for treating complement-associated disorders, such as, for example, any of the conditions listed before, including eye disorders e.g. image-related macular degeneration (AMD). The label or package insert will further comprise instructions for administering the antibody composition to the patient.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, kits are also provided that are useful for various purposes, e.g., for treatment, prevention and/or diagnosis of complement-associated disorders, for complement-associated hemolysis assays, for purification or immunoprecipitation of Factor D polypeptide from cells. For isolation and purification of Factor D polypeptide, the kit can contain an anti-Factor D antibody coupled to beads (e.g., sepharose beads). Kits can be provided which contain the antibodies for detection and quantitation of Factor D polypeptide in vitro, e.g., in an ELISA or a Western blot. As with the article of manufacture, the kit comprises a container and a label or package insert on or associated with the container. The container holds a composition comprising at least one anti-Factor antibody of the invention. Additional containers may be included that contain, e.g., diluents and buffers, control antibodies. The label or package insert may provide a description of the composition as well as instructions for the intended in vitro or detection use. The label or package insert may provide instructions for the administration (e.g. the antibody, or antibody fragment thereof (e.g. antigen-binding fragment) to a subject.

Therapeutic Uses

The antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or may be used to study toxicity of the antibody of interest. In each of these embodiments, dose escalation studies may be performed on the mammal.

The antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody, or antibody variant thereof or fragment thereof (e.g. antigen-binding fragment). Preferably the dosing is given by injections, most preferably intravenous or subcutaneous injections, depending in part on whether the administration is brief or chronic.

For the prevention or treatment of disease, the appropriate dosage of the antibody will depend on the type of disease to be treated, the severity and course of the disease, whether the antibody is administered for preventive or therapeutic purposes, previous therapy, the patient's clinical history and response to the antibody and the discretion of the attending physician.

Depending on the type and severity of the disease, about 0.1 mg/kg to 150 mg/kg (e.g., 0.1-20 mg/kg) of the antibody is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The antibody compositions may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody, or antibody variant thereof or fragment thereof (e.g. antigen-binding fragment), to be administered will be governed by such considerations, and is the minimum amount necessary to prevent, ameliorate, or treat a disease or disorder. The antibody, or antibody variant thereof or fragment thereof (e.g. antigen-binding fragment), need not be, but is optionally formulated with one or more agents currently used to prevent or treat the disorder in question. The effective amount of such other agents depends on the amount of antibody, or antibody variant thereof or fragment thereof (e.g. antigen-binding fragment), present in the formulation, the type of disorder or treatment, and other factors discussed above. These are generally used in the same dosages and with administration routes as used hereinbefore or about from 1 to 99% of the heretofore employed dosages.

The antibodies of the present invention which recognize Factor D as their target may be used to treat complement-mediated disorders. These disorders are associated with excessive or uncontrolled complement activation. They include: Complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease or condition is an inflammatory condition such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Recently there has been a strong correlation shown between complement activation and ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

EXAMPLES

The following examples are offered by way of illustration and not by way of limitation. Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1: Generation of Anti-Factor D Antibody Variants

Lampalizumab, a humanized anti-Factor D Fab fragment that potently inhibits Factor D and the alternative complement pathway, through binding to an exosite on factor D is currently in clinical development for the treatment of geographic atrophy (GA), an advanced form of dry AMD. Lampalizumab (FCFD4515S; hereinafter "aFD") is an antibody Fab fragment comprised of a 214 residue light chain (SEQ ID NO:1) and a 223 residue heavy chain (SEQ ID NO:2).

While results of a phase II human clinical trial in GA indicate that a treatment effect is obtained with monthly intravitreal injection of aFD, there exist incentives to use higher drug doses to achieve even better efficacy. Meanwhile, less frequent dosing would provide improved convenience to the patient, have potential benefits of decreased infection rate and increased clinical efficacy, and could facilitate treatment of patients with less advanced forms of dry AMD.

Efforts were made to further improve the wild type aFD (WT)'s physical and chemical stabilities, especially under low pH conditions and/or at high concentrations under neutral pH. Aspartic acid residues Asp-30 on the light chain and Asp-62 on the heavy chain (FIG. 1A) have been identified as prone to isomerization. Asp isomerization involves dehydration to form a cyclic imide intermediate (Asu) that is normally long-lived at pH<8 and detected as a basic peak upon ion exchange chromatography (IEC). Formation of the cyclic intermediate is accelerated at lower pH. Hydrolysis of the cyclic intermediate to form Asp or Iso-Asp, yielding the same charge state as the starting material and thus not detectable by IEC, is faster at higher pH. Isomerization of Asp-62 (Asp-61 according to Kabat numbering) does not appear to affect potency since it is not in contact with factor D in the crystal structure of the Fab:fD complex. Katschke et al. (2012) *J Biol. Chem.* 287:12886. Asp-30, together with light chain residues Asp-32 and Asp-92, make an electrostatic contact with basic residues on factor D. Isomerization of Asp-30 is quite rapid and presumed to account for an observed loss in potency of the antibody. Isomerization of Asp residues 32 and 92 could also have an effect on fD-binding but the rates are known to be very slow. Formation of the cyclic imide, or its subsequent hydrolysis to iso-aspartic acid, at position 30 could negatively impact antigen binding through perturbation of the electrostatic interaction. Antigen-binding measurements on the isolated basic fraction suggest that the cyclic intermediate form is fully active, consistent with iso-asp formation as the cause of loss in binding.

Asn-103 (Asn-101 according to Kabat numbering) on the heavy chain is susceptible to deamidation, a reaction that proceeds with higher rate at neutral as compared with slightly acidic pH (6-7). Deamidation can be detected as the appearance of an acidic peak upon IEC. Asn deamidation, like Asp isomerization, proceeds through a cyclic Asu intermediate. However, since formation of Asu from Asn only occurs at higher pH where Asu is hydrolyzed to form Asp or Iso-Asp, usually only the acidic peak is detected. The side chain of Asn-103 forms a hydrogen bond with factor D residue Arg-172. The effect of deamidation at this site, or formation of the cyclic imide intermediate, Asu, on antigen binding is unknown.

The aFD WT has a lower pI (7.1) than a typical humanized Fab (pI 8-9). The composition of CDR-L1 (FIG. 1A) results in a negative charge cluster on the VL domain. These features may affect solubility of the molecule, especially at low pH and low ionic strength. In addition, high concentration formulations of aFD WT, even at neutral pH and physiological ionic strength, may have the tendency to form non-covalent dimers at a faster rate at 37° C.

Several variants of aFD WT were produced for the purpose of improving stabilities. Point mutations were introduced by site-directed mutagenesis using the QuikChangeII® (Agilent) mutagenesis kit following the protocol supplied with the kit. Oligonucleotide primers specifying the required codon changes were synthesized. Plasmids with designed changes were identified and confirmed by DNA sequencing. For small scale expression and purification, DNA was transformed into *E. coli* strain 64B4. Single colonies were picked into 5 mL LB media (media prep code A2008) containing 50 μg/mL carbenecillin (media prep code A3232) and grown overnight in 14 mL culture tubes with shaking at 200 RPM in an Innova incubator at 37° C. These cultures were used to inoculate 250 mLs of complete soy crap media (media prep code A4564), 50 μg/mL carbenecillin, in a 1 L baffled shake flask. Cultures were grown overnight at 30° C. with shaking at 200 RPM and then harvested by centrifugation. The cell pellet was lysed using PopCulture media (Invitrogen), and Fabs purified on GRAVITRAP™ Protein G columns (GE Healthcare), following protocols supplied by the manufacturers. For larger scale production of Fabs, cell paste from 10 L fermentation of transformed cells was suspended in extraction buffer and homogenized using a microfluidizer. Fabs were captured by immunoaffinity chromatography on PROTEIN G-SEPHAROSE™ or kappa-select and eluted with a low pH buffer. The low pH eluate was adjusted to pH 5 and further purified by cation exchange chromatography on a S-SEPHAROSE™ column. Identities of the purified proteins were confirmed by mass spectroscopy and the pooled fractions were concentrated to about 10 mg/mL, and exchanged into PBS buffer (pH 7.3) (also referred to herein as "PBS"; 8 mM dibasic sodium phosphate ($Na_2HPO_4$), 2 mM monobasic potassium phosphate ($KH_2PO_4$), 140 mM NaCl, 2.7 mM KCl), via diafiltration.

Example 2: Bioactivities of the Anti-Factor D Antibody Variants

Promising single and combination mutants were tested for factor D (fD) binding affinity and ability to inhibit factor D activities.

a. Factor D Binding Affinity by Surface Plasmon Resonance (SPR) Measurements

Kinetics and binding constant $K_D$ for factor D binding to immobilized aFD WT and variants thereof was determined by surface plasmon resonance (SPR) measurements on a Biacore®T200 instrument. Antibody Fab fragments were immobilized on a Series S CM5 sensor chip using the anti-huFab capture kit (GE healthcare Cat. #28-9583-25) following a protocol described by the manufacturer. Kinetics of binding were calculated from sensorgrams recorded for injection of 60 μL aliquots of solutions of human factor D varied in concentration from 0.39 nM to 25 nM in 2-fold increments. The flow rate was 30 μL/min, the running buffer was HBS-P+, the temperature of analysis was 25° C., real-time reference cell subtraction was employed, and dissociation following factor D injection was followed for 10 minutes. After subtraction of the sensorgram observed for injection of running buffer, data were analyzed according to a 1:1 model using BiaEval software v4.1 (GE Healthcare) to extract the kinetics and affinity constants.

TABLE 1

Effect of mutations on affinity for factor D

| Mutant | SPR $K_D$ (pM) | Variant # |
|---|---|---|
| aFD WT | ≤10 | |
| VL-D28S | ≤10 | AFD.v1 |
| VL-D30E | ≤10 | AFD.v2 |
| VL-D31S | ≤10 | AFD.v3 |
| VL-D32S | 26 | AFD.v4 |
| VL-D28S:D31S:D32S | 280 | AFD.v5 |
| VL-D30E:D31S VH-D62E ("TM") | ≤10 | AFD.v6 |
| VL-D30E:D31S VH-D62E VL-D92E ("TM.D92E") | ≤10 | AFD.v7 |
| VL-D28S:D30E:D31S VH-D62E ("SIESD") | 16.7 ± 4.4 | AFD.v8 |
| VL-D28S:D30E:D31S VH-D62E VL-N34S | 30 | AFD.v9 |
| VL-D28S:D30E:D31S VH-D62E VL-D92E | 70 | AFD.v10 |

TABLE 1-continued

Effect of mutations on affinity for factor D

| Mutant | SPR $K_D$ (pM) | Variant # |
|---|---|---|
| VL-D28S:D30E:D31S:D92E VH-D62E:N103S | 102 | AFD.v15 |
| VL-D28S:D30E:D31S VH-D62E VH-N52S | 70 | AFD.v11 |
| VL-D28S:D30E:D31S VH-D62E VH-N103D | 23 | AFD.v12 |
| VL-D28S:D30E:D31S VH-D62E VH-N103Q | 60 | AFD.v13 |
| VL-D28S:D30E:D31S VH-D62E VH-N103S ("SIESD.N103S") | 25.6 ± 6.3 | AFD.v14 |

Mutants are named and numbered based on location in aFD WT's light chain variable domain (VL; SEQ ID NO:3) and heavy chain variable domain (VH; SEQ ID NO:4). Single letter code for the wild-type residue followed by sequence position followed by single letter code for the substituted amino acid. Multiple changes on the same domain are separated by a colon.

As shown in Table 1, aFD WT has a high affinity for fD, at the limit (~10 pM KD) that can be determined with SPR technology. Aspartic acid residues 28, 30, and 31 in CDR-L1 could be individually substituted with Ser, Glu, and Ser, respectively, without apparent effect on affinity for fD (Table 1). In contrast, replacement of CDR-L1 Asp32 with Ser resulted in a significant loss in fD-binding whether tested individually (AFD.v4) or in combination with D28S and D31S mutants (AFD.v5). fD affinities equivalent to the wild-type molecule were determined for a triple mutant ("TM" (AFD.v6)) combining VL-D30E, D31S and VH-D62E and for a quad mutant (TM.D92E (AFD.v7)) which adds VL-D92E to TM (AFD.v6). The VH-D62E is a replacement at a site that undergoes isomerization without apparent effect on fD-binding; VL-Asp92 is an antigen contact residue with a slow rate of isomerization. The quad mutant "SIESD" (AFD.v8) combining VL-D28S, D30E, D31S and VH-D62E shows a small (~2-fold) loss in affinity for fD. In the context of SIESD (AFD.v8), the VL-D92E replacement resulted in a further loss in affinity for fD (see AFD.v10 (SIESD.D92E in Table 1)).

Potential sites of deamidation were tested for replacement with other residues. Both VL-N34 and VH-N52 are in contact with fD in the co-crystal structure but neither of these sites show significant rates of deamidation under neutral pH conditions. Ser substitution at these sites resulted in a loss in affinity (Table 1; AFD.v9 and AFD.v11). VH residue Asn-103 does contact fD and has a measureable rate of deamidation in PBS. Substitution of Asn-103 with Asp or Ser in the context of SIESD (AFD.v8) resulted in small, acceptable losses in affinity for fD (see AFD.v12 (SIESD.N103D) and AFD.v14 (SIESD.N103S)) (Table 1). A Gln substitution for Asn-103 resulted in a larger decrease in binding affinity (see AFD.v13 (SIESD.N103Q) (Table 1). Similar to SIESD (AFD.v8), SIESD.N103S.D92E (AFD.v15) which added VL-D92E to the penta mutant SIESD.N103S (AFD.v14) resulted in a further 4-fold decrease in affinity for fD.

b. Factor D Inhibition Assays aFD WT and variants were tested for their abilities to inhibit Factor D-induced complement activation, using an alternative pathway (AP) hemolysis assay. The AP hemolysis assay using rabbit erythrocytes (Er) has been previously described. Pangburn (1998), *Methods. Enzymol.* 162:639; Katschke et al. (2009) *J. Biol. Chem.* 284:10473. Er (Colorado Serum) were washed three times with 0.5% bovine skin gelatin in veronal buffer (GVB) and re-suspended. Dilutions of aFDs were prepared at a 2× concentration and added to 96-well polypropylene plates. Er suspension were mixed with GVB/0.1M EGTA/0.1M $MgCl_2$ and added to the plates. Complement activation was initiated by the addition of C1q-depleted human serum to avoid any complement activation through the classical pathway (CompTech; diluted 1:3 in GVB). After a 30 minute incubation at room temperature, the reaction stopped by adding 10 mM EDTA in GVB. The plates were centrifuged and the supernatants transferred. The absorbance of the supernatant was read at 412 nm. The aFD concentrations causing half-maximal inhibition (IC50) were determined by a nonlinear regression analysis.

TABLE 2

Inhibitory potency of aFD variants

| Sample | IC50 (nM)* AP Hemolysis |
|---|---|
| WT (aFD WT) | 3.4 |
| SIESD (AFD.v8) | 4.2 |
| SIESD.N103S (AFD.v14) | 4.1 |
| TM.D92E (AFD.v7) | 3.8 |

*RSE = ±30%

As shown in Table 2, variants SIESD (AFD.v8), SIESD.N103S (AFD.v14), and TM.D92E (AFD.v7) have potencies for inhibiting fD-dependent complement activation activities that are equivalent to aFD WT, given the standard error in IC50 measurement of ±30%.

c. Binding Capacity Over Prolonged Time

Figure 2A:
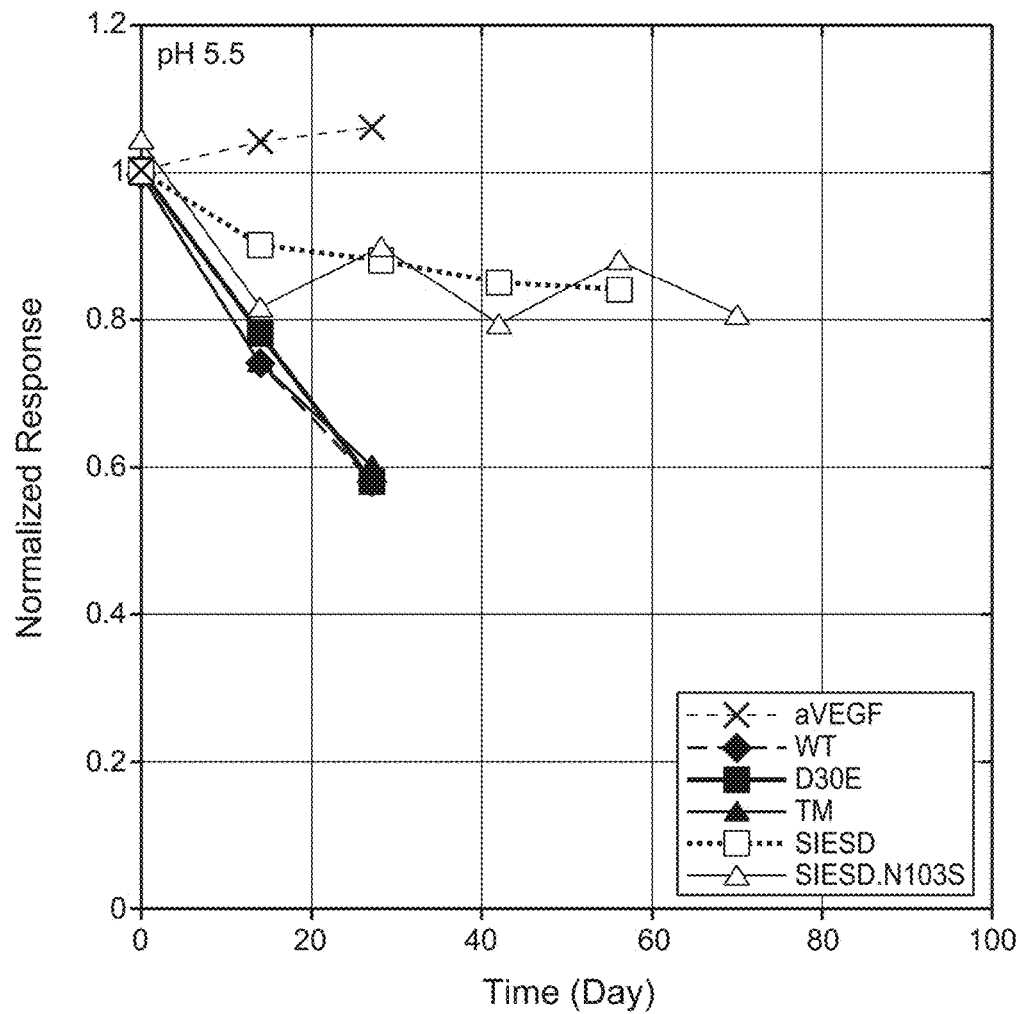
FIGS. 2A-2C illustrate antigen binding capacity of various antibody Fab fragments over prolonged time under defined conditions (2A: Fab protein concentration of 10 mg/mL in pH5.5 buffer; 2B: Fab protein concentration of 100 mg/ml in PBS; 2C: Fab protein concentration of 100 mg/ml in PBS).
Figure 2B:
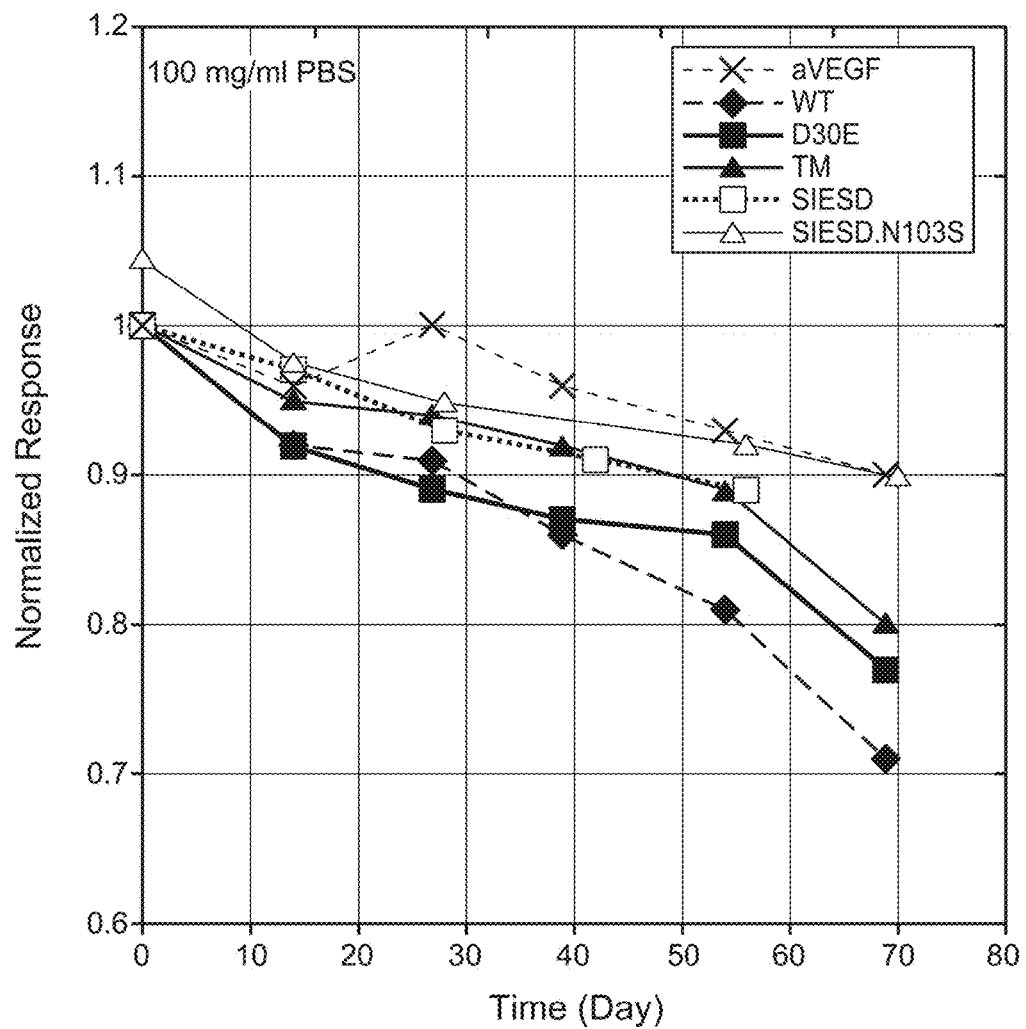
Figure 2C:
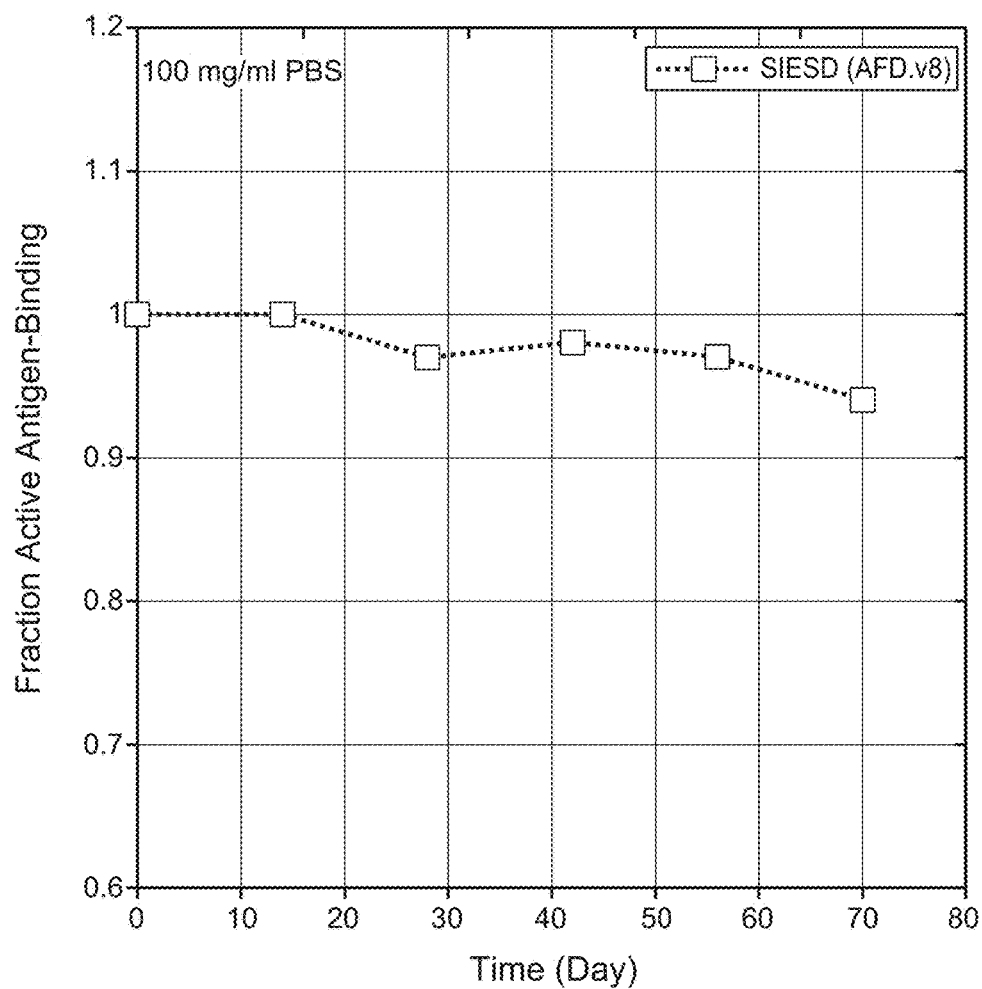

SPR was also used to measure total binding of aFD variants to fD over time under defined conditions. The standard error in these measurements is ±10%. FIG. 2A shows that at pH 5.5, loss in binding was about 40% in one month for aFD WT and aFD variants, D30E (AFD.v2) and TM (AFD.v6), whereas loss of binding for SIESD (AFD.v8) and SIESD.N103S (AFD.v14) was smaller at about 15%, even for prolonged period of time (70 days). As a comparison, an anti-VEGF antibody Fab fragment (aVEGF) showed no loss in binding over 70 days. Addition of salt to the pH 7.4 condition seemed to enhance the rate of loss in binding for aFD WT and aVEGF (data not shown). As shown in FIG. 2B, in the presence of PBS (with Fab protein concentration at 100 mg/ml), D30E (AFD.v2) and TM (AFD.v6) had equivalent rates of loss in binding that was slower than observed for aFD WT. The loss in binding after 10 weeks at 37° C. was about 30% for aFD WT, and 20% for D30E (AFD.v2) and TM (AFD.v6) variants of anti-factor D. Loss in binding after 10 weeks at 37° C. was only 10% for SIESD.N103S (AFD.14; FIG. 2B), no greater than the experimental error, and equivalent to that observed for aVEGF under the same conditions. The thermal stress in PBS experiment at 100 mg/mL Fab concentration was repeated for SIESD (AFD.v8) in order to collect data out to 70 days. As shown in FIG. 2C, loss in binding at 70 days was less than 10% for SIESD (AFD.v8).

Example 3. Anti-Factor D Antibody Variants with Improved Stability

Based on the affinity assays above, several single and combination anti-Factor D antibody variants were selected for further stability analysis.

a. Solubility

Samples were initially tested for solubility at low ionic strength and pH 6. Samples were first prepared in 20 mM His-HCl pH 5 buffer by concentration to ~100 mg/mL using AMICON™ Centriprep YM-10 centrifugal filter units. These solutions at pH 5 and low ionic strength did not show turbidity upon visual inspection. Samples were centrifuged at 14,000×g for 10 min to pellet any insoluble material. No pellet was observed, and the protein concentration of the solution was determined by UV absorbance measurements. Samples (~1 mL) were placed in SLIDE-A-LYZER™ cassettes of 10 K MWCO (Pierce) and dialyzed overnight at 4° C. versus 1 L of 20 mM His buffer, pH 6, followed by visual inspection for turbidity. Photographs of the solutions were taken and are provided in FIG. 6. At pH 6 and low ionic strength conditions (~100 mg/ml in 20 mM His-HCl, pH 6), aFD WT and D30E (AFD.v2) solutions were noticeably turbid, TM (AFD.v6) solution was less turbid and the solution of SIESD (AFD.v8) was clear (FIG. 6). After centrifugation as above, whereby large pellets were visually observed for aFD WT and AFD.v2, a smaller pellet for TM (AFD.v6), and no pellet for SIESD (AFD.v8), protein concentrations of the supernatants were determined by UV absorbance measurements (Table 3). aFD WT and D30E (AFD.v2) showed solubilities of less than 50 mg/ml, TM (AFD.v6) showed solubility approaching 100 mg/mL and SIESD (AFD.v8) was fully soluble under these conditions. The small reduction in protein concentration for SIESD (AFD.v8) after pH 6 dialysis relative to the pH 5 starting concentration reflects a dilution effect upon dialysis rather than precipitation of AFD.v8 since no pellet was observed upon centrifugation.

TABLE 3

Solubility of AFD Variants (~100 mg/ml in 20 mM His-HCl, pH 6)

| AFD Variant # | Concentration at pH 5, before pH 6 dialysis (mg/ml) | Concentration after pH 6 dialysis at 4° C. and centrifugation (mg/ml) |
|---|---|---|
| aFD WT | 102 | 40 |
| AFD.v2 (D30E) | 102 | 14 |
| AFD.v6 (TM) | 102 | 92 |
| AFD.v8 (SIESD) | 100 | 94 |

Further variants AFD.v3, AFD.v12, AFD.v13 and AFD.v14 were tested in no salt solubility tests. After dialysis into pH 6 buffer at 4° C. and incubation overnight at 37° C., all of the protein solutions except aFD WT were clear (FIG. 7). Measurements of protein concentration after 37° C. incubation and centrifugation (Table 4) indicate that all the variants were more soluble than aFD WT. The turbid solution of aFD WT (FIG. 7, top row) became clear when subsequently dialyzed versus PBS (pH 7.3), a salt (NaCl) containing buffer, which suggests that the precipitation was reversible with salt addition and/or increase in pH (FIG. 7, bottom row). The solubility data on AFD.v3 indicates that the single amino acid change D31S, removal of 1 negatively charged residue, can result in increased solubility. The further amino acid changes in AFD.v8, AFD.v12, AFD.v13 and AFD.v14 also result in increased solubility.

TABLE 4

Solubility of AFD Variants at pH 6, no salt

| Condition | aFD WT | AFD.v3 (D31S) | AFD.v8 (SIESD) | AFD.v12 (SIESD. N103D) | AFD.v13 (SIESD. N103Q) | AFD.v14 (SIESD. N103S) |
|---|---|---|---|---|---|---|
| Concentration at pH 5, before pH 6 dialysis (mg/ml) | 112 | 106 | 120 | 118 | 109 | 103 |
| Concentration after pH 6 dialysis at 4° C., incubation at 37° C. overnight and centrifugation (mg/ml) | 63 | 97 | 99 | 94 | 96 | 80 | aFD WT, SIESD (AFD.v8) and SIESD.N103S (AFD.v14) were also tested for solubility under conditions of physiological pH (pH 7.3) and ionic strength. For solubility testing under physiological pH and ionic strength, samples were dialyzed overnight versus PBS, and then concentrated to 227-372 mg/mL using AMICON™ Centriprep YM-10 centrifugal filter units. After overnight incubation at 4° C., samples were visually inspected for turbidity, a portion was centrifuged to remove precipitated protein and the concentration of protein was determined by UV absorbance measurements and reported in Table 5. Prior to centrifugation, the aFD WT sample was turbid whereas the solutions of SIESD (AFD.v8) and SIESD.N103S (AFD.v14) were clear (aFD WT, AFD.v8 and AFD.v14 shown in FIG. 8). The concentration of AFD.v14 was 344 mg/mL for the solution in the photograph (FIG. 8) which was then further concentrated to 372 mg/mL. The concentration of AFD.v8 was 269 mg/ml for the solution in FIG. 8. The concentration of aFD WT was 227 mg/ml for the solution in FIG. 8. After centrifugation, a pellet was observed with the aFD WT solution, but no pellet was observed for the solutions of SIESD (AFD.v8) and SIESD.N103S (AFD.v14). The protein concentration data (Table 5) indicated that aFD WT can only be concentrated to 227 mg/mL in PBS before precipitation is observed, whereas the solubility limits are higher for SIESD (AFD.v8) (≥269 mg/mL) and SIESD.N103S (AFD.v14) (≥372 mg/mL). Since no precipitate was observed for SIESD (AFD.v8) at 269 mg/mL, and no attempt was made to further concentrate the solution, this is the lower limit of solubility for this variant in PBS. Similarly, the lower limit of solubility for SIESD.N103S (AFD.v14) in PBS is 372 mg/mL. The 269 mg/mL solution of SIESD (AFD.v8) in PBS remained clear after 4 weeks of incubation at 2-8° C. Similarly, there was not any apparent increase in turbidity for the 372 mg/mL solution of SIESD.N103S (AFD.v14) in PBS after 3 weeks of incubation at 2-8° C. At this concentration, there was a very small change in % aggregate as measured using size-exclusion chromatography (SEC) (FIG. 9), increasing from 0.9% to 2.1% in 3 weeks at 2-8° C. (SEC data prior to 3 week incubation (0.9% aggregate) is shown in FIG. 9; SEC data after 3 week incubation is data not shown).

TABLE 5

Solubility of AFD Variants (in PBS (pH 7.3))

| AFD Variant # | Isoelectric point (pI)* | Concentration after centrifugation (mg/ml) |
| --- | --- | --- |
| aFD WT | 7.1 | 227 |
| SIESD (AFD.v8) | 7.3 | 269 |
| SIESD.N103S (AFD.v14) | 7.4 | 372 |

*pI values were determined by imaged capillary isoelectric focusing (icIEF)

Solubilities of variants SIESD (AFD.v8) and SIESD.N103S (AFD.v14) were also compared in a buffer of pH 5.5 (20 mM HCl pH 5.5), and varied NaCl concentration, that may be representative of formulations used for drugs administered via intravitreal injection. Solutions of about 100 mg/mL protein concentration were prepared and dialyzed against a test buffer. These solutions were then concentrated using AMICON™ Centriprep YM-10 centrifugal filter units. The concentrations obtained whereby the solutions remained visibly clear at ambient temperature are reported in Table 6. SIESD (AFD.v8) has high solubility, up to 314 mg/mL, at pH 5.5 and low NaCl concentration. High concentrations of SIESD.N103S (AFD.v14) were also achievable, up to 278 mg/mL with addition of 100 mM NaCl.

TABLE 6

Solubility of AFD variants at pH 5.5 (20 mM His-HCl pH 5.5) and varied NaCl concentration

| NaCl Concentration, mM | SIESD(AFD.v8) mg/mL | SIESD.N103S(AFD.v14) mg/mL |
|---|---|---|
| 0 | 314 | NT |
| 50 | 290 | 200 |
| 100 | NT | 278 |

NT = not tested

Although SIESD.N103S (AFD.v14) has two (2) fewer negatively charged residues in comparison to aFD WT, these changes in charge do not result in a significant change in pI (Table 5), as measured by imaged capillary isoelectric focusing (iCIEF) (Salas-Solano et al, *J. Sep Sci,* 35(22): 3124 (2012)). Proteins are expected to have minimum solubility at pH values close to the pI (Green, A. A., *J. Biol. Chem.,* 93: 517-542 (1931)). For SIESD.N103S (AFD.v14) the increased solubility in PBS (pH 7.3) is not correlated with change in pI. Rather, the Asp to Ser amino acid changes in LC-CDR-L1 (VL-D28S and D31S) appear to alter the charge distribution on the surface of the molecule.

b. Isomerization and Deamidation

To simulate the exposure of variants to a variety of conditions that may be found in long-acting delivery systems, antibodies were stressed under varied pH and salt conditions for several weeks at 37° C. Specifically, antibodies were evaluated in the following five different formulations:

Formulation 1: 10 mg/mL, 10 mM phosphate buffer at pH 2.5,

Formulation 2: 10 mg/mL, 10 mM histidine HCl at pH 5.5,

Formulation 3: 10 mg/mL, 10 mM phosphate buffer at pH 7.4 ("low salt"),

Formulation 4: 10 mg/mL, pH 7.4 PBS ("high salt"; 10 mM phosphate, 137 mM NaCl)

Formulation 5: 100 mg/mL, pH 7.4 PBS

All solutions had 0.02% PS20, were incubated at 37° C. and were sampled every 2 weeks. The low salt conditions (pH 2.5, 5.5, and 7.4) were to evaluate the effect of chemical degradation in liquid formulations. PBS was used as a mimic of the pH and ionic strength of human vitreous. In addition, comparing the 10 mM phosphate, pH 7.4, to PBS condition should reveal ionic strength effects on chemical and physical stability. The PBS samples were buffer exchanged regularly during incubation to simulate the exchange of vitreous. The wild type aFD ("WT" or "aFD WT") and aVEGF were evaluated in all 5 conditions. D30E (AFD.v2) and TM (AFD.v6) variants were tested in all formulations except number 4. SIESD (AFD.v8) and SIESD.N103S (AFD.v14) were tested in formulations 2 and 5.

The chemical degradation being quantified were deamidation, which is characterized by the formation of acidic peaks, and the dehydration step of isomerization, which is characterized by the formation of a long-lived succinimide (Asu) intermediate detected as basic peaks. Anionic exchange chromatography (Dionex PROPAC™ SAX-10 columns) (IEC) was used to quantify the appearance of Asn deamidated and Asp dehydrated species within antibody samples in different formulations.

For all conditions tested, aFD WT shows the greatest rate in loss of main peak and increase in basic peak amongst the tested antibodies. This is most noticeable at pH 5.5 where aVEGF, D30E (AFD.v2), TM (AFD.v6), SIESD (AFD.v8), and SIESD.N103S (AFD.v14) all show significantly lower rates of main peak loss than aFD WT, see FIG. 3A. SIESD.N103S (AFD.v14) shows the slowest rate of main peak loss with the rate similar to aVEGF at pH 5.5 (FIG. 3A) and even slower than aVEGF in PBS (FIG. 3B). As shown in FIG. 4B (100 mg/ml of Fab in PBS (pH 7.3), D30E (AFD.v2) shows approximately half the rate of basic peak formation as aFD WT whereas TM (AFD.v6), SIESD (AFD.v8), and SIESD.N103S (AFD.14) show negligible basic peak formation. In contrast, as shown in FIG. 4B (100 mg/ml of Fab in PBS (pH 7.3), the rate of acidic peak generation for aFD WT and D30E (AFD.v2) are equivalent for PBS condition and about 2-fold slower than determined for TM (AFD.v6) and SIESD (AFD.v8). Acidic peak formation for SIESD.N103S (AFD.v14) in PBS is essentially negligible.

c. Aggregation

Size exclusion chromatography (SEC) was utilized to quantify the formation of aggregates and monomers for tested antibodies. Column used was TSK-GEL Super SW2000 (Tosoh Biosci.). Materials and conditions were used based on the manufacturer's instructions (www.tskgel.com).

The % monomers over time based on SEC data for tested antibodies at 100 mg/ml of Fab formulated in PBS at 37° C. are shown in FIG. 5. AFD WT shows a decrease in monomer peak fraction by 3-4% per month. AFD.v2 (D30E) which has no change in negative charge compared to aFD WT shows a similar rate of monomer loss. AFD.v6, AFD.v8 and AFD.v14 show a decreased rate of monomer loss. The differences in monomer content at day zero reflect minor variations in the homogeneity of the purified preparations. The aggregation rate for D30E (AFD.v2) and TM (AFD.v6)

is comparable at pH 5.5 and 7.4 (no salt) at 10 mg/ml protein concentration. The addition of salt at pH 7.4 does not affect the rate of aggregation for aFD variants but it doubles the rate of aggregation for aVEGF. Aggregation is protein concentration dependent since increasing the concentration from 10 mg/mL to 100 mg/mL in PBS increases the rate of aggregation for all samples tested (Table 7). Aggregation at 10 mg/mL concentration in 10 mM phosphate buffer pH 7.4 and no NaCl, and at 10 mg/mL concentration in PBS was minimal (Table 7). At 100 mg/mL concentration in PBS, the loss in monomer is much greater for aFD WT and D30E (AFD.v2) (5.8% and 7.3% in 40 days, respectively) than for aVEGF, TM (AFD.v6), SIESD (AFD.v8), and SIESD.N103S (AFD.v14) (1.8%, 1.5%, 0.7%, and 1.5% in 40 days, respectively) at 100 mg/mL in PBS at 37° C. These data suggest that AFD.v6, AFD.v8 and AFD.v14 have less aggregation than aFD WT and AFD.v2 and may be more suitable as therapeutics as they may be less prone to in vivo immunogenicity.

TABLE 7

Effect of salt and protein concentration on aggregation of aFD variants and aVEGF as determined by SEC at 40 days

| Formulation Conditions | Decrease in % Monomer after 40 Days | | | | | |
|---|---|---|---|---|---|---|
| | aFD WT | D30E (AFD.v2) | TM (AFD.v6) | SIESD (AFD.v8) | SIESD.N103S (AFD.v14) | aVEGF |
| 10 mg/mL in 10 mM sodium phosphate pH 7.4 | 1.6 | 2.1 | .9 | | | .36 |
| 10 mg/mL in PBS | 1.5 | | .8 | | | .63 |
| 100 mg/mL in PBS | 5.8 | 7.3 | 1.5 | 0.7 | 1.5 | 1.78 |

To detect fragmentation formed as a function of pH, capillary electrophoresis sodium dodecyl sulfate (CE-SDS) was performed using a Beckman PA800 System with an uncoated fused-silica capillary with a 50 μm internal diameter (Polymicro Technologies, Inc). Samples were prepared by a Beckman Coulter NXp Liquid Handling Robot with automation equivalent to Q12695. Samples were injected into the capillary at a voltage of 5 kV for 15 seconds and then mobilized at a voltage of 15 kV for 30 minutes. All samples were run at ambient temperature. The electropherograms of all tested antibodies are similar to that of aFD WT. Only at pH 2.5 was significant fragmentation observed. At no condition were higher molecular weight species observed, indicating that any aggregates formed are SDS-dissociable and not covalently linked.

The above stability results show that the triple (TM (AFD.v6)) and quad (SIESD (AFD.v8)) mutant variants of anti-Factor D have chemical stability that is significantly improved over aFD WT or D30E (AFD.v2). In this series, SIESD.N103S (AFD.14) has the highest chemical stability at pH 5.5 and in PBS, similar to the stability of aVEGF. Both isomerization and deamidation sites have been removed and solubility at neutral pH has been increased while maintaining the fD binding affinity. Based on the above findings, the selected anti-Factor D variants described herein, particularly the SIESD (AFD.v8) and SIESD.N103S (AFD.v14) variants, are suitable for both high concentration formulation and for long acting delivery via, e.g., a port delivery system (PDS) device. For example, long acting delivery using a permanent, refillable device, such as a port delivery system may require high concentration formulation and low tendency to aggregate under physiological conditions of pH (~7.3) and ionic strength (150 mM NaCl).

List of HVR Sequences (Substitutions in Variants are Underlined)

| SEQ ID NO: | Description | Sequence |
|---|---|---|
| 5 | HVR-L1 of WT | ITSTDIDDDMN |
| 6 | HVR-L2 of WT/TM (AFD.v6)/ TM.92E (AFD.v7)/SIESD (AFD.v8)/SIESD.N103S (AFD.v14) | GGNTLRP |
| 7 | HVR-L3 of WT/TM (AFD.v6)/ SIESD(AFD.v8)/SIESD.N103S (AFD.v14) | LQSDSLPYT |
| 8 | HVR-H1 of WT/TM (AFD.v6)/ TM.92E (AFD.v7)/SIESD (AFD.v8)/SIESD.N103S (AFD.v14) | GYTFTNYGMN |
| 9 | HVR-H2 of WT | WINTYTGETTYADDFKG |
| 10 | HVR-H3 of WT/TM (AFD.v6)/ TM.92E (AFD.v7)/SIESD (AFD.v8) | EEGGVNN |
| 11 | HVR-L1 of TM (AFD.v6)/ TM.D92E(AFD.v7) | ITSTDI__ES__DMN |
| 12 | HVR-H2 of TM (AFD.v6)/ TM.92E(AFD.v7)/SIESD (AFD.v8)/SIESD.N103S (AFD.v14) | WINTYTGETTYA__E__DFKG |
| 13 | HVR-L3 of TM.D92E (AFD.v7) | LQS__E__SLPYT |
| 14 | HVR-L1 of SIESD (AFD.v8)/SIESD.N103S (AFD.v14) | ITST__SIES__DMN |
| 15 | HVR-H3 of SIESD.N103S (AFD.v14) | EGGVS__N__ |

Example 4. Anti-Factor D Antibody Variants Further Modified for Polymer Conjugation The aFD WT and variants described in the above Examples are Fab fragments. While the variable domains of their light and heavy chains (VL and VH) vary in sequences as shown in FIG. 1B, their constant domains CL and CH1 remain the same. In particular, the CH1 domain of the heavy chain ends at the Threonine residue as shown in FIG. 1A (SEQ ID NO:2) FIG. 1C (SEQ ID NO: 27) and FIG. 1D (SEQ ID NO: 29). In order to prepare the aFD variants for polymer conjugation such as PEGylation, the heavy chains of the Fab fragments were further modified by adding the first cysteine residue from the hinge region of the Fab' counterpart (e.g. Cys-modified HC for AFD.v8 (SEQ ID NO: 30) and Cys-modified HC for AFD.v14 (SEQ ID NO: 32)), so that the added cysteine serves as the attachment site of PEG polymer. The resulting fragment can therefore be conjugated with one PEG molecule. The heavy chains of the Fab fragments were also modified by adding the first four residues from the hinge region of the Fab' counterpart, namely Cys-Pro-Pro-Cys (SEQ ID NO: 21) (e.g. Cys-Pro-Pro-Cys-modified HC for AFD.v8 (SEQ ID NO: 31) and Cys-Pro-Pro-Cys-modified HC for AFD.v14 (SEQ ID NO: 33)), so that the two added Cys both serve as attachment sites for PEG, resulting in a modified aFD Fab fragment capable of attaching two PEG molecules.

Example 5: Rabbit pK for AFD.v8/v14

In vivo pK studies for AFD.v8 and AFD.v14 was tested in rabbits. pK parameters were determined from single dose experiments because humanized antibodies are immunogenic in rabbits upon repeat dosing or when exposure is increased through sustained delivery formulations.

The animals' care was in accordance with Genentech Institutional Animal Care and Use Committee guidelines. Naïve New Zealand White (NZW) rabbits (41 male animals; 3.1 kg to 4.1 kg and approximately 4 months of age at the time of dosing) were assigned to dose groups and dosed with the test items at Charles River Laboratories.

SIESD (AFD.v8), SIESD.N103S (AFD.v14) or ranibizumab were administered via a single bilateral intravitreal injection to rabbits and observed for up to 27 days. Topical antibiotic (tobramicin ophthalmic ointment) was applied to both eyes twice on the day before treatment, immediately following the injection, and twice on the day following the injection, with the exception of animals sent to necropsy on Days 1 and 2. Prior to dosing, mydriatic drops (1% tropicamide) were applied to each eye for full pupil dilation. Animals were sedated with isoflurane/oxygen gas prior to and during the procedure. ALCAINE™ (0.5%) topical local anesthetic was also applied to each eye prior to injection. The conjunctivae was flushed with benzalkonium chloride (Zephiran™) diluted in sterile water, U.S.P. to 1:10,000 (v/v).

Syringes were filled under a laminar flow hood immediately prior to dosing. Fabs were administered by a single 30 µL intravitreal injection (0.3 mg dose) to both eyes in all animals. Doses were administered by a board-certified veterinary ophthalmologist using sterilized 100 µL Hamilton Luer Lock syringes with a 30-gauge×½" needle. In order to mimic clinical dosing, eyes were dosed in the infero-temporal quadrants, i.e. in 5 o'clock and 7 o'clock positions for the left and right eyes, respectively (when facing the animal). The eyes were examined by slit-lamp biomicroscopy and/or indirect ophthalmoscopy immediately following treatment.

All animals underwent exsanguination by incision of the axillary or femoral arteries following anesthesia by intravenous injection of sodium pentobarbital. Aqueous humor, vitreous humor and retina tissue were collected, snap frozen in liquid nitrogen and stored at −80° C. Antibody Fab in retina was extracted by homogenization in 50 mM Tris-HCl pH 8.0, 1 M NaCl. Determination of vitreous and retinal concentrations of test articles was by GRIP ELISA as described below. Values below the LLOQ were not used in pharmacokinetic analysis or for graphical or summary purposes. Pharmacokinetic parameters were determined by non-compartmental analysis with nominal time and dose (Phoenix WinNonlin, Pharsight Corp, Mountain View, Calif.).

Analyses of SIESD (AFD.v8), SIESD.N103S (AFD.v14) and ranibizumab were done in the generic immunoglobulin pharmacokinetic (GRIP) ELISA with the following exceptions. Sheep anti-human-IgG (The Binding Site; San Diego, Calif.) was diluted to 1000 ng/mL in 0.5 M carbonate/bicarbonate, pH 9.6, and coated onto 384-well ELISA plates (Nunc; Neptune, N.J.) during an overnight incubation at 4° C. Plates were washed with PBS plus 0.05% TWEEN-20™ non-ionic detergent and blocked during a 1- to 2-hour incubation with PBS plus 0.5% bovine serum albumin (BSA). This and all subsequent incubations were performed at room temperature with gentle agitation. The standard curves were prepared by serially diluting AFD.v8, AFD.v14 or ranibizumab from 40-0.625 ng/mL in assay buffer (PBS, 0.5% BSA, 15 ppm Proclin, 0.05% TWEEN-20™ non-ionic detergent, 0.25% CHAPS, 5 mM EDTA, 0.35M NaCl, (pH 7.4)). The rabbit vitreous or retinal homogenate samples were diluted a minimum of 1:100 or 1:50, respectively, in assay buffer. The diluted standards, controls, and samples were then incubated on the washed plates for 1-2 hours. Following a wash step, plate-bound AFD.v8, AFD.v14 or ranibizumab was detected during a 1.5 hour incubation with HRP-conjugated sheep anti-human IgG mAb (Bethyl Laboratories Inc; Montgomery, Tex.) diluted to 83.3 ng/mL in assay diluent (PBS+0.5% BSA+0.05% TWEEN-20™ non-ionic detergent+10 ppm Proclin). After a final wash, tetramethyl benzidine peroxidase substrate (Moss, Inc., Pasadena, Md.) was added, color was developed for 10-15 minutes, and the reaction was stopped with 1 M phosphoric acid. The plates were read at 450 nm with a 620 nm reference using a microplate reader (Multiscan Ascent, Thermo Fischer; Waltham, Mass.). The concentrations of AFD.v8, AFD.v14 or ranibizumab were calculated from a four-parameter fit of the respective standard curve using in-house Excel-based software. Taking into account the minimum dilution in vitreous or retinal homogenate, the minimum quantifiable concentration of AFD.v8, AFD.v14 or ranibizumab in rabbit vitreous or retinal homogenate was 62.5 ng/mL or 31.25 ng/mL, respectively.

Time-dependent concentration curves observed for intravitreal injection of 0.3 mg SIESD (AFD.v8), SIESD.N103S (AFD.v14), or a comparator dose of ranibizumab (anti-VEGF), are shown in FIG. 10.

Analysis of the vitreal data using a non-compartmental model indicated that both SIESD (AFD.v8) and SIESD.N103S (AFD.v14) have clearance properties very similar to ranibizumab. All three proteins gave very similar exposure, as reflected in the AUC parameter, in the three ocular compartments: vitreous humor, aqueous humor, and retina. PK parameters calculated for ranibizumab were consistent with results of earlier studies in rabbits (Gaudrealt et al, *Retina*, 27:1260-6 (2007)). Both SIESD (AFD.v8) and SIESD.N103S (AFD.v14) show target-independent ocular clearance properties that render these molecules suitable for development.

Example 6: Viscosity for AFD.v8/v14

As low viscosity is important for intravitreal administration, viscosity for SIESD (AFD.v8) and SIESD.N103S (AFD.v14) was measured at different protein concentrations in a pH 5.5, low salt buffer. Viscosity measurements were performed on a TA Instruments cone and plate rheometer thermostatted at 25° C. using a shear rate of 1000 s$^{-1}$.

aFD WT, SIESD (AFD.v8) and SIESD.N103S (AFD.v14) gave similar profiles of viscosity dependence on protein concentration with viscosities acceptable for intravitreal injection (<30 cP) even at concentrations exceeding 200 mg/mL (FIG. 11).

Those skilled in the art will recognize, or be able to ascertain using no more than routine experimentation, many equivalents to the specific embodiments of the invention described herein. Such equivalents are intended to be encompassed by the following claims.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. Indeed, various modifications of the invention in addition to those shown and described herein will become apparent to those skilled in the art from the foregoing description and fall within the scope of the appended claims.

We claim:

1. An anti-Factor D antibody comprising a light chain variable domain amino acid sequence of SEQ ID NO:19, and a heavy chain variable domain amino acid sequence of SEQ ID NO:20.

2. An anti-Factor D antibody comprising: a light chain variable domain comprising a HVR-L1 having the sequence of SEQ ID NO: 14, a HVR-L2 having the sequence of SEQ ID NO:6, and a HVR-L3 having the sequence of SEQ ID NO:7; and a heavy chain variable domain comprising a HVR-H1 having the sequence of SEQ ID NO:8, a HVR-H2 having the sequence of SEQ ID NO:12, and a HVR-H3 having the sequence of SEQ ID NO:15.

3. An anti-Factor D antibody having a light chain having the amino acid sequence of SEQ ID NO: 28 and a heavy chain having the amino acid sequence of SEQ ID NO: 29.

4. A pharmaceutical formulation comprising the antibody according to any one of claim 1, 2 and 3.

5. The pharmaceutical formulation according to claim 4, wherein the antibody is at a concentration of at least 100 mg/ml.

6. The pharmaceutical formulation according to claim 4, wherein the antibody is at a concentration of at least 200 mg/ml.

7. The pharmaceutical formulation according to claim 4, wherein the antibody is at a concentration of at least 300 mg/ml.

8. The pharmaceutical formulation according to claim 4, wherein the antibody is at a concentration of at least 500 mg/ml.

9. A kit comprising an anti-Factor D antibody of any one of claim 1, 2 and 3.

* * * * *

SEQUENCE LISTING

<160> NUMBER OF SEQ ID NOS: 33

<210> SEQ ID NO 1
<211> LENGTH: 214
<212> TYPE: PRT
<213> ORGANISM: Homo sapiens

<400> SEQUENCE: 1

```
Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 223
<212> TYPE: PRT
<213> ORGANISM: Homo sapiens

<400> SEQUENCE: 2

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 3
<211> LENGTH: 107
<212> TYPE: PRT
<213> ORGANISM: Homo sapiens

<400> SEQUENCE: 3

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys
            100                 105

<210> SEQ ID NO 4
<211> LENGTH: 115
<212> TYPE: PRT
<213> ORGANISM: Homo sapiens

<400> SEQUENCE: 4

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser
        115

<210> SEQ ID NO 5
<211> LENGTH: 11
<212> TYPE: PRT
<213> ORGANISM: Homo sapiens

<400> SEQUENCE: 5

Ile Thr Ser Thr Asp Ile Asp Asp Asp Met Asn
1               5                   10

<210> SEQ ID NO 6
<211> LENGTH: 7
<212> TYPE: PRT
<213> ORGANISM: Homo sapiens

<400> SEQUENCE: 6

Gly Gly Asn Thr Leu Arg Pro
1               5

<210> SEQ ID NO 7
<211> LENGTH: 9
<212> TYPE: PRT
<213> ORGANISM: Homo sapiens

<400> SEQUENCE: 7

Leu Gln Ser Asp Ser Leu Pro Tyr Thr
1               5

<210> SEQ ID NO 8
<211> LENGTH: 10
<212> TYPE: PRT
<213> ORGANISM: Homo sapiens

<400> SEQUENCE: 8

Gly Tyr Thr Phe Thr Asn Tyr Gly Met Asn
1               5                   10

<210> SEQ ID NO 9
<211> LENGTH: 17

```
<212> TYPE: PRT
<213> ORGANISM: Homo sapiens

<400> SEQUENCE: 9

Trp Ile Asn Thr Tyr Thr Gly Glu Thr Thr Tyr Ala Asp Asp Phe Lys
1               5                   10                  15

Gly

<210> SEQ ID NO 10
<211> LENGTH: 6
<212> TYPE: PRT
<213> ORGANISM: Homo sapiens

<400> SEQUENCE: 10

Glu Gly Gly Val Asn Asn
1               5

<210> SEQ ID NO 11
<211> LENGTH: 11
<212> TYPE: PRT
<213> ORGANISM: Homo sapiens

<400> SEQUENCE: 11

Ile Thr Ser Thr Asp Ile Glu Ser Asp Met Asn
1               5                   10

<210> SEQ ID NO 12
<211> LENGTH: 17
<212> TYPE: PRT
<213> ORGANISM: Homo sapiens

<400> SEQUENCE: 12

Trp Ile Asn Thr Tyr Thr Gly Glu Thr Thr Tyr Ala Glu Asp Phe Lys
1               5                   10                  15

Gly

<210> SEQ ID NO 13
<211> LENGTH: 9
<212> TYPE: PRT
<213> ORGANISM: Homo sapiens

<400> SEQUENCE: 13

Leu Gln Ser Glu Ser Leu Pro Tyr Thr
1               5

<210> SEQ ID NO 14
<211> LENGTH: 11
<212> TYPE: PRT
<213> ORGANISM: Homo sapiens

<400> SEQUENCE: 14

Ile Thr Ser Thr Ser Ile Glu Ser Asp Met Asn
1               5                   10

<210> SEQ ID NO 15
<211> LENGTH: 6
<212> TYPE: PRT
<213> ORGANISM: Homo sapiens

<400> SEQUENCE: 15

Glu Gly Gly Val Ser Asn
1               5
```

```
<210> SEQ ID NO 16
<211> LENGTH: 107
<212> TYPE: PRT
<213> ORGANISM: Homo sapiens

<400> SEQUENCE: 16

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys
            100                 105

<210> SEQ ID NO 17
<211> LENGTH: 115
<212> TYPE: PRT
<213> ORGANISM: Homo sapiens

<400> SEQUENCE: 17

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gly Thr Leu Val Thr
            100                 105                 110

Val Ser Ser
        115

<210> SEQ ID NO 18
<211> LENGTH: 107
<212> TYPE: PRT
<213> ORGANISM: Homo sapiens

<400> SEQUENCE: 18

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Glu Ser Leu Pro Tyr
                 85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: Homo sapiens

<400> SEQUENCE: 19

Asp Ile Gln Val Thr Gln Ser Pro Ser Ser Leu Ser Ala Ser Val Gly
  1               5                  10                  15

Asp Arg Val Thr Ile Thr Cys Ile Thr Ser Thr Ser Ile Glu Ser Asp
                20                  25                  30

Met Asn Trp Tyr Gln Gln Lys Pro Gly Lys Val Pro Lys Leu Leu Ile
             35                  40                  45

Ser Gly Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Val Glu Ile Lys
            100                 105

<210> SEQ ID NO 20
<211> LENGTH: 115
<212> TYPE: PRT
<213> ORGANISM: Homo sapiens

<400> SEQUENCE: 20

Glu Val Gln Leu Val Gln Ser Gly Pro Glu Leu Lys Lys Pro Gly Ala
  1               5                  10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
             35                  40                  45

Gly Trp Ile Asn Thr Tyr Thr Gly Glu Thr Thr Tyr Ala Glu Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Glu Gly Gly Val Ser Asn Trp Gly Gln Gly Thr Leu Val Thr
            100                 105                 110

Val Ser Ser
        115

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Cys Pro Pro Cys
1

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (7)..(7)
<223> OTHER INFORMATION: Asp or Glu
<220> FEATURE:
<221> NAME/KEY: MOD_RES
<222> LOCATION: (8)..(8)
<223> OTHER INFORMATION: Asp or Ser

<400> SEQUENCE: 22

Ile Thr Ser Thr Xaa Ile Xaa Xaa Asp Met Asn
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Asp or Glu

<400> SEQUENCE: 23

Trp Ile Asn Thr Tyr Thr Gly Glu Thr Thr Tyr Ala Xaa Asp Phe Lys
1               5                   10                  15

Gly

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asp or Glu

<400> SEQUENCE: 24

Leu Gln Ser Xaa Ser Leu Pro Tyr Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (5)..(5)
<223> OTHER INFORMATION: Asn or Ser

<400> SEQUENCE: 25

Glu Gly Gly Val Xaa Asn
1               5

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30
```

```
Gly Met Asn Trp Val Arg Gln Ala Pro Gly Gln Gly Leu Glu Trp Met
             35                  40                  45

Gly Trp Ile Asn Thr Tyr Thr Gly Glu Thr Thr Tyr Ala Glu Asp Phe
 50                      55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Glu Gly Gly Val Asn Asn Trp Gly Gln Gly Thr Leu Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Lys Val Glu Pro Lys Ser Cys Asp Lys Thr His Thr
    210                 215                 220

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Val Thr Gln Ser Pro Ser Ser Leu Ser Ala Ser Val Gly
 1               5                  10                  15

Asp Arg Val Thr Ile Thr Cys Ile Thr Ser Thr Ser Ile Glu Ser Asp
             20                  25                  30

Met Asn Trp Tyr Gln Gln Lys Pro Gly Lys Val Pro Lys Leu Leu Ile
         35                  40                  45

Ser Gly Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
              180                 185                 190

Ala Cys Glu Val Thr His Gln Gly Leu Ser Ser Pro Val Thr Lys Ser
          195                 200                 205

Phe Asn Arg Gly Glu Cys
    210

<210> SEQ ID NO 29
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr
    210                 215                 220

<210> SEQ ID NO 30
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

<210> SEQ ID NO 31
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly 165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys
225

<210> SEQ ID NO 32
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

<210> SEQ ID NO 33
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Pro Glu Leu Lys Lys Pro Gly Ala

```
1               5                   10                  15
Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
        50                  55                  60

Lys Gly Arg Phe Val Phe Ser Leu Asp Thr Ser Val Ser Thr Ala Tyr
65                      70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
            210                 215                 220

Pro Pro Cys
225
```